United States Patent
Kelly et al.

(10) Patent No.: US 10,857,277 B2
(45) Date of Patent: Dec. 8, 2020

(54) MODULAR HEMODIALYSIS SYSTEM

(75) Inventors: Thomas D. Kelly, Highland Park, IL (US); SuPing Lyu, Maple Grove, MN (US); Bryant J. Pudil, Plymouth, MN (US); Thomas E. Meyer, Stillwater, MN (US)

(73) Assignee: Medtronic, Inc., Minneapolis, MN (US)

(*) Notice: Subject to any disclaimer, the term of this patent is extended or adjusted under 35 U.S.C. 154(b) by 932 days.

(21) Appl. No.: 13/586,824

(22) Filed: Aug. 15, 2012

(65) Prior Publication Data

US 2013/0213890 A1 Aug. 22, 2013

Related U.S. Application Data

(60) Provisional application No. 61/524,291, filed on Aug. 16, 2011.

(51) Int. Cl.
*A61M 1/16* (2006.01)
*A61M 1/36* (2006.01)

(52) U.S. Cl.
CPC ............ *A61M 1/16* (2013.01); *A61M 1/1607* (2014.02); *A61M 1/1609* (2014.02);
(Continued)

(58) Field of Classification Search
CPC ........ A61M 1/16; A61M 1/1696; A61M 1/28; A61M 1/3679; A61M 1/281; A61M 1/284; A61M 1/34
See application file for complete search history.

(56) References Cited

U.S. PATENT DOCUMENTS

| 3,091,098 A | 5/1963 | Bowers |
| 3,370,710 A | 2/1968 | Bluemie, Jr. |

(Continued)

FOREIGN PATENT DOCUMENTS

| DE | 3215003 | 4/1985 |
| EP | 0022370 A1 | 1/1981 |

(Continued)

OTHER PUBLICATIONS

Ralph T. Yang, Adsorbents: Fundamentals and Applications 109 (2003).*

(Continued)

*Primary Examiner* — Krishnan S Menon
*Assistant Examiner* — Brad Gordon
(74) *Attorney, Agent, or Firm* — Hahn & Associates PLLC; Roger C. Hahn; Kenneth Collier

(57) ABSTRACT

Apparatuses, systems, and methods for the performance of kidney replacement therapy having or using a dialyzer, control components, sorbent cartridge, and fluid reservoirs configured to be of a weight and size suitable to be worn or carried by an individual requiring treatment are disclosed. The system has a controlled compliance dialysis circuit, where a control pump controls the bi-directional movement of fluid across a dialysis membrane. A first sorbent cartridge is provided for use in a portable treatment module having activated carbon and zirconium oxide. The system also provides for the monitoring of an inlet and outlet conductivity of a sorbent cartridge containing urease to provide a facility to quantify or monitor the removal of urea by a detachable urea removal module.

19 Claims, 9 Drawing Sheets

(52) U.S. Cl.
CPC ........ *A61M 1/1696* (2013.01); *A61M 1/3609* (2014.02); A61M 2205/3317 (2013.01); A61M 2205/3324 (2013.01); A61M 2205/3334 (2013.01); A61M 2205/50 (2013.01); A61M 2230/207 (2013.01)

(56) References Cited

U.S. PATENT DOCUMENTS

| | | |
|---|---|---|
| 3,506,126 A | 4/1970 | Lindsay, Jr. |
| 3,608,729 A | 9/1971 | Haselden |
| 3,669,878 A | 6/1972 | Marantz |
| 3,669,880 A | 6/1972 | Marantz |
| 3,692,648 A | 9/1972 | Matloff |
| 3,809,241 A | 5/1974 | Alvine |
| 3,850,835 A | 11/1974 | Marantz |
| 3,884,808 A | 5/1975 | Scott |
| 3,939,069 A | 2/1976 | Granger |
| 3,989,622 A | 11/1976 | Marantz |
| 4,060,485 A | 11/1977 | Eaton |
| 4,083,777 A * | 4/1978 | Hutchisson ............. A61M 1/16 210/186 |
| 4,094,775 A | 6/1978 | Mueller |
| 4,142,845 A * | 3/1979 | Lepp et al. ................ 417/477.8 |
| 4,180,460 A * | 12/1979 | Calari ................ A61M 1/1656 210/182 |
| 4,201,555 A | 5/1980 | Tkach |
| 4,209,392 A * | 6/1980 | Wallace ............. A61M 1/1696 128/DIG. 3 |
| 4,316,725 A | 2/1982 | Hovind |
| 4,371,385 A | 2/1983 | Johnson |
| 4,374,382 A | 2/1983 | Markowitz |
| 4,381,999 A | 5/1983 | Boucher |
| 4,430,098 A | 2/1984 | Bowman |
| 4,460,555 A | 7/1984 | Thompson |
| 4,490,135 A | 12/1984 | Troutner |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,678,408 A | 7/1987 | Mason |
| 4,685,903 A | 8/1987 | Cable |
| 4,695,385 A | 9/1987 | Boag |
| 4,715,398 A | 12/1987 | Shouldice |
| 4,750,494 A | 6/1988 | King |
| 4,826,663 A | 5/1989 | Alberti |
| 4,828,693 A | 5/1989 | Lindsay |
| 4,885,001 A | 12/1989 | Leppert |
| 4,900,308 A | 2/1990 | Verkaart |
| 4,915,713 A | 4/1990 | Buzza |
| 4,977,888 A | 12/1990 | Rietter |
| 5,080,653 A | 1/1992 | Voss |
| 5,092,886 A | 3/1992 | Dobos-Hardy |
| 5,097,122 A | 3/1992 | Coiman |
| 5,114,580 A | 5/1992 | Ahmad |
| 5,127,404 A | 7/1992 | Wyborny |
| 5,180,403 A | 1/1993 | Kogure |
| 5,284,470 A * | 2/1994 | Beltz ................... A61M 1/3472 210/321.71 |
| 5,302,288 A | 4/1994 | Meidl |
| 5,305,745 A | 4/1994 | Zacouto |
| 5,318,750 A | 6/1994 | Lascombes |
| 5,419,347 A | 5/1995 | Carruth |
| 5,468,388 A | 11/1995 | Goddard |
| 5,591,344 A * | 1/1997 | Kenley ..................... A61L 2/04 210/134 |
| 5,683,432 A | 11/1997 | Goedeke |
| 5,685,835 A | 11/1997 | Brugger |
| 5,702,536 A | 12/1997 | Carruth |
| 5,744,031 A | 4/1998 | Bene |
| 5,762,782 A | 6/1998 | Kenley |
| 5,863,421 A | 1/1999 | Peter |
| 5,938,938 A * | 8/1999 | Bosetto et al. ................ 210/739 |
| 5,944,684 A * | 8/1999 | Roberts ............... A61M 1/1696 210/646 |
| 5,948,251 A | 9/1999 | Brugger |
| 6,048,732 A | 4/2000 | Anslyn |
| 6,052,622 A | 4/2000 | Holmstrom |
| 6,058,331 A | 5/2000 | King |
| 6,230,059 B1 | 5/2001 | Duffin |
| 6,248,093 B1 | 6/2001 | Moberg |
| 6,251,167 B1 | 6/2001 | Berson |
| 6,254,567 B1 | 7/2001 | Treu |
| 6,264,680 B1 | 7/2001 | Ash |
| 6,321,101 B1 | 11/2001 | Holmstrom |
| 6,362,591 B1 | 3/2002 | Moberg |
| 6,363,279 B1 | 3/2002 | Ben-Haim |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,627,164 B1 | 9/2003 | Wong |
| 6,676,608 B1 | 1/2004 | Keren |
| 6,711,439 B1 | 3/2004 | Bradley |
| 6,726,647 B1 | 4/2004 | Sternby |
| 6,780,322 B1 | 8/2004 | Bissler |
| 6,814,724 B2 | 11/2004 | Taylor |
| 6,818,196 B2 | 11/2004 | Wong |
| 6,824,524 B1 | 11/2004 | Favre |
| 6,878,283 B2 | 4/2005 | Thompson |
| 6,960,179 B2 | 11/2005 | Gura |
| 7,023,359 B2 | 4/2006 | Goetz |
| 7,074,332 B2 | 7/2006 | Summerton |
| 7,077,819 B1 | 7/2006 | Goldau |
| 7,208,092 B2 | 4/2007 | Micheli |
| 7,241,272 B2 | 7/2007 | Karoor |
| 7,276,042 B2 | 10/2007 | Polaschegg |
| 7,279,031 B1 | 10/2007 | Wright |
| 7,500,958 B2 | 3/2009 | Asbrink |
| 7,566,432 B2 | 6/2009 | Wong |
| 7,575,564 B2 | 8/2009 | Childers |
| 7,597,806 B2 | 10/2009 | Uchi |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,776,210 B2 | 8/2010 | Rosenbaum |
| 7,785,463 B2 | 8/2010 | Bissler |
| 7,790,103 B2 | 9/2010 | Shah |
| 7,794,141 B2 | 9/2010 | Perry |
| 7,850,635 B2 | 12/2010 | Polaschegg |
| 7,854,718 B2 * | 12/2010 | Gura ................... A61M 1/1696 210/645 |
| 7,857,976 B2 | 12/2010 | Bissler |
| 7,867,214 B2 | 1/2011 | Childers |
| 7,871,390 B2 * | 1/2011 | Rambod ................ A61M 1/16 210/645 |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum et al. |
| 7,955,291 B2 | 6/2011 | Sternby |
| 7,967,022 B2 | 6/2011 | Grant |
| 7,981,082 B2 | 7/2011 | Wang |
| 8,002,726 B2 | 8/2011 | Karoor |
| 8,034,161 B2 | 10/2011 | Gura |
| 8,070,709 B2 | 12/2011 | Childers |
| 8,096,969 B2 | 1/2012 | Roberts |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,409,441 B2 | 4/2013 | Wilt |
| 8,449,487 B2 | 5/2013 | Hovland |

(56) References Cited

U.S. PATENT DOCUMENTS

| | | |
|---|---|---|
| 8,491,517 B2 | 7/2013 | Karoor |
| 8,496,809 B2 | 7/2013 | Roger |
| 8,499,780 B2 | 8/2013 | Wilt |
| 8,500,672 B2 | 8/2013 | Caleffi |
| 8,500,676 B2 | 8/2013 | Jansson |
| 8,500,994 B2 | 8/2013 | Weaver |
| 8,512,271 B2 | 8/2013 | Moissl |
| 8,518,258 B2 | 8/2013 | Balschat |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,562,822 B2 | 10/2013 | Roger |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,906,240 B2 | 12/2014 | Crnkovich |
| 2002/0042561 A1 | 4/2002 | Schulman |
| 2002/0045851 A1 | 4/2002 | Suzuki |
| 2002/0104800 A1 | 8/2002 | Collins |
| 2002/0112609 A1* | 8/2002 | Wong ................ 96/131 |
| 2003/0010717 A1 | 1/2003 | Brugger |
| 2003/0080059 A1 | 5/2003 | Peterson |
| 2003/0097086 A1 | 5/2003 | Gura |
| 2003/0100864 A1* | 5/2003 | Bendsen ................ A61M 5/28 |
| | | 604/141 |
| 2003/0105435 A1 | 6/2003 | Taylor |
| 2003/0114787 A1 | 6/2003 | Gura |
| 2004/0019312 A1* | 1/2004 | Childers ................ A61M 1/288 |
| | | 604/4.01 |
| 2004/0068219 A1 | 4/2004 | Summerton |
| 2004/0082903 A1* | 4/2004 | Micheli ................ 604/29 |
| 2004/0099593 A1 | 5/2004 | DePaolis |
| 2004/0143173 A1 | 7/2004 | Reghabi et al. |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0101901 A1* | 5/2005 | Gura ................ A61M 1/3639 |
| | | 604/5.02 |
| 2005/0113796 A1 | 5/2005 | Taylor |
| 2005/0115898 A1 | 6/2005 | Sternby |
| 2005/0126961 A1 | 6/2005 | Bissler |
| 2005/0131331 A1 | 6/2005 | Kelly |
| 2005/0131332 A1* | 6/2005 | Kelly ................ A61M 1/1633 |
| | | 604/4.01 |
| 2005/0126998 A1 | 7/2005 | Childers |
| 2005/0150832 A1 | 7/2005 | Tsukamoto |
| 2005/0234381 A1 | 10/2005 | Niemetz |
| 2005/0274658 A1 | 12/2005 | Rosenbaum et al. |
| 2006/0025661 A1 | 2/2006 | Sweeney |
| 2006/0217771 A1 | 2/2006 | Soykan |
| 2006/0054489 A1 | 3/2006 | Denes |
| 2006/0076295 A1 | 4/2006 | Leonard |
| 2006/0157335 A1 | 7/2006 | Levine |
| 2006/0157413 A1* | 7/2006 | Bene ................ A61M 1/16 |
| | | 210/646 |
| 2006/0195064 A1 | 8/2006 | Plahey |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0072285 A1 | 3/2007 | Barringer |
| 2007/0138011 A1 | 6/2007 | Hofmann |
| 2007/0175827 A1 | 8/2007 | Wariar |
| 2007/0179431 A1 | 8/2007 | Roberts et al. |
| 2007/0208292 A1* | 9/2007 | Ferrari ................ A61M 1/14 |
| | | 604/6.16 |
| 2007/0213653 A1 | 9/2007 | Childers |
| 2007/0213665 A1 | 9/2007 | Curtin |
| 2007/0215545 A1 | 9/2007 | Bissler |
| 2007/0255250 A1 | 11/2007 | Moberg |
| 2008/0006570 A1 | 1/2008 | Gura et al. |
| 2008/0021337 A1 | 1/2008 | Li |
| 2008/0053905 A9 | 3/2008 | Brugger |
| 2008/0067132 A1 | 3/2008 | Ross |
| 2008/0093276 A1* | 4/2008 | Roger ................ A61M 1/28 |
| | | 210/104 |
| 2008/0154543 A1 | 6/2008 | Rajagopal |
| 2008/0215247 A1 | 9/2008 | Tonelli |
| 2008/0230473 A1 | 9/2008 | Herbst |
| 2008/0253427 A1 | 10/2008 | Kamen |
| 2009/0012450 A1 | 1/2009 | Shah |
| 2009/0020471 A1 | 1/2009 | Tsukamoto |
| 2009/0078636 A1 | 3/2009 | Uchi |
| 2009/0084721 A1 | 4/2009 | Yardimci |
| 2009/0101549 A1 | 4/2009 | Kamen |
| 2009/0101577 A1 | 4/2009 | Fulkerson |
| 2009/0105629 A1 | 4/2009 | Grant |
| 2009/0107335 A1* | 4/2009 | Wilt ................ A61M 1/3627 |
| | | 95/261 |
| 2009/0127193 A1 | 4/2009 | Updyke |
| 2009/0120864 A1* | 5/2009 | Fulkerson ............ A61M 1/1601 |
| | | 210/198.1 |
| 2009/0124963 A1* | 5/2009 | Hogard ................ A61M 1/14 |
| | | 604/30 |
| 2009/0131858 A1 | 5/2009 | Fissell |
| 2009/0157877 A1 | 6/2009 | Baek |
| 2009/0171261 A1 | 7/2009 | Sternby |
| 2009/0182263 A1 | 7/2009 | Burbank |
| 2009/0187138 A1 | 7/2009 | Lundtveit |
| 2009/0216045 A1 | 8/2009 | Singh |
| 2009/0223539 A1 | 9/2009 | Gibbel |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1* | 1/2010 | Yeh ................ A61M 1/14 |
| | | 604/28 |
| 2010/0007838 A1 | 1/2010 | Fujimoto |
| 2010/0022936 A1 | 1/2010 | Gura |
| 2010/0030151 A1 | 2/2010 | Kirsch |
| 2010/0042035 A1 | 2/2010 | Moissl |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0100027 A1 | 4/2010 | Schilthuizen |
| 2010/0114012 A1* | 5/2010 | Sandford ............ A61M 1/1696 |
| | | 604/28 |
| 2010/0130906 A1 | 5/2010 | Balschat |
| 2010/0137693 A1 | 6/2010 | Porras |
| 2010/0137782 A1 | 6/2010 | Jansson |
| 2010/0140149 A1 | 6/2010 | Fulkerson |
| 2010/0168546 A1 | 7/2010 | Kamath |
| 2010/0192686 A1 | 8/2010 | Kamen |
| 2010/0199670 A1 | 8/2010 | Robertson |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0252490 A1* | 10/2010 | Fulkerson ............ A61M 1/1656 |
| | | 210/96.2 |
| 2010/0274171 A1 | 10/2010 | Caleffi |
| 2010/0312174 A1 | 12/2010 | Hoffman |
| 2010/0326911 A1 | 12/2010 | Rosenbaum |
| 2010/0327586 A1 | 12/2010 | Mardirossian |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |

(56) References Cited

U.S. PATENT DOCUMENTS

| | | |
|---|---|---|
| 2011/0120946 A1 | 5/2011 | Levin |
| 2011/0130666 A1 | 6/2011 | Dong |
| 2011/0132838 A1 | 6/2011 | Curtis |
| 2011/0144570 A1 | 6/2011 | Childers |
| 2011/0160637 A1 | 6/2011 | Beiriger |
| 2011/0163030 A1 | 7/2011 | Weaver |
| 2011/0184340 A1 | 7/2011 | Tan |
| 2011/0189048 A1 | 8/2011 | Curtis |
| 2011/0220562 A1 | 9/2011 | Beiriger |
| 2011/0272337 A1 | 11/2011 | Palmer |
| 2011/0315611 A1 | 12/2011 | Fulkerson |
| 2012/0006762 A1 | 1/2012 | McCabe |
| 2012/0016228 A1 | 1/2012 | Kroh |
| 2012/0031825 A1 | 2/2012 | Gura |
| 2012/0083729 A1 | 4/2012 | Childers |
| 2012/0085707 A1 | 4/2012 | Beiriger |
| 2012/0115248 A1 | 5/2012 | Ansyln |
| 2012/0219528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0302945 A1 | 11/2012 | Hedmann |
| 2013/0018301 A1 | 1/2013 | Weaver |
| 2013/0019994 A1 | 1/2013 | Schaer |
| 2013/0037465 A1 | 2/2013 | Heyes |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228516 A1* | 9/2013 | Jonsson et al. ............... 210/646 |
| 2013/0228517 A1 | 9/2013 | Roger |
| 2013/0231607 A1 | 9/2013 | Roger |
| 2013/0248426 A1 | 9/2013 | Pouchoulin |
| 2013/0256227 A1 | 10/2013 | Kelly |
| 2013/0274642 A1 | 10/2013 | Soykan |
| 2013/0304020 A1 | 11/2013 | Wilt |
| 2013/0324915 A1 | 12/2013 | (Krensky) Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0224736 A1 | 8/2014 | Heide |
| 2015/0057602 A1 | 2/2015 | Mason |
| 2015/0083647 A1 | 3/2015 | Meyer |
| 2015/0114891 A1 | 4/2015 | Meyer |
| 2015/0144539 A1 | 5/2015 | Pudil |
| 2016/0038666 A1 | 2/2016 | Kelly |
| 2016/0166748 A1 | 6/2016 | Meyer |
| 2016/0166751 A1 | 6/2016 | Meyer |
| 2016/0166752 A1 | 6/2016 | Meyer |
| 2016/0166753 A1 | 6/2016 | Meyer |

FOREIGN PATENT DOCUMENTS

| | | |
|---|---|---|
| EP | 0187109 | 7/1986 |
| EP | 266795 A2 | 11/1987 |
| EP | 0298587 | 6/1994 |
| EP | 0743071 | 11/1996 |
| EP | 1124599 | 5/2000 |
| EP | 1175238 | 11/2000 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 1490129 | 9/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2388030 | 11/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 1414543 | 9/2013 |
| EP | 2701596 | 3/2014 |
| EP | 1787666 | 11/2015 |
| FR | 2237639 | 2/1977 |
| JP | 2002306904 | 10/2002 |
| JP | 5099464 | 10/2012 |
| WO | 1996040313 | 12/1996 |
| WO | 9937342 | 7/1999 |
| WO | 0057935 | 10/2000 |
| WO | 2000066197 | 11/2000 |
| WO | 2001085295 A2 | 9/2001 |
| WO | 200066197 A1 | 11/2001 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 200170307 A1 | 4/2004 |
| WO | 2004030716 A2 | 4/2004 |
| WO | 2004030717 A2 | 4/2004 |
| WO | 2004064616 A2 | 8/2004 |
| WO | 2004105589 A2 | 12/2004 |
| WO | 2005044339 | 5/2005 |
| WO | 2004105589 A3 | 6/2005 |
| WO | 2005061026 | 7/2005 |
| WO | 2005123230 A2 | 12/2005 |
| WO | 2006023589 A2 | 3/2006 |
| WO | 2007010164 A2 | 1/2007 |
| WO | 2007089855 A2 | 8/2007 |
| WO | 2007146162 A2 | 12/2007 |
| WO | 2007146162 A3 | 12/2007 |
| WO | 2008037410 | 4/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009064984 | 5/2009 |
| WO | 2009071103 | 6/2009 |
| WO | 2009094184 | 7/2009 |
| WO | 2009132839 A1 | 11/2009 |
| WO | 2009157877 A1 | 12/2009 |
| WO | 2009157877 A1 | 12/2009 |
| WO | 2009157878 A1 | 12/2009 |

(56) References Cited

FOREIGN PATENT DOCUMENTS

| | | |
|---|---|---|
| WO | 2010028860 A1 | 2/2010 |
| WO | 2010028860 | 3/2010 |
| WO | 2010042666 | 4/2010 |
| WO | 2010042666 A2 | 4/2010 |
| WO | 2010052705 A1 | 5/2010 |
| WO | 2010062698 | 6/2010 |
| WO | 2010096659 | 10/2010 |
| WO | 2010121820 | 10/2010 |
| WO | 2011017215 A1 | 2/2011 |
| WO | 2011025705 A1 | 3/2011 |
| WO | 2012026978 | 3/2012 |
| WO | 2012042323 | 4/2012 |
| WO | 2012050781 | 4/2012 |
| WO | 2012051996 | 4/2012 |
| WO | 2012067585 | 5/2012 |
| WO | 2010042666 A3 | 6/2012 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013025844 A2 | 2/2013 |
| WO | 2013027214 | 2/2013 |
| WO | 2013028809 A2 | 2/2013 |
| WO | 2013028809 A3 | 2/2013 |
| WO | 2013019994 A3 | 4/2013 |
| WO | 2013025844 A3 | 5/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013188861 A1 | 12/2013 |
| WO | 14066254 | 5/2014 |
| WO | 14066255 | 5/2014 |
| WO | 14077082 | 5/2014 |
| WO | 2014117000 | 7/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

Ruperez et al., Comparison of a Tubular Pulsatile Pump and a Volumetric Pump for Continuous Venovenous Renal Replacement Therapy in a Pediatric Animal Model, 51 Asaio J. 372, 372-375 (2005).*
St. Peter et al., Liver and kidney preservation by perfusion, 359 The Lancet 604, 606 (2002).*
Dasselaar et al., Measurement of relative blood volume changes during haemodialysis: merits and limitations, 20 Nephrol. Dial. Transpl. 2043, 2043-2044 (2005).*
Henny H. Billett, Hemoglobin and Hematocrit, in Clinical Methods: The History, Physical, and Laboratory Examinations 719 (HK Walker, WD Hall, & JW Hurst ed., 1990).*
Roberts M, The regenerative dialysis (REDY) sorbent system, Nephrology, 1996, 275-278: 4.
Marchant, et. al., In vivo Biocompatibility Studies I: The Cage Implant System and a Biodegradable Hydrogel, J. Biomed. Mat. Res., 1983, 301-325: 17.
Siegenthalar, et. al., Pulmonary fluid status monitoring with intrathoracic impedance, Journal of Clinical Monitoring and Computing, 2010, 449-451 : 24.
Wang, Fundamentals of intrathoracic impedance monitoring in heart failure, Am. J. Cardiology, 2007, 3G-10G : Suppl.

PCT/US2012/025711 International Search Report dated Jul. 4, 2012.
PCT/US2012/051011, International Search Report, dated Jan. 17, 2014.
PCT Application, PCT/US20013/020404, filed Jan. 4, 2013.
U.S. Appl. No. 14/261,651, filed Apr. 25, 2014.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2012/051011, International Search Report and Written Opinion, dated Mar. 4, 2013.
Examination report for Australian Application No. AU2014212135 dated May 25, 2017.
Office Action for Chinese Application 20148007136.3, dated Jun. 15, 2017.
European Office Action in Application 14746793.0 dated Apr. 13, 2017.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Written Opinion of the International Searching Authority for PCT/US2012/049398 dated Feb. 25, 2013.
Gambro AK 96 Dialysis Machine Operator's Manual, Dec. 2012.
European Search Report 12819714.2-1651/2739325 PCT/US2012049398, dated Jun. 12, 2015.
Office Action in U.S. Appl. No. 13/565,733 dated Jan. 11, 2016.
Office Action in U.S. Appl. No. 13/565,733 dated Jun. 11, 2015.
Office Action in U.S. Appl. No. 13/791,755 dated Mar. 16, 2016.
Office Action in U.S. Appl. No. 13/791,755 dated Aug. 9, 2016.
Office Action in U.S. Appl. No. 13/791,755 dated Sep. 10, 2015.
Office Action in U.S. Appl. No. 13/791,755 dated Apr. 20, 2015.
Office Action in U.S. Appl. No. 14/259,589 dated Nov. 4, 2016.
Office Action in U.S. Appl. No. 14/261,651 dated Aug. 25, 2016.
U.S. Appl. No. 13/757,693, filed Feb. 1, 2013.
PCT/US2014/14343 Int'l Search Report & Written Opinion, dated Sep. 2006.
EP 14746791 Supplementary European Search Report dated Aug. 19, 2016.
PCT/US2014/014350 International Search Report and Written Opinion dated May 2014.
EP 14746793 Supplementary European Search Report dated Aug. 18, 2016.
U.S. Appl. No. 29/446,285, filed Feb. 1, 2013.
U.S. Appl. No. 61/526,209.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
U.S. Appl. No. 13/835,735, filed Mar. 15, 2013.
PCT/US2014/014345 International Search Report and Written Opinion, dated May 2014.
Leifer et al., 'A Study on the Temperature Variation of Rise Velocity for Large Clean Bubbles,' J. Atmospheric & Oceanic Tech., vol. 17, pp. 1392-1402.
Talaia, 'Terminal Velocity of a Bubble Rise in a Liquid Column,' World Acad. of Sci., Engineering & Tech., vol. 28, pp. 264-268.
The FHN Trial Group. In-Center. Hemodialysis Six Times per Week versus Three Times per Week, New England Journal of Medicine, 2010 Abstract.
PCT/US2014/014357 International Search Report and Written Opinion.
U.S. Appl. No. 13/757,722, filed Feb. 1, 2013.
U.S. Appl. No. 13/757,794, filed Feb. 2, 2012.
U.S. Appl. No. 13/791,755, filed Mar. 8, 2013.
U.S. Appl. No. 13/757,792, filed Feb. 2, 2013.
U.S. Appl. No. 13/837,287, filed Mar. 15, 2013.
U.S. Appl. No. 13/757,794, filed Feb. 2, 2013.
Weissman, S., et al., "Hydroxyurea-induced hepatitis in human immunodeficiency virus-positive patients." Clin. Infec. Dis, (Jul. 29, 1999): 223-224.
MacLean, et, al., Effects of hindlimb contraction on pressor and muscle interstitial metabolite responses in the cat, J. App. Physiol., 1998, 1583-1592, 85(4).

(56) References Cited

OTHER PUBLICATIONS

Overgaard, et. al., Activity-induced recovery of excitability in K+-depressed rat soieus muscle, Am. J. P.
Overgaard. et. al., Relations between excitability and contractility in rate soleus'muscle: role of the Na+—K+ pump and Na+—K—S gradients. Journal of Physiology, 1999, 215-225, 518(1).
Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
Ronco et al. 2008, 'Cardiorenal Syndrome,' Journal American College Cardiology, 52:1527-1539, Abstract.
U.S. Appl. No. 61/480,544.
PCT/US2014/067650 International Search Report Written Opinion dated Mar. 9, 2015.
Brynda, et. al., The detection of toman 2-microglcbuiin by grating coupler immunosensor with three dimensional antibody networks. Biosensors & Bioelectronics, 1999, 363-368, 14(4).
Hemametrics, Crit-Line Hematocrit Accuracy, 2003, 1-5, vol. 1, Tech Note No. 11 (Rev. D).
Lima, et. al., An electrochemical sensor based on nanostructure hollsndite-type manganese oxide for detection of potassium ion, Sensors, 2009, 6613-8625, 9.
Nedelkov, et. al., Design of buffer exchange surfaces and sensor chips for biosensor chip mass spectrometry, Proteomics, 2002, 441-446, 2(4).
PCT/US/2012/034327, International Search Report, dated Aug. 13, 2013.
PCT/US/2012/034329, International Search Report, dated Dec. 3, 2012.
PCT/US2012/034331, International Search Report, dated Jul. 9, 2012.
PCT/US2012/034332, International Search Report, dated Jul. 5, 2012.
PCT/US2012/034334, International Search Report, dated Jul. 6, 2012.
PCT/US2012/034335, International Search Report, dated Sep. 5, 2012.
Redfield, et. al, Restoration of renal response to atria! natriuretic factor in experimental low-output heat failure, Am. J. Physiol., 1989, R917-923:257.
Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
Coast, et al. 1990, An approach to Cardiac Arrhythmia analysis Using Hidden Markov Models, IEEE Transactions on Biomedical Engineering. 1990, 37(9):826-835.
U.S. Appl. No. 13/368,225.
U.S. Appl. No. 13/424,533.
U.S. Appl. No. 13/424,467.
U.S. Appl. No. 13/424,454.
U.S. Appl. No. 13/424,490.
U.S. Appl. No. 13/424,517.
U.S. Appl. No. 61/480,532.
PCT/US2012/034330, International Preliminary Report on Patentability, dated Oct. 29, 2013.
PCT/US2012/034333, International Preliminary Report on Patentability, dated Oct. 29, 2013.
PCT/US2012/034333, International Search Report, dated Aug. 29, 2013.
U.S. Appl. No. 13/424,429.
U.S. Appl. No. 13/424,479.
U.S. Appl. No. 13/424,525.
U.S. Appl. No. 61/480,528.
U.S. Appl. No. 61/480,530.
U.S. Appl. No. 61/480,535.
U.S. Appl. No. 61/480,539.
U.S. Appl. No. 61/480,541.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
Bleyer, et. al., Sudden and cardiac death rated in hemodialysis patients, Kidney International. 1999, 1553-1559: 55.
EP 14746799 Supplementary European Seach Report dated Aug. 18, 2016.
EP13182115.9-1651 European Search Report, dated Feb. 3, 2014.
Dasselaar et al., Measurement of relative blood vol. changes during hemodialysis: merits and limitations, 20 Nephrol Dial Transpl. 2043, 2043-2044 (2005).
St. Peter et al., Liver and Kidney Preservation by perfusion, 369 The Lancet 604, 606 (2002).
Franks, Gene, Cabon Filtration: What it does, What it doesn't, Mar. 14, 2012, pp. 1-3.
EP Search Report for Application No. 16204175.0 dated Mar. 29, 2017.
Office Action for Chinese Application 201510713880.1 dated Apr. 1, 2017.
Office Action for Chinese Application 201510761050.6 dated Aug. 2, 2017.
Examination report for Australian Application 2015361083 dated Jul. 20, 2017.
International Preliminary Report on Patentability for PCT2015/060090 dated Jun. 13, 2017.

\* cited by examiner

MODULAR HEMODIALYSIS SYSTEM

FIELD OF THE INVENTION

The invention relates to systems and methods of treatment by hemodialysis and hemofiltration for pathological conditions such as End Stage Renal Disease (ESRD). The systems and methods include a portable system having a dialyzer, control components, and a sorbent cartridge for dialysate configured to include an activated carbon sorbent material. The disclosure further relates to the treatment of Chronic Kidney Disease (CKD) through methods and apparatuses that allow an individual to remain ambulatory during treatment for the removal of uremic waste species and phosphates and to employ a base station module for the periodic removal of urea.

BACKGROUND

Urea is a neutral, polar and water miscible compound that is not readily separated from an aqueous solution, and is the main product of nitrogen metabolism by the body. In individuals with normal kidney function, urea is produced by the liver and accumulates in the blood to the level of few millimoles per liter. Filtration of the blood by the kidneys to remove urea keeps urea concentration from reaching unsafe levels. Individuals with kidney disease have insufficient clearance function to prevent urea from reaching unsafe levels.

During dialysis, the patient's blood, which contains a high concentration of waste solutes, is exposed to a semi-permeable membrane in contact with a solute-deficient dialysate. Solute removal, such as urea, is accomplished via diffusion across the membrane. Once the blood is purified, it is then returned to the patient. Although effective at removing wastes from blood, dialysis treatments are administered intermittently and therefore do not emulate the continuous function of the natural renal system. These procedures are usually carried out three times a week in three- to five-hour sessions. Due to the time-intensive requirements of in-patient dialysis treatment, many patients eventually elect to forego treatment on this basis alone. Moreover, due to the limitations and inconvenience of existing hemodialysis equipment, implementation of more frequent treatment is costly and patient compliance is expected to be difficult despite the possibility that high morbidity observed for End Stage Renal Disease (ESRD) patients receiving kidney replacement therapy may be the result of factors other than urea buildup in the blood.

During traditional hemodialysis treatment, a constant volume of fresh dialysate is provided for the performance of dialysis. Due to the large volume of dialysate needed and specialized water hookup and disposal facilities required for traditional dialysis treatment, traditional hemodialysis treatment is limited to specialized clinical facilities. Prior equipment for home dialysis treatment relies on the continual regeneration of a fixed volume of dialysate to maintain a diffusion gradient between the patient's blood and the dialysate. However, the amount of dialysate fluid subject to regeneration is typically in excess of 6 L making portability of the system during treatment impractical. The large volume of dialysate fluid required for dialysis is in part attributable to the large quantity of water necessary for the dissolution of electrolytes generated within the dialysate during treatment.

The use of a fixed volume of dialysate requires a means for the removal of waste species, such as urea, and impurities, to maintain a supply of refreshed, waste solute-depleted dialysate. In order for spent dialysate to be reused, accumulated waste products and impurities must be removed from the spent dialysate, and the composition and pH of the regenerated dialysate must be regulated for physiological compatibility. For example, the Recirculating Dialysate System ("REDY system"), which was introduced in the 1970, employs a sorbent cartridge through which spent dialysate is recirculated and regenerated. However, the regenerated dialysate produced by REDY systems is subject to variations in pH and sodium concentration requiring on-going adjustment.

Moreover, traditional dialysis systems employing sorbent technology, such as the REDY system usually employ low-flux dialyzers and adjust dialysate pressure to achieve net patient fluid removal. The UF coefficient of a dialyzer specifies the rate of filtration through the dialyzer due to pressure differences across the dialyzer membrane, typically called the trans-membrane pressure. The trans-membrane pressure is calculated by the formula TMP=((Blood Inlet Pressure+Blood Outlet Pressure)/2)−((Dialysate Inlet Pressure+Dialysate Outlet Pressure)/2). This formula is usually shortened to TMP=Venous Return Pressure−Dialysate Pressure. Low flux hemodialyzers have a UF coefficient of less than 8 ml of water flux per hour per mmHg of trans-membrane pressure. To illustrate fluid removal with the traditional sorbent system, a typical low flux dialyzer could have a UF coefficient of 4 mL/hr/mmHg. To calculate the pressure necessary to achieve the rate of fluid removal, the desired hourly fluid removal is divided by the dialyzer UF coefficient. For example, an hourly rate of 0.5 L/hr yields a required trans-membrane pressure (TMP) of 125 mmHg if the UF coefficient is 4 mL/hr/mmHg. 125 mmHg is the trans-membrane pressure required to remove fluid at a rate of 0.5 L per hour. The venous pressure is a function of the blood flow rate and the blood return restriction (needle and access). As the Venous Return Pressure cannot be set, to control the fluid removal rate it is necessary calculate the required dialysate pressure. The operator calculates dialysate pressure via the formula Dialysate Pressure=Venous Pressure−TMP, if the venous return pressure were 75 mmHg, (DP=75−125=−50 mmHg). In this example, the user must adjust the dialysate pressure to −50 mmHg to achieve the TMP of 125 mmHg. The venous pressure fluctuates during treatment so the operator must adjust the dialysate pressure on a regular basis, which is not suitable for a non-medical professional or a home patient. With high-flux dialyzers, pressure alone is not accurate enough to control ultrafiltration because fluid is moves more freely across the dialyzer membrane. To control ultrafiltration in conventional hemodialysis using high-flux dialyzers, balancing chambers, flow sensors or other methods to balance flow to and from the dialyzer are employed. In CRRT (continuous blood purification machine) equipment, pumps controlled by precise scales are required to control the flow to and from the dialyzer very accurately.

Although some sorbent materials, such as activated carbon, have some capacity to absorb urea, absorption is not efficient enough for use in hemodialysis treatment. To facilitate the removal of urea, many systems employ a material containing a urease enzyme that converts urea to ammonia and carbon dioxide. At the slightly basic pH of the dialysate, the ammonia generated from the activity of urease enzyme is present as ammonium ions, which can then be removed from solution by cation exchange with zirconium phosphate materials. While enabling removal of urea, the cation exchange process releases sodium and hydrogen into the dialysate in a stoichiometric fashion. In order to maintain a stable composition of the dialysate, sodium ion concentration must be reduced either by absorption of sodium ions or by dilution. Further, the generation of carbon dioxide and hydrogen ions leads to pH instability of the dialysate that can require infusion of bicarbonate or other means to adjust pH. Still further, cation exchange materials, including zirconium phosphate, remove essential electrolytes from the dialysate, such as $Mg^{2+}$, $Ca^{2+}$ and $K^+$, requiring continually replacement to ensure patient safety. Information pertaining to sorbent-based dialysate regeneration can be found in U.S. Pat. No. 3,669,878 Marantz et al., which describes sorbent removal of urea and ammonium ions from spent dialysate via urease, ammonium carbonate, and zirconium phosphate, U.S. Pat. No. 3,669,880 Marantz et al., which describes directing a controlled volume of dialysate through zirconium phosphate, activated carbon, and hydrated zirconium oxide columns, U.S. Pat. No. 3,850,835 Marantz et al., which describes production of a zirconium hydrous oxide ion exchange media, and U.S. Pat. No. 3,989,622 Marantz et al., which describes adsorption of urease on aluminum oxide and magnesium silicate media to convert liquid urea to ammonium carbonate. Additional information can be found in U.S. Pat. No. 4,581,141 Ash, which describes removal of uremic substances from dialysate via a calcium-based cation exchanger, urease, and aliphatic carboxylic acid resin. U.S. Pat. No. 4,826,663 Alberti et al. describes a method of preparing a zirconium phosphate ion exchanger. U.S. Pat. No. 6,627,164 Wong describes production of sodium zirconium carbonate for ion exchange in renal dialysis, and U.S. Pat. No. 7,566,432 Wong describes production of zirconium phosphate particles for ion exchange in regenerative dialysis. U.S. Pat. No. 6,818,196 Wong, U.S. Pat. No. 7,736,507 Wong, U.S. Application Publication 2002/0112609 Wong, U.S. Application Publication 2010/0078387 Wong, and U.S. Application Publication 2010/00784330 Wong, describe cartridges for purification of dialysis solutions using sodium zirconium carbonate.

U.S. Pat. No. 6,878,283 Thompson, U.S. Pat. No. 7,776, 210 Rosenbaum et al., U.S. Application Publication 2010/0326911 Rosenbaum et al., U.S. Application Publication 2010/0078381 Merchant, U.S. Application Publication 2009/0127193 Updyke et al. and U.S. Application Publication 2011/0017665 Updyke et al. describe filter cartridges having a plurality of types of filter media including zirconium compounds, urease, and alumina for dialysis systems. WO 2009/157877 A1 describes a urease material having urease immobilized on a substrate intermixed with a cation exchange material or zirconium phosphate material to improve workability for the reduction of clogging and to improve absorption of ammonium ions generated by the urease.

With regard to the management of waste species in regenerated dialysate, additional information can be found in U.S. Pat. No. 4,460,555 Thompson and U.S. Pat. No. 4,650,587 Polak et al., which describes magnesium phosphate media for removal of ammonia from aqueous solutions. U.S. Application Publication 2009/0282980 Gura et al. describes degassing devices for use in dialysis systems having urease media.

The above-described effects of traditional urease-based technologies has complicated the development of ultraportable and/or wearable dialysis systems that can facilitate more frequent, or even continuous, renal replacement therapy, and that can provide continual treatment that more closely mimics the natural function of the kidneys. Specifically, several different control systems are normally required by the device to control for sodium content, electrolyte content, and pH of the dialysate that are affected by the urease approach for the removal of urea from the dialysate. Moreover, none of the dialysis systems known in the art and commercialized are mobile such that the weight and volume of the system is sufficiently appropriate to be used by a patient while ambulatory.

Hence, there is a need for such devices, which can facilitate regular usage, but is also conducive to operation by a patient without the assistance of a medical professional. The systems should be designed to simplify operation of a portable or wearable device to facilitate more frequent hemodialysis treatment. There also remains a need for a patient-friendly wearable and/or portable dialysis system that is capable of operating on a small volume of dialysate.

SUMMARY OF THE INVENTION

The invention is directed to a dialysis or ultrafiltration system having a size and weight suitable to be carried or worn by a patient during a dialysis or ultrafiltration treatment. In any embodiment, a portable dialysis system has an extracorporeal circuit attachable to a portable treatment module and a urea removal module.

In any embodiment, an extracorporeal circuit has a dialyzer having a dialysis membrane, a blood inlet end for receiving blood, a blood outlet end for allowing blood out of the dialyzer, a dialysate inlet end for receiving dialysate and a dialysate outlet end for allowing dialysate out of the dialyzer, wherein the blood and the dialysate contact different sides of the dialysis membrane. Blood is circulated through the dialyzer with an extracorporeal circuit having a conduit for receiving blood from a subject and a conduit for returning blood to a subject, a blood pump for conveying blood from the subject through the extracorporeal circuit and the dialyzer, wherein blood is conveyed from the subject, to the dialyzer and back to the subject. The extracorporeal circuit is attachable to a portable treatment module or a urea removal module.

In any embodiment, a portable treatment module has a first dialysis circuit having a first sorbent cartridge for removing waste species and impurities from the dialysate, except the first sorbent cartridge does not contain urease nor does any component in the portable treatment module contain urease. One or more conduits are present for carrying dialysate between the first sorbent cartridge and the dialyzer, and a first dialysate pump is present for conveying dialysate from the first sorbent cartridge, to the dialyzer and back to the sorbent cartridge, the first sorbent cartridge having a dialysate inlet and a dialysate outlet.

In any embodiment, the first sorbent cartridge has one or more of an activated carbon and zirconium oxide.

In any embodiment, a urea removal module has a second dialysis circuit having a second sorbent cartridge for removing waste species and impurities from the dialysate, where the second sorbent cartridge contains urease. One or more conduits are present for carrying dialysate between the second sorbent cartridge and the dialyzer, and a second dialysate pump is present for conveying dialysate from the second sorbent cartridge, to the dialyzer and back to the second sorbent cartridge, the second sorbent cartridge having a dialysate input end and a dialysate output end.

In any embodiment, the urea removal cartridge includes a mixed bed anion and cation exchange resin.

In any embodiment, a first control pump controls the bi-directional movement of fluid into and out of the first or second dialysis circuits, where a flux of fluid moving between the extracorporeal circuit and the dialysis circuit is changed by the rate at which the control pump is operating, and a control reservoir stores fluid removed from the first or second dialysis circuit by the control pump or stores fluid that can be added to the first or second dialysis circuit by the first control pump.

In any embodiment, a second reservoir and a second reservoir pump are present in the system, wherein the second reservoir holds a fluid that can be added to the second dialysis circuit by operation of the second reservoir pump.

In any embodiment, the dialysis system has an infusate reservoir containing an infusate containing one or more electrolytes selected from potassium ions, calcium ions, and magnesium ions. The infusate is added to the dialysate in the urea removal module under the control of a controller in order to maintain the concentration of potassium ion, calcium ion and/or magnesium ion are maintained within predetermined ranges.

In any embodiment, a subject receives kidney replacement therapy by attaching the vasculature of the subject to an extracorporeal circuit having a first end that draws blood from the patient and a second end that returns blood to the patient. The extracorporeal circuit is attached to a portable module having a first sorbent cartridge having activated carbon and zirconium oxide, and a first dialysis circuit. Blood is conveyed from the patient through the extracorporeal circuit and a dialyzer having a dialysis membrane and, then, blood is returned to the patient. Dialysate is conveyed through the first dialysis circuit such that the dialysate moves from the first sorbent cartridge to the dialyzer and back to the first sorbent cartridge, wherein the blood and the dialysate are in fluid communication through the dialysis membrane and one or more waste species move from the blood to the dialysate. One or more waste species are removed from the blood of the patient for a first period of time wherein the one or more waste species are absorbed by the first sorbent cartridge, the first sorbent cartridge. Then, the extracorporeal circuit is attached to a urea removal module having a second sorbent cartridge having urease and a zirconium phosphate material therein and a second dialysis circuit. Dialysate is conveyed through the second dialysis circuit such that the dialysate moves from the second sorbent cartridge to the dialyzer and back to the second sorbent cartridge, wherein the blood and the dialysate are in fluid communication through the dialysis membrane and urea diffuses from the blood to the dialysate. Urea is removed from the dialysate for a second period of time wherein the urea is removed by the second sorbent cartridge.

In any embodiment, a modular system for hemodialysis treatment has an extracorporeal module including a blood pump for pumping blood from a subject through an extracorporeal circuit, the extracorporeal circuit having one or more attachments for fluidly connecting to either a portable module or to a urea removal module, and a dialyzer having a dialysis membrane where blood is conveyed from the subject to the dialyzer and back to the subject.

In any embodiment, a portable modular system for ultrafiltration has an extracorporeal circuit having a blood pump for pumping blood from a subject through the extracorporeal circuit, the extracorporeal circuit having one or more attachments for connecting to either a portable module or to a urea removal module, and a hemofilter with a hemofiltration membrane where blood is conveyed from the subject to the hemofilter and back to the subject. The one or more attachments are connected to a portable module having an ultrafiltration system, where the ultrafiltration system has a filtrate pump for applying a negative pressure to the hemofilter to cause ultrafiltrate to pass through the hemofiltration membrane.

In any embodiment, an extracorporeal module has a blood pump that pumps blood from a subject through an extracorporeal circuit, the extracorporeal circuit having one or more attachments for fluidly connecting to either a portable treatment module or to a urea removal module and wherein a flux of fluid moving between the extracorporeal circuit and either the portable module or the urea removal module is changed by the rate at which a control pump operates.

In any embodiment, a relative blood volume monitor determines the relative blood volume hydration status (RBVHS) of blood in an extracorporeal circuit, the relative blood volume monitor configured to send information to one or more controllers that control the rate of a filtrate pump or a control pump.

In any embodiment, a relative blood volume monitor determines the level of one or more solutes in the blood at a first time ($C_0$) and determines the level of the one or more solutes in the blood at a second time later than the first time ($C_t$), and the relative blood volume hydration status is calculated by the formula $RBVHS=C_0/C_t$.

In any embodiment, a relative blood volume monitor is a hematocrit sensor.

In any embodiment, a subject receives hemofiltration therapy by attaching the vasculature of a subject to an extracorporeal circuit having a first end that draws blood from the patient and a second end that returns blood to the patient. The extracorporeal circuit is attached to a portable module for ultrafiltration, the portable module having a filtrate pump. Blood is conveyed from the patient through the extracorporeal circuit and a hemofilter having a hemofiltration membrane and returning blood to the patient. The filtrate control pump is operated to separate and remove an ultrafiltrate from the blood in the extracorporeal circuit for a first period of time. Then, the extracorporeal circuit is attached to a urea removal module having a second sorbent cartridge having at least urease and zirconium phosphate or magnesium phosphate therein and a second dialysis circuit. The hemofilter has a structure to allow for operation as a dialyzer and the hemofiltration membrane having a structure to allow for operation as a dialysis membrane. Dialysate is conveyed through the second dialysis circuit such that the dialysate moves from the second sorbent cartridge to the hemofilter functioning as a dialyzer and back to the second sorbent cartridge, wherein the blood and the dialysate are in fluid communication through the hemofiltration membrane and one or more waste products diffuses from the blood to the dialysate. One or more waste products from the dialysate are removed for a second period of time wherein urea is removed by the second sorbent cartridge.

In any embodiment, a second reservoir and a second reservoir pump are present in the system, wherein the second reservoir holds a fluid that can be added to the second dialysis circuit by operation of the second reservoir pump.

In certain embodiments, a blood hydration status monitor monitors the relative blood hydration status of the subject's blood in the extracorporeal circuit.

In certain embodiments, a hematocrit detector monitors the hematocrit of the subject's blood in the extracorporeal circuit.

In certain embodiments, pulsatile pumps are not used to convey the blood or the dialysate.

In certain embodiments, enhanced convective clearance is performed utilizing the controlled compliance dialysis circuit by operating the control pump in a bidirectional manner with intermittent reversal of the direction of operation.

In any embodiment, a modular system for ultrafiltration has an extracorporeal circuit having a blood pump for pumping blood from a subject through the extracorporeal circuit, the extracorporeal circuit having one or more attachments for connecting to either a portable module or to a urea removal module, and a hemofilter with a hemofiltration membrane where blood is conveyed from the subject to the hemofilter and back to the subject. One or more attachments connect to a portable module having an ultrafiltration system, the ultrafiltration system having a filtrate pump for applying a negative pressure to the hemofilter to cause ultrafiltrate to pass through the hemofiltration membrane.

In any embodiment, a dialysis circuit is a controlled compliance dialysis circuit.

In any embodiment, a volume of fluid removed from a dialysis circuit by a control pump is substantially the same volume of fluid transferred from the body of the subject to the portable module.

In any embodiment, a first dialysis circuit has a first pathway for conveying the dialysate between a first sorbent cartridge, a first dialysate pump, and a dialyzer, and a second bypass pathway for conveying the dialysate between a dialysis outlet end of the first sorbent cartridge and a dialysis inlet end of the first sorbent cartridge without the dialysate passing through the dialyzer.

In any embodiment, a dialysate pump is a peristaltic pump.

In any embodiment, a void volume space for accommodating a dialysate in a sorbent cartridge, a dialyzer, and conduits forming a dialysis circuit has a substantially inflexible volume.

In any embodiment, one or more controllers control the operation of a control pump and the a dialysate pump, wherein one or more controllers control operation of the control pump to intermittently switch between an efflux direction to move fluid across a dialysis membrane from an extracorporeal circuit to the dialysis circuit and an influx direction to move fluid across the dialysis membrane from the dialysis circuit to the extracorporeal circuit.

In any embodiment, one or more controllers for controlling the operation of a control pump, a blood pump and a dialysate pump, wherein the one or more controllers control operation of the control pump to intermittently switch between an efflux direction to move fluid across the dialysis membrane from the extracorporeal circuit to the dialysis circuit and an influx direction to move fluid across the dialysis membrane from the dialysis circuit to the extracorporeal circuit.

In any embodiment, one or more controllers control a ratio of a rate of dialysate flow through a dialyzer and a rate of blood flow through the dialyzer to be from about 1:1.5 to about 3:1.

In any embodiment, one or more controllers control a ratio of a rate of dialysate flow through a dialyzer and a rate of blood flow through the dialyzer to be from about 1:1.5 to about 3:1.

In any embodiment, a dialysate pump operates at a rate from about 10 to about 400 mL/min.

In any embodiment, a control pump operates at a rate from about 0 to about 200 mL/min.

In any embodiment, a hematocrit sensor is an oximeter.

In any embodiment, a hematocrit sensor has a light source for emitting red or infrared light and a detector for detecting the emitted light.

In any embodiment, a relative blood volume monitor measures the velocity for ultrasonic sound waves in blood in an extracorporeal circuit.

In any embodiment, the velocity for ultrasonic sound waves indicates a level of protein concentration in blood.

In any embodiment, an impedance detector for determines a tissue fluid volume in the subject, the impedance detector configured to send information to one or more controllers that control the rate of a filtrate pump or a control pump.

In any embodiment, a relative blood volume monitor is configured to determine the fluid volume of blood at a position prior to the blood entering a hemofilter or dialyzer.

In any embodiment, one or more controllers operates a filtrate pump or a control pump to maintain a ratio of tissue fluid volume to blood fluid volume in the range from about 6:1 to about 9:1.

In any embodiment, a filtrate pump or a control pump operates at a rate from 0 to about 15 mL/min.

In any embodiment, a system for ultrafiltration does not have a sorbent for absorbing a waste species.

In any embodiment, a volume of fluid removed from a dialysis circuit by a control pump causes the same volume of fluid transferred from the body of the subject to the system.

In any embodiment, a second dialysis circuit has a bypass pathway for conveying dialysate between a dialysate outlet end of a sorbent cartridge and a dialysate inlet end of the sorbent cartridge without the dialysate passing through a dialyzer.

In any embodiment, a dialysis circuit, a urea removal module or a portable module has a conductivity meter for measuring the conductivity of dialysate in a dialysis circuit.

In any embodiment, a dialysis circuit, urea module or a portable module has a first conductivity sensor for measuring the conductivity of the dialysate at a position between a dialysate outlet end of a sorbent cartridge and the dialyzer, a second conductivity sensor for measuring the conductivity of the dialysate between a dialysate outlet end of the dialyzer and the sorbent cartridge, and one or more controllers for comparing the conductivity measured by the first conductivity sensor and the second conductivity sensor and calculating the amount of urea absorbed by the sorbent cartridge.

In any embodiment, one or more controllers signal an alert if a difference between conductivity measured by a first conductivity sensor and a second conductivity sensor are substantially equal.

In any embodiment, a sorbent cartridge contains zirconium oxide.

In any embodiment, a sorbent cartridge contains activated carbon.

In any embodiment, a sorbent cartridge further has a mixed bed deionization resin.

In any embodiment, a sorbent cartridge contains a zirconium phosphate material intermixed with a urease-containing material for removal of urea.

In any embodiment, a second control reservoir and a second reservoir pump can be provided on a dialysis circuit wherein the second control reservoir holds a fluid that can be added to the second dialysis circuit by operation of the second reservoir pump.

In any embodiment, a second control reservoir contains water, tap water or purified water.

In any embodiment, a portable module has a first sorbent cartridge containing activated carbon and zirconium oxide and optionally without urease, and a first dialysis circuit and a first dialysate pump for conveying a dialysate from the first sorbent cartridge to the dialyzer and back to the first sorbent cartridge, and a first control pump for moving fluid bi-directionally into and out of the first dialysis circuit and a first control reservoir, where a flux of fluid moving between the extracorporeal circuit and the first dialysis circuit is changed by the rate at which the first control pump operates.

In any embodiment, a urea removal module has a second sorbent cartridge containing at least urease and zirconium phosphate, a second dialysis circuit and a second dialysate pump for conveying a dialysate from the second sorbent cartridge to the dialyzer and back to the second sorbent cartridge; and a second control pump for moving fluid bi-directionally into and out of the second dialysis circuit where a flux of fluid moving between the extracorporeal circuit and the second dialysis circuit is changed by the rate at which the second control pump operates.

In any embodiment, a second sorbent cartridge contains zirconium oxide and activated carbon.

In any embodiment, the system an infusate container containing an infusate solution, the infusate solution has a potassium salt, and an infusate pump for adding the solution to the second dialysis circuit.

In any embodiment, an infusate solution has a magnesium salt and a calcium salt.

In any embodiment, the system has a bicarbonate container containing a bicarbonate solution containing a bicarbonate salt and a bicarbonate pump for adding the bicarbonate solution to the second dialysis circuit.

In any embodiment, a relative blood volume monitor to determine the relative blood volume hydration status (RBVHS) of the blood in an extracorporeal circuit, the relative blood volume monitor configured to send information to the one or more controllers.

In any embodiment, the relative blood volume monitor determines the level of one or more solutes in the blood at a first time ($C_0$) and determines the level of the one or more solutes in the blood at a second time later than the first time ($C_t$), and the relative blood volume hydration status is calculated by the formula $RBVHS=C_0/C_t$.

In any embodiment, a relative blood volume monitor is configured to determine the fluid volume of blood at a position prior to the blood entering a dialyzer.

In any embodiment, the system has an impedance detector for determining a tissue fluid volume in the subject, the impedance detector configured to send information to one or more controllers.

In any embodiment, the system is deployed with a portable module for a first period of time is about twice as long as the system is deployed by a urea removal module for a second period of time.

In any embodiment, one or more waste species are selected from the group of uremic toxins, B12, C reactive protein, and β2-microglobin and phosphates.

In any embodiment, one or more waste species are removed by means of convective clearance.

In any embodiment, an extracorporeal circuit has a blood pump for conveying blood, the first dialysis circuit further has a first dialysate pump for conveying the dialysate and the second dialysis circuit further has a second dialysate pump for conveying the dialysate, one or more of the blood pump, the first dialysate pump and the second dialysate pump are peristaltic pumps.

In any embodiment, a control pump adds fluid from a control reservoir to a first or second dialysis circuit in an influx direction via a conduit or removes fluid from the first or second dialysis circuit to the control reservoir in an efflux direction via the conduit, and intermittently switching the control pump between the efflux direction to move fluid across the dialysis membrane from the extracorporeal circuit to the first or second dialysis circuit and the influx direction to move fluid across the dialysis membrane from the first or second dialysis circuit to the extracorporeal circuit, wherein the intermittent switching of the pump accomplishes the convective clearance of at least one waste species having a molecular weight less than about 66000 g/mol and greater than about 1000 g/mol.

In any embodiment, a second reservoir pump operates to add fluid from a second control reservoir to a second dialysis circuit in an influx direction via a conduit or operating a control pump that adds fluid from a control reservoir to a second dialysis circuit in an influx direction via a conduit, and a control pump operates to remove fluid from the second dialysis circuit to the control reservoir in an efflux direction via a conduit, and the control pump intermittently switches between pumping fluid in the efflux direction to move fluid across the dialysis membrane from the extracorporeal circuit to the second dialysis circuit and the influx direction to move fluid across the dialysis membrane from the second dialysis circuit to the extracorporeal circuit, wherein the intermittent switching between pumping in the efflux and influx directions accomplishes the convective clearance of at least one waste species having a molecular weight less than about 66000 g/mol and greater than about 1000 g/mol.

In any embodiment, pumping in the efflux and influx directions is intermittently switched between the efflux direction and the influx direction at least once every minute.

In any embodiment, pumping in the efflux and influx directions is intermittently switched between the efflux direction and the influx direction such that the pump is not operated in either the efflux or influx direct for a time period exceeding about 2 minutes.

In any embodiment, pumping in the efflux and influx directions is intermittently switched between the efflux direction and the influx direction such that the pump is not operated in either the efflux or influx direct for a time period exceeding about 45 seconds.

In any embodiment, pumping in the efflux and influx directions is intermittently switched between the efflux direction and the influx direction such that the pump is not operated in either the efflux or influx direct for a time period exceeding about 30 seconds.

In any embodiment, pumping in the efflux and influx directions is intermittently switched between the efflux direction and the influx direction such that the pump is not operated in either the efflux or influx direct for a time period exceeding about 15 seconds.

In any embodiment, the control pump does not operate in the efflux direction and the influx direction for equal period of times.

In any embodiment, a control pump does not operate to pump an equal volume in the efflux direction and the influx direction over a period of time.

In any embodiment, a control pump operates to pump a larger volume in the efflux direction compared with the influx direction over a period of time.

In any embodiment, a control pump operates to pump a volume in the efflux direction that is at least about 10% greater compared to a volume pumped in the influx direction over a period of time.

In any embodiment, a control pump operates to pump a volume in the efflux direction that is at least about 20% greater compared to a volume pumped in the influx direction over a period of time.

In any embodiment, a control pump operates to pump a volume in the efflux direction that is at least about 30% greater compared to a volume pumped in the influx direction over a period of time.

In any embodiment, a first sorbent cartridge removes one or more impurity species from the dialysate.

In any embodiment, a second sorbent cartridge removes one or more impurity species from the dialysate.

In any embodiment, a second reservoir pump adds fluid from a second control reservoir to the second dialysis circuit.

In any embodiment, a second control reservoir contains water, tap water or purified water.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE INVENTION

Figure 1:
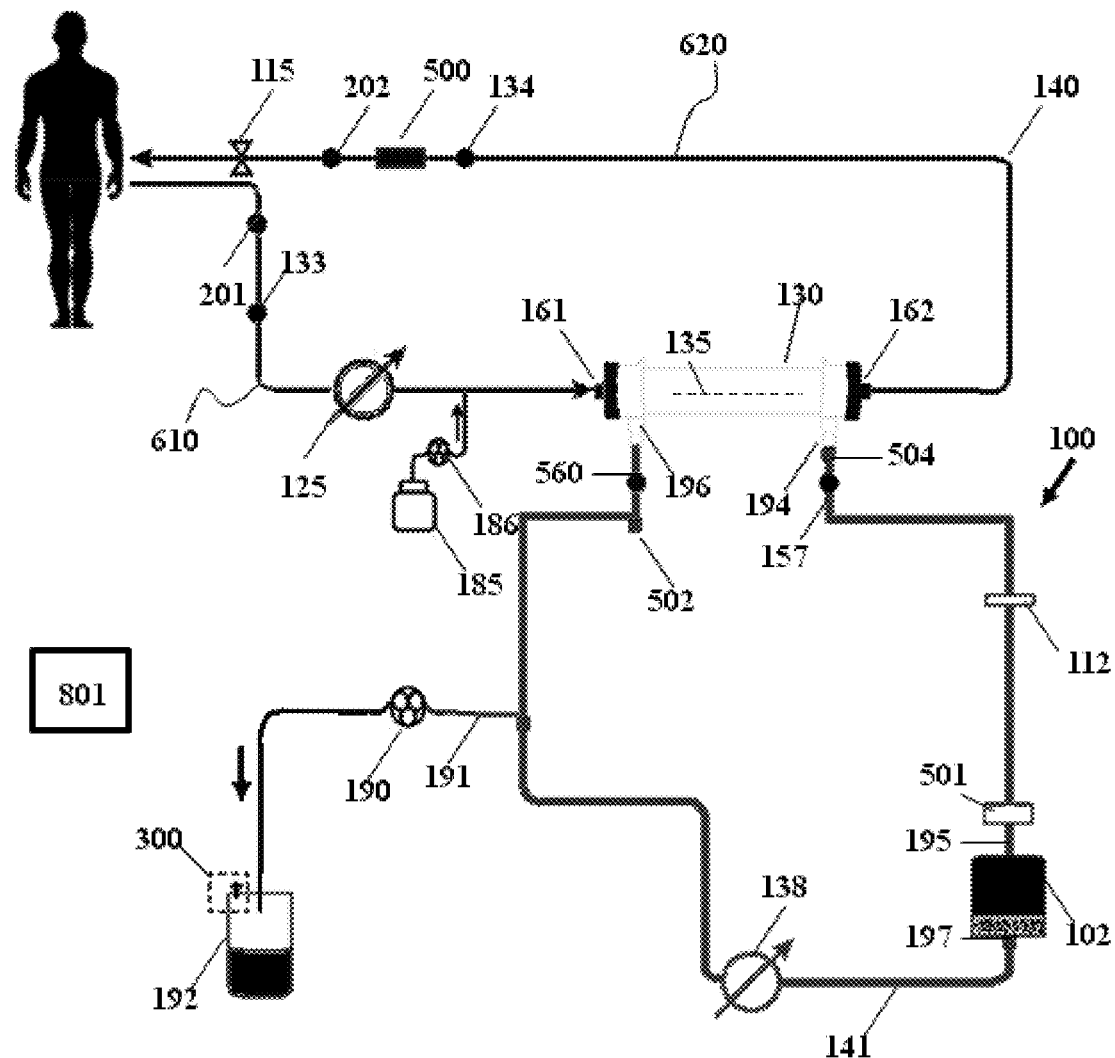
FIG. 1 shows a hemodialysis device having an extracorporeal circuit, dialyzer, and a portable treatment module having a controlled compliant dialysis circuit operating in accordance with certain embodiments.

The present invention provides for more frequent removal of accumulated fluid in individuals with End Stage Renal Disease (ESRD). Subjects with ESRD have a reduced ability to eliminate excess fluid from the body leading to a significant degree of fluid retention in body tissues. However, the volume of the blood does not vary by a significant amount from the approximately 5 L volumes for adult humans. Excess fluid can be removed from the body by ultrafiltration of the blood by the present invention. The rate at which fluid can be removed from body tissues by ultrafiltration is limited due to the lag time for replacement or migration of fluid from the body compartment containing the body tissue fluid to the blood. Hence, removal of excess body tissue fluid requires a relatively low rate of ultrafiltration for net fluid removal over an extended period of time. The present invention provides for performing ultrafiltration for fluid removal on a more frequent basis than treatments to remove urea from the blood.

Methods and systems are also disclosed for performance of hemodialysis with a portable treatment module for removing one or more non-urea waste products from a subject. The portable treatment module does not require the dialysate used therein to undergo continuing monitoring and adjustment of such properties as pH, conductivity and electrolyte content. Due to the lack of a requirement for components to control for pH, conductivity and electrolyte content, the portable device is more readily adaptable to use a low volume of dialysate, have low weight and to be less conspicuous when carried or worn by an individual. The portable treatment module is readily adapted for extended treatment regimes without unduly limiting the mobility of a subject. The portable treatment module includes an extracorporeal circuit for circulating blood for contact with a dialysis membrane. The extracorporeal circuit can be attached to a urea removal module for the periodic removal of urea from the blood.

In alternate embodiments, methods and systems can perform ultrafiltration with a portable treatment module for removing accumulated fluid from a subject. Fluid removed as ultrafiltrate can be stored for disposal and is not otherwise introduced to the subject or contacted with the subject's blood. In certain embodiments, systems are not required for monitoring and adjusting properties such as pH, conductivity and electrolyte content, which is normally required for hemodialysis treatment employing sorbents for dialysate regeneration. Due to the reduction in components required for the portable treatment module, the portable treatment module can allow for frequent or near-continuous removal of fluid by ultrafiltration thereby mimicking natural kidney function without unduly limiting mobility. The urea removal module described above can be occasionally employed to remove waste products from the blood.

Further disclosed is a dialysis system having a controlled compliance dialysis circuit. Some home-use systems employ a reservoir of working dialysis solution that varies in volume depending upon bulk movement of water across the dialysis membrane and/or water added to dilute sodium ion concentration and reduce conductivity generated during treatment. However, such systems complicate accurate control over removal of fluid from a patient through techniques such as ultrafiltration and diafiltration that are commonly employed to address fluid build-up in patients while simultaneously removing waste products from the blood. In this disclosure, a controlled compliance dialysis circuit is provided for conveying and re-circulating a dialysate in conjunction with accurate removal of the fluid volume from the patient during ultrafiltration and diafiltration. The dialysate flow path described herein has active control of fluid flow entering and exiting the flow path in a manner that allows for the accurate performance of ultrafiltration, the quantization of urea removal and the performance of convective clearance of mid-weight uremic waste species without an excessive risk for blood clotting.

It is to be understood by one skilled in the art that hemodialysis can include hemodialysis, hemofiltration, and hemodiafiltration. Dialysis as a renal or kidney replacement therapy, which can include hemodialysis, hemodiafiltration, or hemofiltration, to remove toxins and waste species from a subject's blood. Further, a treatment that performs a baseline rate of ultrafiltration can be useful to address fluid accumulation between treatment sessions for the removal of waste species.

Definitions

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "activated carbon" refers to a porous carbon material having a surface area greater than 500 $m^2$ per gram. Activated carbon can be capable of absorbing several species including heavy metals such as lead, mercury, arsenic, cadmium, chromium and thallium among others, oxidants such as chlorine and chloramine, fluoride ions, and waste species such as phosphate and certain nitrogen-containing waste species such as creatinine and uric acid.

The terms "administering," "administer," "delivering," "deliver," "introducing," "bolus," and "introduce" can be used interchangeably to indicate the introduction of water or an agent, including electrolytes and alkali and/or alkali earth ions, to a patient in need thereof, and can further mean the introduction of water, any agent or alkali and/or alkali earth ions to a dialysate or dialysis circuit where such water, agent or alkali and/or alkali earth ion will enter the blood of the patient by diffusion, transversal of a diffusion membrane, or other means.

The term "air trap" refers to a structure for separating a gas from a mixture of a gas and a liquid. An air trap can include a hydrophobic membrane for allowing gases to pass and preventing the passage of water.

The term "anticoagulant" is a substance that prevents or delays the clotting of blood, such as heparin, fragmin, and sodium citrate.

A "biocompatible material" is a material that has the ability to interface with living biological tissues with an acceptable host response in any of specific medical systems, methods of treatment or delivery contemplated herein. The biocompatible material can consist of synthetic, natural or modified natural polymers intended to contact or interact with the biological systems during application of any of the inventions contained herein.

The term "calcium exchange resin" refers to a material that is competent to perform cation exchange by releasing calcium ions into a solution in contact with the calcium exchange resin and absorbing other cations from the solution.

The term "conduit" refers to a vessel or passageway having a void volume through which a fluid can travel or move. A conduit can have a dimension parallel to the direction of travel of the fluid that is significantly longer than a dimension orthogonal to the direction of travel of the fluid.

"Chronic Kidney Disease" (CKD) is a condition characterized by the slow loss of kidney function over time. The most common causes of CKD are high blood pressure, diabetes, heart disease, and diseases that cause inflammation in the kidneys. Chronic Kidney Disease can also be caused by infections or urinary blockages. If CKD progresses, it can lead to end-stage renal disease (ESRD), where the kidneys fail to function at a sufficient level.

The terms "communicate" and "communication" include, but are not limited to, the connection of system electrical elements, either directly or remotely, for data transmission among and between said elements. The terms also include, but are not limited, to the connection of system fluid elements enabling fluid interface among and between said elements.

The term "comprising" includes, but is not limited to, whatever follows the word "comprising." Thus, use of the term indicates that the listed elements are required or mandatory but that other elements are optional and may or may not be present.

The term "conductivity meter" or "conductivity sensor" refers to a device for measuring the electrical conductance of a solution.

The term "consisting of" includes and is limited to whatever follows the phrase "consisting of:" Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "control pump" refers to a pump that is operable to pump fluid bi-directionally to actively control the transfer of fluid volume into or out of a compartment or circuit.

The term "control reservoir" refers to a substantially inflexible or optionally a flexible vessel or container accessible by the control pump that contains a variable amount of fluid.

A "control system" consists of combinations of components that act together to maintain a system to a desired set of performance specifications. The control system can use processors, memory and computer components configured to interoperate to maintain the desired performance specifications. It can also include fluid control components, and solute control components as known within the art to maintain the performance specifications.

A "controller," "control unit," "processor," or "microprocessor" is a device which monitors and affects the operational conditions of a given system. The operational conditions are typically referred to as output variables of the system, which can be affected by adjusting certain input variables.

The terms "controlled compliance" and "controlled compliant" describe the ability to actively control the transfer of fluid volume into or out of a compartment or circuit. In certain embodiments, the variable volume of fluid in a dialysate circuit expands and contracts via the control of one or more pumps. The volume of fluid in the system minus the attached reservoirs once the system is in operation is generally constant. The attached reservoirs allow the system to adjust the patient fluid volume by withdrawing fluid and storing the desired amount in an attached control reservoir and/or by providing rebalanced fluids to the patient and removing waste products. Alternatively, the fluid stored in a control reservoir attached to the dialysate circuit, which can be used for ultrafiltration (UF) and/or delivery of an infusate. The terms "controlled compliance" and "controlled compliant" are not to be confused with the term "non-compliant volume," which simply refers to a vessel, conduit, container, pathway or cartridge that resists the introduction of a volume of fluid after air has been removed from a defined space such as a vessel, conduit, container, pathway or cartridge.

The term "convective clearance" refers to the movement of solute molecules or ions across a semi-permeable barrier due to force created by solvent molecules moving across the semi-permeable barrier.

The term "dialysate" describes a fluid into which solutes from a fluid to be dialyzed diffuse through a membrane. A dialysate typically contains electrolytes that are close in concentration to the physiological concentration of electrolytes found in blood.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The term "dialysis membrane" and "hemofiltration membrane can refer to a semi-permeable barrier selective to allow diffusion of solutes of a specific range of molecular weights through the barrier, or optionally a high-permeability or high-flux membrane, which is a type of semipermeable membrane that is more permeable to water than the semipermeable membrane of a conventional hemodialysis system, which has a semipermeable membrane that has a sufficiently low permeability to water such that an ultrafiltration controller is not required to prevent excessive loss of water from the patient's blood. During high permeability hemodialysis, the system removes toxins or excess fluid from the patient's blood using the principles of convection (via a high ultrafiltration rate) and/or diffusion (via a concentration gradient in dialysate). In certain non-limiting examples, the semipermeable membrane during high permeability hemodialysis has an in vitro ultrafiltration coefficient (Kuf) greater than 8 milliliters per hour per conventional millimeter of mercury, as measured with bovine or expired human blood.

The term "diluent" refers to a fluid having conductivity less than a fluid to which the diluent is added.

The term "electrolyte" refers to an alkali or alkali earth cation dissolved in an aqueous medium.

The term "filtration" refers to a process of separating solutes from a fluid, by passing the fluid through a filter medium across which certain solutes or suspensions cannot pass. Filtration is driven by the pressure difference across the membrane.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Those skilled in the art will recognize that a minimal amount of expansion or contraction of the vessel or container can occur in a substantially inflexible volume; however, the addition or subtraction of a significant volume of fluid over a maximum or minimum will be resisted.

The term "fluid communication" refers to at least two fluids that are contained in separated compartments that are able to exchange matter, either solvent or solute molecules or ions, through a semi-permeable barrier.

The terms "frit" and "spacer frit" refer to a material that is biocompatible and has a porosity between about 1 μm and 300 μm. The material can be one or more of biocompatible, compressible, an open cell polymer or foam or similar material.

"Hemofiltration" is a therapy in which blood is filtered across a semi-permeable membrane. Water and solutes are removed from the blood via pressure-driven convection across the membrane. In hemofiltration, solutes small enough to pass through the membrane in proportion to their plasma concentration are removed. The driving force is a pressure gradient rather than a concentration gradient. A positive hydrostatic pressure drives water and solutes across the filter membrane from the blood compartment to the filtrate compartment, from which it is drained. Solutes, both small and large, get dragged through the membrane at a similar rate by the flow of water that has been engineered by the hydrostatic pressure. Hence, convection overcomes the reduced removal rate of larger solutes (due to their slow speed of diffusion) seen in hemodialysis. The rate of solute removal is proportional to the amount of fluid removed from the blood circuit, which can be adjusted to meet the needs of a clinical situation. In general, the removal of large amounts of plasma water from the patient requires volume substitution. Substitution fluid, typically a buffered solution close to the plasma water composition a patient needs, can be administered pre or post filter (pre-dilution mode, post-dilution mode).

"Hemodialysis" is a technique where blood and a "cleansing fluid" called dialysate are exposed to each other separated by a semi-permeable membrane. Solutes within the permeability range of the membrane pass while diffusing along existing concentration gradients. The dialysate employed during hemodialysis has soluble ions such as sodium, calcium and potassium ions and is not pure water. The sieving properties of the membrane exclude all solutes above a certain threshold from crossing the membrane. One common sieving property is "albumin sieving." In most situations, it is not desirable to remove Albumin during renal replacement therapy, as lower blood serum Albumin is associated with increased mortality rates. The term "albumin sieving coefficient" can be used to describe the amount of albumin that will cross the membrane.

The term "hematocrit" refers to the fraction of blood volume occupied by erythrocytes.

"Hemodiafiltration" is a therapy that combines hemofiltration and hemodialysis.

The term "impedance meter" refers to a device for measuring the opposition of an object or structure to an alternating current.

The term "infusate container" refers to a vessel, which can be a substantially inflexible or flexible vessel, for holding a solution of one or more salts for the adjustment of the composition of a dialysate.

The term "infusate solution" refers to a solution of one or more salts for the adjustment of the composition of a dialysate, such as salts of calcium, magnesium and potassium.

The term "impurity species" refers to a molecular or ionic species that originates from tap water, a sorbent cartridge or a source other than a patient's or subject's blood including chlorine, fluoride ions, and aluminum-containing species.

The term "waste species" or "waste products" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system. For example, nitrogen-containing waste products are generally at a level less than 30 mg/dL in the blood for individuals with a healthy renal system and inorganic phosphate is generally at range between 2.5-4.5 mg/dL. The level of waste products in the blood is elevated for individuals with impaired kidney function.

The term "nitrogenous waste" refers to any non-polymeric nitrogen-containing organic compound originating from the blood of a patient. Nitrogenous waste includes urea, and creatinine.

The term "non-compliant volume" refers to a vessel, conduit, container, pathway or cartridge that resists the introduction of a volume of fluid after air has been removed from a defined space such as a vessel, conduit, container, pathway or cartridge.

The term "oximeter" refers to a device for measuring the amount of oxygen carried by a volume of blood.

The term "luer connector" or "luer adapter" refers to adapters or connector conforming with International Standards Organization (ISO) standards 594-2.

The term "memory" refers to a device for recording digital information that can be accessed by a microprocessor, such as RAM, Dynamic RAM, microprocessor cache, FLASH memory, or memory card.

The term "mid-weight uremic wastes" refers to substances that can pass through a dialysis membrane and that have a molecular weight less than about 66000 g/mol and greater than about 1000 g/mol.

The term "moving fluid bi-directionally" refers to the ability to move a fluid across a barrier, such as a semipermeable membrane, in either direction through the thickness of the barrier.

"Osmolarity" is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

A "patient" or "subject" is a member of any animal species, preferably a mammalian species, optionally a human. The subject can be an apparently healthy individual, an individual suffering from a disease, or an individual being treated for a disease.

The terms "pathway" and "conveyance pathway" refer to the route through which a fluid, such as dialysate or blood, travels.

The term "peristaltic pump" refers to a pump that operates by compression of a flexible conduit or tube through which the fluid to be pumped passes.

The terms "portable system" or "wearable system" refers to a system in whole or in part having a mass and dimensions to allow for transport by a single individual by carrying the system or wearing the system on the individual's body.

The terms "pressure differential" and "pressure drop" refer to the difference in pressure measurements of a fluid between two points of measurement.

The term "pressure meter" refers to a device for measuring the pressure of a gas or liquid in a vessel or container.

The terms "processor," "computer processor," and "microprocessor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture and being capable of carrying out a set of commands, automatically that can be changed or replaced.

The term "pulsatile pump" refers to a pump that mimics the action of a mammalian heart where the pumped fluid undergoes periodic variation in velocity.

The term "pump" refers to a device that causes the movement of fluids or gases by the application of suction or pressure.

The term "quick connector" refers to any structure for making an attachment that is operable by an individual using their hands or fingers without the assistance of additional tools.

The term "relative blood volume monitor" refers to any device measuring the concentration of any solute or solid material in the blood. Non-limiting examples of relative blood volume monitors include devices for measuring the concentration of oxyhemoglobin, deoxyhemoglobin, hematocrit or red blood cell count, osmolarity or total protein concentration of the blood.

The term "relative blood volume hydration status" refers to the relative change in the level of any target solute or solid material in the blood over a period of time. Non-limiting examples of target solute or solid materials include oxyhemoglobin, deoxyhemoglobin, hematocrit or red blood cell count, osmolarity or total protein concentration of the blood. Relative blood volume hydration status can be monitored by observation of a change in a signal responsive to the level of any target solute or solid material in the blood without a requirement that the absolute concentration of the target solute or solid material be determined.

The term "spent dialysate" refers to a dialysate that has been contacted with blood through a dialysis membrane and contains one or more impurity, or waste species or waste substance, such as urea. The quick connector can have a valve that shuts off flow when the connector is disconnected.

The term "sorbent cartridge" refers to a cartridge containing one or more sorbent materials for removing specific solutes from solution, such as urea.

The terms "treating" and "treatment" refer to the management and care of a patient having a pathology or condition by administration of one or more therapies contemplated by the present invention. Treating also includes administering one or more methods of the present invention or using any of the systems, devices, or compositions of the present invention in the treatment of a patient. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution if the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in either a dialysis, hemodiafiltration or filtration process.

The term "void volume" refers to a specific volume that can be occupied by a fluid in a defined space such as a dialysate circuit of the invention including all components contained therein.

"Diffusive permeability" is a property of a membrane describing permeation by diffusion. Diffusion is the process of solutes moving from an area of higher concentration to an area of lower concentration The term "porosity," as used herein describes the fraction of open pore volume of a membrane.

The term "shunt," as used herein describes a passage between channels, such as blood vessels, where the shunt diverts or permits flow from one pathway or region to another.

The term "plumbing," as used herein generally describes any system of valves, conduits, channels, and lines for supplying any of the fluids used in the invention.

The term "extracorporeal," as used herein means situated or occurring outside the body.

The term "effluent dialysate," as used herein describes the discharge or outflow after the dialysate has been used for dialysis.

The term "metabolic waste species," as used herein describes organic and inorganic components generated by a patient. They can be metabolic products such as urea, uric acid, creatinine, chlorides, inorganic sulfate and phosphate, or excess electrolytes such as sodium, potassium, etc. It will be understood that the specific "metabolic waste species" can vary between individuals depending on diet and environmental factors. Hence, the term is intended to encompass any waste component that is normally removed by a kidney or by dialysis without restriction on the specific type of waste substance.

The term "working dialysate solution" refers to a dialysate solution that is undergoing circulation or active movement through a system including conduits, pathways, dialyzers and cartridges.

Modular Hemodialysis System

Dialysis membranes employed in dialysis treatment are typically only selective toward molecular weight. Urea, ions and other small molecules can move across the dialysis membrane unimpeded from a higher concentration to a lower concentration and thereby lower the concentration of such species in the patient's blood. Waste species entering the dialysate are removed by a sorbent cartridge before the dialysate is reused for dialysis. Although urea is the main waste product of nitrogen metabolism, urea is not the sole waste species whose homeostasis is affected by the decreased clearance rates associated with kidney disease. All waste products that are cleared by the kidneys are susceptible to buildup to unsafe levels in individuals having kidney disease. In particular, mid-weight uremic waste species and phosphates buildup in the blood and bodies of individuals with kidney disease. Individuals receiving traditional hemodialysis treatment still experience high levels of morbidity and death, which may be evidence that traditional hemodialysis therapy is not a completely adequate substitute with the continual blood-clearing function of healthy kidneys.

Urea is readily removed from the blood by hemodialysis and is not known to build up in significant quantities in other areas of the body. However, other waste products are not so readily removed from the body and may build up in the body in areas not readily accessible by hemodialysis. In particular, kidney failure reduces the ability to clear phosphates from the blood and results in an increase in parathyroid hormone levels. The skeletal system is the major site of storage of both calcium and phosphates in the body, where a disruption in phosphate homeostasis also has a tendency to affect calcium levels in the blood. Patients receiving kidney dialysis frequently take phosphate binder drugs to prevent the absorption of phosphates from the diet. Buildup of non-urea waste materials may be one source of increased morbidity in patients receiving kidney dialysis. Moreover, non-urea waste species such as phosphates readily diffuse from the blood into the dialysate through common dialysis membranes. The majority of phosphate buildup in individuals with kidney failure may occur in the intracellular space in the body. Phosphates must move from the intracellular space to the blood to be removable by hemodialysis. Longer hemodialysis treatments can therefore be effective in better controlling phosphate levels; however, the length of time that a patient will be required to be immobile to complete longer therapeutic regimes can be impractical. Mid-weight uremic waste species are also susceptible to build-up outside of the circulation limiting the effectiveness of hemodialysis treatment.

In the present invention, the circulatory system is accessed through an extracorporeal circuit. The extracorporeal circuit acts as an extension of the subject's circulatory system. Thus, fluid can be extracted from blood passing through the extracorporeal circuit to ultrafiltrate or fluid can be added to the extracorporeal circuit to hydrate the subject. The extracorporeal circuit functions to attach to the vasculature of the subject, convey blood through a dialyzer housing a dialysis membrane, and return the blood to the patient in a continuous loop. Blood is conveyed by means of a blood pump.

The extracorporeal circuit is attachable to a portable treatment module having a dialysis circuit in certain embodiments. The dialysis circuit functions by conveying a dialysate having a physiological compatible composition through the dialyzer attached to the extracorporeal circuit. The dialysis circuit has a substantially inflexible volume and contains a predetermined volume of dialysate therein. Dialysate is conveyed from the dialyzer, where waste products are transferred from the blood, to a sorbent cartridge and back to the dialyzer in a continuous loop. The dialysis circuit can optionally have a control pump for moving fluid to or from the dialysis circuit. Due to the substantially inflexible volume of the dialysis circuit, the dialysis circuit functions as a controlled compliant dialysis circuit to control the movement of bulk fluid across the dialysis membrane, as will be described below in greater detail.

The sorbent cartridge of the portable treatment module contains at least an activated carbon material suitable for absorbing uremic waste species and creatinine present in the dialysate. Optionally, the sorbent cartridge can further contain a zirconium oxide material competent to absorb phosphates from the dialysate. The sorbent cartridge does not contain a urease enzyme or another material that converts urea into a different chemical form. Due to the small volume of the circulating dialysate, the concentration of urea quickly equilibrates between the blood and the dialysate, where the urea concentration in the dialysate is not substantially affected by the sorbent materials in the sorbent cartridge. However, the presence of urea in the dialysate does not pose a safety risk insofar as the concentration of urea in the dialysate reflects the typical range of the urea present in the blood between urea removal treatments using existing treatment modalities.

While urea is not removed by the portable treatment module, uremic waste species and, optionally, phosphates are removed by the portable treatment module. As will be described below, convective clearance can also be performed to remove mid-weight uremic waste species as well as ultrafiltration to remove excess fluid. Unlike the action of urease in combination with zirconium phosphate, the activated carbon and/or zirconium oxide can remove uremic waste species and phosphates without increasing the conductivity of the dialysate, adversely affecting the pH of the dialysate or removing $Ca^{2+}$, $Mg^{2+}$ or $K^+$ from the dialysate. Specific control systems for conductivity (sodium concentration), bicarbonate ion infusion or cation infusion are not needed to maintain the dialysate in a physiological compatible condition. Further, an air trap is not needed to remove carbon dioxide generated by the activity of urease, although an air trap can be included.

Standard hemodialysis treatment uses four-hour sessions that are directed to accomplish the removal of urea, phosphates, fluid removal (hemofiltration or hemodiafiltration) and uremic waste materials. Using the portable treatment module described herein, all of the functions, except for urea removal, can be accomplished using a portable or wearable system that can operate for an extended period of time while the subject is ambulatory. On a periodic basis, the extracorporeal circuit is attachable to a urea removal module that is not necessarily designed to be portable. The urea removal module contains a dialysis circuit having a sorbent cartridge designed to remove urea. Accordingly, the urea removal module contains components for the adjustment of pH and/or conductivity and for infusion of cations. Since the urea removal module is only used for the removal of urea, the subject only needs to be connected with the urea removal module periodically. Further, significant reduction in blood urea concentration can be achieved in less than a traditional three- or four-hour session. Therefore, the amount of time that the subject is attached to the urea removal module can be limited. Specifically, the urea removal module only needs to be used for a time sufficient to remove urea, where other treatment functions such as hemofiltration can be performed by the portable treatment module. In certain embodiments, a subject is attached to the urea removal module for a total time that does not exceed more than about three hours in any 24-hour period. In certain further embodiments, a subject is attached to the urea removal module for a total time that does not exceed more than about two hours in any 24-hour period. In still other embodiments, a subject is attached to the urea removal module for a total time that does not exceed more than about 90 minutes in any 24-hour period. In still other embodiments, a subject is attached to a urea module two or three days a week for one to three hours. In certain embodiments, the average blood urea nitrogen (BUN) of a subject is maintained to be less than about 30 mg/dL through use of the urea removal module that does not exceed one of the preceding time guidelines. In certain embodiments, the average blood urea nitrogen (BUN) of a subject is maintained to be less than about 20 mg/dL through use of the urea removal module that does not exceed one of the preceding time guidelines.

In some embodiments, the portable treatment module can be configured to perform ultrafiltration for an extended period of time. As described above, an extracorporeal circuit is configured to access a subject's vasculature and circulate the subject's blood therein, where the extracorporeal circuit includes a hemofilter. A control pump is attached to the hemofilter to draw fluid (i.e. an ultrafiltrate) from the subject's blood and into a storage container. Ultrafiltrate can be generated at a rate to allow for replacement of the volume of the removed ultrafiltrate by migration of fluid from body tissues to the blood. The volume of body fluid can be reduced over time. As described above, the extracorporeal circuit is attachable to the urea removal module for a periodic treatment to remove waste products from the blood.

In certain embodiments, a subject is attached to the urea removal module for a total time that does not exceed more than about 10 hours in any one week period. In certain further embodiments, a subject is attached to the urea removal module for a total time that does not exceed more than about 8 hours in any one week hour period. In certain additional embodiments, a subject is attached to the urea removal module for a total time that does not exceed more than about 6 hours in any one week period. In certain embodiments, the average blood urea nitrogen (BUN) of a subject is maintained to be less than about 30 mg/dL through use of the urea removal module that does not exceed one of the preceding times. In certain embodiments, the average blood urea nitrogen (BUN) of a subject is maintained to be less than about 20 mg/dL through use of the urea removal module that does not exceed one of the preceding times.

Portable Treatment Module for Hemodialysis

FIG. 1 shows a hemodialysis system for circulating blood and a dialysate through a dialyzer 130 using the portable treatment module 100. A shunt, such as a needle or catheter, is connected to a subject's vasculature to draw blood and circulate the patient's blood through an extracorporeal circuit 140. The portion of the extracorporeal circuit 140 that contains drawn blood from the patient is referred to as the arterial line 610, which by convention is understood to mean a line for transporting blood from the patient regardless of whether blood is drawn from an artery or vein of the patient. Similarly, the portion of the extracorporeal circuit 140 that returns blood to the patient is referred to as venous line 620. Arterial line 610 conveys blood to the dialyzer 130. Venous line 620 returns blood from the dialyzer 130 to the patient. In certain embodiments, the arterial line 610 and the venous line 620 connect with one or more veins of the patient. Locomotive power for moving the blood through the extracorporeal circuit 140 is provided by a blood pump 125, which is typically located along the arterial 610 line. Blood is typically conveyed through the extracorporeal circuit 140 at a rate of 50 to 600 mL/min and can be adjusted by a controller 801 to any required rate suitable for hemodialysis.

Blood pump 125 can be a peristaltic pump, although those skilled in the art will readily understand that other types of pumps can be used, including diaphragm pumps, centrifugal pumps, and shuttle pumps. In certain embodiments, blood pump 125 is not a pulsatile pump. In certain embodiments, the blood pump 125 conveys blood through the dialyzer 130 where the blood is contacted with a blood side of a high permeability dialysis membrane 135. Blood enters the dialyzer 130 through a blood inlet 161 and exits through a blood outlet 162. The pressure of the blood prior to the dialyzer 130 is measured by a pressure meter 133 and post dialyzer 130 by a pressure meter 134. The pressure at pressure meter 133 gives an indication of the adequacy of the blood flow into the circuit, increased vacuum is an indication of a less adequate access flow. The pressure indication at pressure meter 134 indicates obstructions in the venous bloodline. An air trap 500 is placed along the extracorporeal circuit 140 to prevent the introduction of air into the circulatory system of the patient. The air trap 500 is not limited to a particular design. Typical air traps employ a hydrophobic membrane that allows air to be separated from an air-liquid mixture by allowing air to pass through the membrane and retaining water-based fluids. Alternatively the air trap 500 can be run full, where a pressure meter can uses a flexible impermeable membrane to transmit pressure pulses to a pressure transducer such that there is no direct air blood interface. Air-fluid detectors 201 and 202 can optionally be present to confirm that air is not present in the extracorporeal circuit 140. Air-fluid detectors 201 and 202 can be ultrasonic sensors that can detect a change in solution density or scattering due the presence of air or air bubbles. A valve 115 can be present to control access to the subject's vascular system.

During the course of conveyance of blood along the extracorporeal circuit 140, heparin or a similar anticoagulant is added to the blood to prevent clotting of blood within the dialyzer 130 or any of the conduits forming the blood conveyance pathway/extracorporeal circuit 140. Heparin or another anticoagulant is added from an anticoagulant container 185 at a metered rate using an anticoagulant pump 186. The anticoagulant pump 186 can be any pump capable of accurately metering heparin. Alternatively, a surface of the extracorporeal circuit 140 can be covalently bound to heparin or a like anticoagulant.

Dialysate within the system is conveyed through one or more conduits forming a dialysis circuit 141 through use of a dialysate pump 138. Dialysate that is conveyed through the dialyzer 130 on the dialysate side of the dialysis membrane 135 picks up waste from the blood, including urea, by diffusion or convection. The dialysate is conveyed through a sorbent cartridge 102 to remove waste products before being re-conveyed through the dialyzer 130. The dialysate enters the sorbent cartridge 102 at a dialysate inlet end 197 and exits at an outlet end 195. An air trap 501 can be positioned before or after outlet end 195 to remove gasses introduced into the dialysate by the sorbent cartridge 102. Optionally, the dialysate can be passed through a microbial filter 112. Blood leaks across the dialysis membrane 135 can be detected by a blood leak detector 560. The blood leak detector 560 can be an optical detector having a light source and photo detector allowing for the observation of a red color in the dialysate. The volume of actively circulating dialysate is determined by the total void volume of the conduits and the sorbent cartridge 102 forming the dialysis circuit 141. The void volumes of the conduits and of the sorbent cartridge 102 forming the dialysis circuit 141 have an un-expandable or substantially inflexible volume. A pressure detector 157 can be present along the dialysis circuit 141 to monitor the pressure of the circulating dialysate.

The sorbent cartridge contains an activated carbon material for the removal of one or more waste products that has entered the dialysate from the blood. The activated carbon material has a surface area for adsorption of a wide range of impurities including metal ions and uremic toxins, such as uremic toxins, B12, C reactive protein, and β2-microglobin. Activated carbon absorbs materials without exchanging other ions or molecules into the dialysate. Filtering the dialysate through the activated carbon material does not modify the pH or composition of the dialysate other than through the absorption of waste materials. Optionally, the sorbent cartridge can further contain a zirconium oxide material. Zirconium oxide is an anion exchange material that functions by exchanging phosphate for acetate and bicarbonate. The zirconium oxide material does not significantly modify the composition and/or pH of the dialysate. However, the acetate released by the zirconium oxide is generally not hazardous and does not require removal from the dialysate. Acetate will freely diffuse across the dialysis membrane 135 to enter the subject's circulation, where the acetate will be converted to bicarbonate in the subject's liver. The endogenous buffer system of blood is based upon bicarbonate, wherein the exchange of bicarbonate by the zirconium oxide material does not adversely affect blood pH. The addition of bicarbonate ions to the dialysate tends to maintain the dialysate at a physiologically acceptable pH.

Due to the sorbent materials present in the sorbent cartridge 102, the dialysate does not require any chemical adjustments during operation. Specifically, the dialysate will quickly come into equilibrium with all species that are capable of diffusing across the dialysis membrane 135. Specifically, the sodium ion concentration, potassium ion concentration, calcium ion concentration, magnesium ion concentration, urea concentration and bicarbonate buffer components will be substantially the same between the dialysate and the subject's blood during treatment. However, the concentration of uremic toxins and, optionally, phosphate in the dialysate will be at a lower concentration relative to the subject's blood. Hence, a diffusion gradient will be maintained for the uremic toxins and/or phosphates during treatment.

The extracorporeal circuit 140 and/or dialyzer 130 can be contained in a housing that allows access to at least dialysate outlet 196 and dialysate inlet port 194 of the dialyzer 130. The dialysate outlet 196 and dialysate inlet port 194 can be either directly exposed on the surface of the housing or attached to conduits having an end accessible to a user. A pair of connectors or quick connectors 502 couples the outlet port 196 of the dialyzer 130 to the dialysis circuit 141 of the portable treatment module 100, and a separate set of connectors or quick connectors 504 connects the inlet port 194 to the dialysis circuit 141. The dialysis circuit 141 can also be contained in a housing, wherein a conduit leading to the inlet 197 of the sorbent cartridge 102 has an end accessible by a user and having half of the pair of connectors or quick connectors 502. Similarly, a conduit leading to the outlet 195 of the sorbent cartridge 102 has an end accessible by a user and having half of the pair of connectors or quick connectors 504. Optionally, a detector, such as a pressure switch-type detector, a magnetic switch, or an optical detector, can be present to determine the connection state of any connector described herein.

Controlled Compliant Properties and Ultrafiltration

As discussed, the dialysis circuit 141 has a substantially inflexible or controlled compliant volume, where the conduits and the sorbent cartridge 102 have substantially inflexible volumes. The substantially inflexible volume nature of the dialysis circuit 141 can be used to form a controlled compliance circuit allowing for accurate control of the movement of fluid across the dialysis membrane 135. The controlled compliance circuit operates by employing two principal components: 1) an extracorporeal circuit that is attached to the vasculature and the circulation of a patient, and 2) a dialysis circuit having a substantially inflexible void volume for the circulation of a dialysate. The extracorporeal circuit is an extension of the subject's circulatory system external to the subject's body. Any fluid added to the dialysis circuit 141 will enter the subject's body; likewise, any fluid drawn out of the extracorporeal circuit 140 originates from the subject's body. Due to the connection between the extracorporeal circuit 140 and the vascular system, there is freedom of movement for fluid to flow into and out of the extracorporeal circuit due to the relatively large volume of the patient's body to accommodate an influx of fluid or to serve as a reservoir for fluid. As will be described in greater detail below, a control pump 190, as shown in FIG. 1, is employed to actively control fluid movement between the extracorporeal circuit 140 and the dialysis circuit 141. The control pump 190 accesses the dialysis circuit 141 through a conduit 191. The controlled compliance dialysis circuit also simplifies the entire system. Specifically, scales or gravimetric methods are not required to balance fluid removal with fluid replacement.

The total void volume of the conduits having a substantially inflexible volume prevents the passive inflow and outflow of fluid volume due to pressure changes that can occur over the course of treatment. This is advantageous because not all pressure changes during treatment are under precise control by a user or operator. A controlled compliance dialysis circuit is achieved by actively controlling the inflow (influx) and outflow (efflux) of fluid to and from the dialysis circuit 141 and the extracorporeal circuit 140. In this manner, the volume of fluid crossing the dialysate membrane 135 is under direct control and can be accurately determined. In certain embodiments, the dialysis circuit 141 has a void volume from about 0.15 to about 0.5 L. In other embodiments, the dialysis circuit 141 has a void volume from about 0.2 to about 0.4 L or from 0.2 to about 0.35 L. Other volumes can be envisioned by those of ordinary skill in the art depending on parameters such as patient weight, size, and health condition. The system can be designed to be a portable system; however a desktop system or a large system suitable for heavy use in a clinical setting. Hence, both large volumes greater than 0.5 to about 5 L, and micro-volumes from as small as 0.1 to about 0.2 L are contemplated by the invention.

The controlled compliance dialysis circuit has two points where fluid can enter the dialysate flow path: 1) infusate pumps and 2) one or more control pumps that control the movement of fluid across the dialysis membrane. The controlled compliance dialysis circuit operates by employing two principle components: 1) an extracorporeal circuit that is attached to the vasculature and the circulation of a patient, and 2) a dialysis circuit having a limited void volume for the circulation of a dialysate. The extracorporeal circuit is an extension of the patient's circulatory system external to the patient's body. Any fluid added to the dialysate circuit will enter the patient's body; likewise, any fluid drawn out of the extracorporeal circuit originates from the patient's body. Due to the connection between the extracorporeal circuit and the vascular system, there is freedom of movement for fluid to flow into and out of the extracorporeal circuit due to the relatively large volume of the patient's body to accommodate an influx of fluid or to serve as a reservoir of fluid.

While the components forming the dialysis circuit have a controlled compliant volume, the dialysis circuit further incorporates a first control pump 190 that can be operated to selectively adjust the volume of the dialysis circuit. Specifically, the action of typical pumps functions by expanding or contracting a space. When the control pump is provided on the dialysate circuit, the volume of the dialysate circuit can be expanded or contracted in a controlled fashion allowing for the movement of fluid across the dialysis membrane to be actively controlled by the user or a programmed controller. The control pump 190 allows for fluid to move from the dialysate circuit to the extracorporeal circuit without creating a vacuum, wherein the operation of the control pump is controlled. Likewise, the control pump 190 allows for fluid to move from the extracorporeal circuit, and hence the patient's body, through the action of the control pump, by selectively expanding the volume of the dialysis circuit. Movement of fluid between the extracorporeal circuit and the dialysis circuit can be accurately controlled and metered. Since the dialyzer can be a high-flux type, there can be some fluid flux back and forth across the dialyzer membrane due to the pressure differential on the blood and dialysate sides of the membrane. This is a localized phenomenon due to the low pressure required to move solution across the membrane and is called backfiltration, however, this results in no net fluid gain or loss by the subject.

In certain embodiments, the control pump 190 used in the invention can be a peristaltic pump, a volumetric metering pump, diaphragm pump, or a syringe style pump. During operation, the volume of the dialysate circuit changes continually during the treatment even when the system does not push fluid back into the patient. This volume changes in a controlled way. A typical dialysis blood pump peristaltic segment is 8 mm, which means that during one rotation of the pump, two rollers can move approximately 14 ml. Depending on the position of the roller with this segment, there is 0 ml to 7 ml difference in dialysate flow path volume within this pump segment. This pump description is for illustration purposes and is non-limiting. The amount of the stroke volume will be dependent on the specific pump segment and the length of the blood pump. A syringe pump can also always have a changing volume, as can a simple metering device such as a diaphragm flow meter. As the flow path volume changes, the volume will expand and contract based on the stroke of the pumps. This change can be controlled. Hence, the dialysate circuit is substantially inflexible except for controlled changes in volume modulated by the UF pump and the infusion pump(s) that reflect the changes in volume due to the position of the peristaltic roller, syringe plunger or meter diaphragm and whether the pump is run forward or in reverse. In another embodiment, the blood pump and dialysate pump can be run in-phase, or not run 180 degrees out-of-phase. In contrast, known systems run the blood pump and dialysate pump 180 degrees out-of-phase, i.e., when the blood pump pumps, the dialysate pump is stopped and vice versa. However, because the amount of water that crossed into the blood during the dialysate stroke must be removed during the blood pump stroke, there is a tendency for the blood to hemoconcentrate and violate the blood filtration fraction. The ultrafiltration rate cannot exceed the acceptable filtration fraction. Filtration fraction (FF) is defined as FF (%)=(Ultrafiltration Rate×100)/Plasma flow. Plasma flow (Qp) is defined as Qp=Blood Flow Rate×(1-hematocrit). The maximum ultrafiltration rate cannot be greater than plasma flow×30%. The invention can also be programmed to have a physician prescribed maximum ultrafiltration rate, which is lower than the filtration fraction derived maximum ultrafiltration rate. In the invention, the fluid flows, into and out of the circuits, are controlled so that the blood pump is running when the fluid is removed to avoid violation of the filtration fraction, and to avoid hemoconcentration for less clotting.

The controlled compliance dialysis circuit can be accurately controlled to precisely remove or add fluid to the dialysis circuit 141. Due to the substantially inflexible void volume of the conduits, the sorbent cartridge 102 and other components of the dialysis circuit 141, the net movement of fluid over any time interval across the dialysis membrane 135 can be accurately controlled by creating a means to accurately introduce or remove fluid from the patient.

The controlled compliance dialysis circuit also has an advantageous feature in that the movement of fluid across the dialysis membrane 135 can be controlled without affecting the flow rate of dialysate entering the dialyzer 130.

Systems that rely solely on the internal pressure of the dialysis circuit to perform ultrafiltration have the disadvantage that the return of dialysate to the dialyzer is reduced by the amount of fluid being removed by ultrafiltration. That is, the rate that ultrafiltered fluid leaves the dialysis circuit necessarily lowers the return flow of dialysate to the dialyzer. In contrast, the present invention contemplates a separate first control pump 190 and dialysate pump 138 that allow for the rate of fluid return to the dialyzer to remain constant and/or not affected by the removal of fluid volume from the dialysis circuit.

Due to the substantially inflexible void volume of the conduits and the sorbent cartridge 102, bulk fluid or water is prevented from moving across the membrane 135 from the extracorporeal circuit 140 to the dialysis circuit 141. Specifically, due to the substantially inflexible void volume of the dialysis circuit 141, water cannot passively move from the extracorporeal side to the dialysate side through the dialysis membrane. In the event of factors that tend to increase pressure on the extracorporeal side of the dialysis membrane, such as increase blood flow rate or blood viscosity, pressure across the membrane will automatically be equalized due to the limited volume of the dialysis circuit 141 and the non-compressible nature of the dialysate. In the event of factors that tend to increase pressure on the dialysate side of the dialysis membrane 135, such as increased dialysis flow rate, net movement of water from the dialysis circuit 141 to the extracorporeal circuit 140 is prevented by a vacuum that would form in the dialysis circuit 141 in the event of such a movement. In certain embodiments, the dialysis circuit 141 has a void volume from about 0.15 to about 0.5 L. In other embodiments, the dialysis circuit 141 has a void volume from about 0.2 to about 0.4 L or from 0.2 to about 0.35 L. Other volumes can be envisioned by those of ordinary skill in the art depending on parameters such as patient weight, size, and health condition. The system can be designed to be a portable system, a desktop system or a large system suitable for heavy use in a clinical setting. Hence, both large volumes greater than 0.5 to about 5 L, and micro-volumes from as small as 0.1 to about 0.5 L such as 0.1 to 0.2, 0.1 to 0.3, 0.1 to 0.4, 0.2 to 0.3, 0.3 to 0.4, or 0.3 to 0.5 L are contemplated by the invention.

Using the controlled compliance dialysis circuit described herein, net movement of water across the dialysis membrane occurs under active control rather than passively due to pressure differences that develop across the dialysis membrane due to normal operations. Control pump 190 accesses the controlled compliance dialysis circuit 141 through conduit 191. In certain embodiments, the conduit 191 joins with the controlled compliance dialysis circuit 141 at a point downstream from the dialyzer 130. The control pump 190 can be operated in an influx direction that moves fluid from a first control reservoir 192 to the controlled compliance dialysis circuit 141 or in an efflux direction that moves fluid from the controlled compliance dialysis circuit 141 into the first control reservoir 192. Due to the substantially inflexible volume of the dialysis circuit 141, volume added to the controlled compliance dialysis circuit when the control pump 190 operates in the influx direction causes net movement of fluid from the dialysate side of the dialysis membrane 135 to the extracorporeal side of the dialysis membrane 135. When the control pump 190 is operated in the efflux direction, fluid is drawn from the extracorporeal side of the dialysis membrane into the controlled compliance dialysis circuit. In certain embodiments, the control pump 190 can be operated at a rate from 0 to about 200 mL/min in either direction. In certain other embodiments, the control pump 190 can be operated at a rate from 0 to about 100 mL/min or 0 to 50 mL/min in either direction.

The first control reservoir 192 is not limited to any particular structure. In certain embodiments, the first control reservoir 192 can be made from a flexible or collapsible material that expands depending on the volume held. In certain embodiments, the control reservoir 192 can have a valve that allows the patient to empty the volume of the control reservoir 192 with interrupting treatment. In certain embodiments, the control reservoir 192 can be substantially inflexible. The control reservoir 192 can include a hydrophobic 0.2 micron (µm) sterile, non-pyrogenic, and non-toxic air filter 300 to prevent the entry of bacteria or endotoxin into the first control reservoir 192 and dialysis circuit 141. The air filter 300 also sterilizes air exhaust and intake from the first control reservoir 192 into the system. Further, the air filter 300 can also release air pressure present in the first control reservoir 192. The material of air filter 300 may be Millipore Dualex™ filter or an equivalent known to one of ordinary skill.

In embodiments where the control pump 190 is operated in the influx direction, the dialysate pump 138 operates at a rate higher than the control pump 190 to prevent flow of the used dialysate back into the dialyzer 130. The dialysate pump 138 functions to convey the dialysate from the point where line 191 joins the dialysis circuit 141 to the sorbent cartridge 102. A rate of the dialysate pump 138 operating faster than the control pump 190 in the influx direction ensures that the contents of the control reservoir 192 are conveyed to the sorbent cartridge 102 and do not reach the dialyzer 130 without first passing through the sorbent cartridge. In certain embodiments, the dialysate pump 138 operates at a rate that is about 100 mL/min greater and at rates greater than the rate of the control pump 190, when the control pump 190 is operating in the influx direction. For example, if the rate of the control pump 190 is 10 mL/min, the dialysate pump 138 can operate at rates greater than about 110 mL/min such as 130 mL/min, 175 mL/min, 210 mL/min, 510 mL/min, 760 mL/min, 1 L/min, and 1.6 L/min. If the rate of the control pump 190 is 25 mL/min, the dialysate pump 138 can operate at rates greater than about 125 mL/min such as 130 mL/min, 175 mL/min, 210 mL/min, 510 mL/min, 760 mL/min, 1 L/min, and 1.6 L/min. In one embodiment, the dialysate pump 138 operates at a rate that is about 20 mL/min greater and at rates greater than the rate of the control pump 190 or higher, when the control pump 190 is operating in the influx direction. In other embodiments, the dialysate pump 138 operates at a rate that is about twice the rate and at rates greater than that of the control pump 190, when the control pump 190 is operating in the influx direction. In certain embodiments, the dialysate pump 138 operates at a rate that is about 5% higher and at rates higher than the rate of the control pump 190, when the control pump 190 is operating in the influx direction. For example, the dialysate pump 138 can operate at 6%, 7%, 8%, 10%, 15%, 45%, 63%, 75%, 100%, 200%, 500%, 2000%, or any higher percentage than the rate of the control pump 190.

As shown in FIG. 1, the dialysate is moved along the dialysis circuit 141 by a dialysate pump 138. When the control pump 190 is not operating, fluid along the length of the dialysis circuit 141 flows at a rate determined by the dialysate pump 138. When the control pump 190 is operating, fluid exiting the dialyzer 130 and traveling toward the conduit 191 is flowing at rate that is the combination of the rates of the control pump 190 and the dialysate pump 138. However, the fluid traveling from the entry point of conduit 191 into the dialysis circuit 141 to the dialyzer 130 is traveling at the rate of the dialysate pump 138. As such, the rate of fluid traveling to the dialyzer 130 is not affected by the operation of the control pump 190. The dialysate pump can be operated at a rate from about 10 to about 400 mL/min, the specific rate being dependant on the rate of the blood pump 125 and the desired contact time with the dialysis membrane 125 to achieve diffusion of waste species from blood to the dialysate. The rate of the dialysate pump 138 and the blood pump 125 can be controlled by a controller 801.

Convective Clearance

In addition to accurately controlling the net fluid removed and the convective clearance of a patient, accurate control of the efflux or influx of fluid via the compliance control pump 190 allows for the amount of sodium removed (mEq $Na^+$) during a course of treatment to be determined, where such result can be calculated and stored in the memory of a controller 801 and/or be displayed on a control panel (not shown). Accurate control of bulk fluid movement across the dialysis membrane can further be used to enhance clearance of mid-weight waste species by convective clearance, which is particularly beneficial for mid-weight waste species, such as β-2 microglobin that are not removed very well by hemodialysis and for which higher serum blood levels are associated with higher patient mortality. To be able to control net patient fluid removal, any fluid removed in excess of the desired patient fluid loss must be reinfused to the blood. This is accomplished in one embodiment by running the control pump 190 in reverse during the treatment and then compensating by ultrafiltration: Control Pump Control=Net patient UF+Convective UF. Control pump back filtration is controlled to Convective UF volume. For example, a desired 200 ml net patient fluid loss per hour and 1000 ml of convection per hour requires a control pump 190 running at a UF rate (efflux rate) of 1000 ml/hr and at a back filtration rate (influx rate) of 800 ml/hr to achieve the net fluid loss and the desired convective clearance. These same mechanisms allow one to give fluid to the patient when necessary, rinse back blood and control fluid removal accurately.

The rate of diffusion of a solute is dependent upon the molecular weight of that solute. Small molecules, such as urea, can effectively diffuse from the extracorporeal side of the dialysis membrane to the dialysate side of the dialysis membrane in the absence of net movement of fluid. However, larger, mid-sized molecules, having a lower rate of diffusion may not be removed as effectively. As used herein, the term mid-sized molecule refers to a waste species having a molecular weight less than about 66000 g/mol and greater than about 1000 g/mol and includes uremic toxins, B12, C reactive protein, and β2-microglobin.

During periods of net movement of fluid from the extracorporeal side to the dialysate side of the dialysis membrane 135, solutes can be dragged across the dialysis membrane 135 along with the net movement of fluid. This process, referred to as convective clearance, removes mid-weight waste species from the patient's blood, which are absorbed by the sorbent cartridge 102. Some convective clearance occurs during the course of ultrafiltration as described above. However, the amount of convective clearance is limited by the volume of fluid that is removed by ultrafiltration. For example, if 1 L of fluid is to be removed from the patient over the course of a 4-hour treatment, then the amount of convective clearance that occurs due to 1 L of fluid crossing the dialysis membrane 135 is the maximum amount of convective clearance that occurs during the treatment regimen. Without infusing the patient with additional fluid, the amount of fluid that can be removed is limited considering that the average individual has about 5 L of blood. Further, it may be desirable to achieve convective clearance without the removal of a large amount of fluid from the patient.

To achieve convective clearance in accordance with certain embodiments, the control pump 190 is operated in the efflux direction to pull fluid from the extracorporeal circuit 140, and hence from the patient, across the dialysis membrane 135. During the net efflux for fluid across the membrane 135, mid-weight solutes and waste species are carried into the circulating dialysate where they can be absorbed by the sorbent cartridge 102. The control pump 190 is periodically reversed to the influx direction to force fluid from the first control reservoir 192 into the controlled compliance dialysis circuit 141 and thereby force a corresponding volume of fluid into the extracorporeal circuit 140 and into the patient. During influx, fluid from first control reservoir 192 is not returned to the dialyzer 130 and must first pass through the sorbent cartridge 102. As discussed above, pressures, rates, and control means are adjusted to ensure that used dialysate is not returned to the dialyzer 130 from the dialysate circuit 141.

Under a regime where the control pump 190 is run in the efflux and influx directions for approximately equal amounts of time at the same pump rate, the amount of convective clearance will be approximately the efflux flow rate without causing any net addition or removal of fluid from the patient. For example, if the compliance control pump 190 is run at 10 mL/min for a hour with periodic reversal between efflux and influx directions, then 300 mL of fluid is moved from the extracorporeal circuit into the controlled compliance dialysis circuit 141 to affect convective clearance, where the same volume is returned to the patient resulting in no net fluid removal at the end of treatment. In the alternative, the time that the control pump 190 is operated in the efflux or influx direction can be unequal to affect a net volume of ultrafiltration during the course of treatment. For example, if the control pump 190 is operated in the efflux direction for 18-second periods with intervening 12-second periods in the influx direction at a rate of 10 mL/min, then 360 mL/h of fluid is moved in the efflux direction to affect convective clearance and a net of 120 mL/h of fluid is removed from the patient. Those skilled in the art will understand that the interval at which the control pump 190 operates between efflux and influx directions can be modified to further effect the amount of convective clearance and net ultrafiltration occurring over the course of treatment.

The blood pump 125 and the dialysate pump 138 provide the majority of the energy to convey the blood through the extracorporeal circuit 140 and the dialysate through the controlled compliance dialysis circuit 141, respectively. In certain embodiment, the blood pump and the dialysate pump can be independently operated at any rate in a range from about 50 to about 300 mL/min including from about 60 to about 295 mL/min is contemplated by the invention such as about 76 to about 185 mL/min, about 85 to about 287 mL/min, about 25 to about 115 mL/min, about 45 to about 273 mL/min, about 156 to about 293 mL/min, about 32 to about 163 mL/min, about 145 to about 199 mL/min, about 167 to about 193 mL/min or, about 29 to about 224 mL/min. In certain embodiments, the blood pump and/or the dialysate pump deliver a constant load pressure such that the conveyance rate is constant over at least short periods of times. Pumps that can deliver a constant load pressure include peristaltic pumps.

The use of pulsatile pumps, that mimic the pulsing action of the human heart, has been proposed to enable convective clearance. As discussed herein, in known devices, the blood and the dialysate are conveyed by pulsatile pumps that are set 180 degree out of phase in order to achieve periodic filtering across the dialysis membrane. When the blood pump is undergoing a pulse action and the dialysate pump is at rest, convective clearance can occur due to an increase in pressure difference across the dialysis membrane. Conversely, fluid is back filtered across the dialysis membrane when the dialysate pump is undergoing a pulse action and the blood pump is at rest. However, such systems have been subject to increased clotting. It is desirable to stop the administration of heparin or other anticoagulant 30 to 60 minutes prior to the end of dialysis to restore normal clotting by the time treatment ends. However, blood becomes significantly more viscous at low flow rates. In addition, protein coats the membrane surface starting the clotting cascade. The periodic slow down of blood circulation caused by the action of a pulsatile pump contributes to clotting occurring in the extracorporeal circuit. Blood clotting prevents the completion of treatment.

The above-described method for performing convective clearance using pulsatile pumps requires the flow rate of the blood and the dialysate through the dialyzer to be similar to function properly. The pressure generated in the dialyzer on either side of the dialysis membrane is dependent upon the flow rate, where the flow rate of the dialysate and the blood should be close to achieve equal movements of fluid in both directions across the dialysis membrane. Specifically, the ratio of blood flow to dialysis flow has been recommended to be from 3:4 to 4:3 when employing pulsatile pumps to increase convective clearance. The use of pulsatile pumps to perform convective clearance also increases hemoconcentration, which increases the risk for blood clotting. As the flow rate of blood through a dialyzer is lowered relative to the flow rate of dialysate through the dialyzer, any particular volume of fluid pulled from the extracorporeal circuit during a unit value of time causes a greater amount of hemoconcentration. That is, the volume of fluid removed from the extracorporeal circuit is removed from a smaller volume of blood as the flow rate of blood is lowered. As described above, a ratio of blood flow to dialysis flow has been recommended to be from 3:4 to 4:3 when pulsatile pumps are used to create convective clearance. Using the controlled compliance dialysis circuit described herein, the net flux of fluid across the dialysis membrane 135 is controlled by the control pump 190 rather than a ratio of flow rates between blood and dialysate. As such, the ratio of blood flow to dialysate flow can be set at a value that reduces hemoconcentration as a result of pulling fluid from the extracorporeal circuit. In certain embodiments, the ratio of blood flow to dialysate flow through the dialyzer 130 is from about 1:1.5 to about 3:1, and can include any range of ratios in between. In certain other embodiments, the rate of blood flow through the dialyzer 130 is at least about 50% greater than the rate of dialysate flow through the dialyzer 130.

Portable Treatment Module for Ultrafiltration

Figure 2:
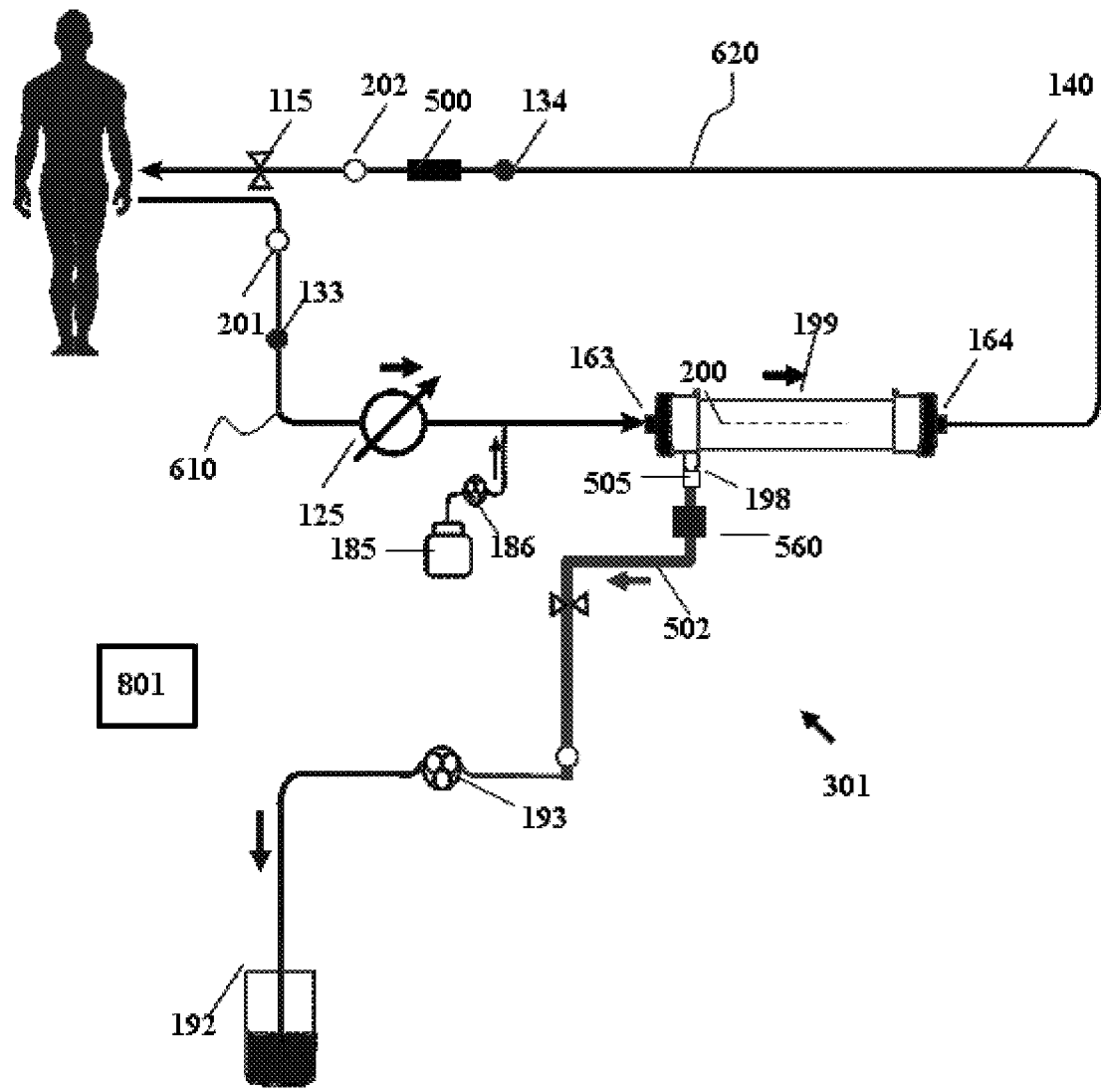
FIG. 2 shows a modular ultrafiltration system having an extracorporeal circuit, hemofilter and a control pump.

FIG. 2 shows an ultrafiltration system for circulating blood through a hemofilter 199 using a portable treatment module 301. The portable treatment module 301 has an extracorporeal circuit 140 having a similar configuration as in the portable treatment module 100 shown in FIG. 1. A shunt, such as a needle or catheter, is connected to a subject's vasculature to draw blood and circulate the patient's blood through the extracorporeal circuit 140. The portion of the extracorporeal circuit labeled 610 is an arterial line that contains blood drawn from the subject and being conveyed to the hemofilter 199. The portion of the extracorporeal circuit labeled 620 is a venous line that returns blood to the subject. Locomotive power for moving the blood through the extracorporeal circuit 140 is provided by a blood pump 125, which is typically located along the arterial line 610. Blood is typically conveyed through the extracorporeal circuit 140 at a rate of 50 to 600 mL/min and can be adjusted by a controller 801 to any required rate suitable for hemofiltration.

Blood pump 125 can be a peristaltic pump, although those skilled in the art will readily understand that other types of pumps can be used, including diaphragm pumps, centrifugal pumps, and shuttle pumps. In certain embodiments, blood pump 125 is not a pulsatile pump. In certain embodiments, the blood pump 125 conveys blood through the hemofilter 199 where the blood is contacted with a blood side of a high permeability hemofiltration membrane 200. Blood enters the hemofilter 199 through a blood inlet 163 and exits through a blood outlet 164. The pressure of the blood prior to the dialyzer 130 is measured by a pressure meter 133 and post dialyzer 130 by a pressure meter 134. The pressure at pressure meter 133 gives an indication of the adequacy of the blood flow into the circuit, increased vacuum is an indication of a less adequate access flow. The pressure indication at pressure meter 134 indicates obstructions in the venous bloodline 620. An air trap 500 is placed along the extracorporeal circuit 140 to prevent the introduction of air into the circulatory system of the patient. The air trap 500 is not limited to a particular design. Typical air traps employ a hydrophobic membrane that allows air to be separated from an air-liquid mixture by allowing air to pass through the membrane and retaining water-based fluids. Alternatively, the air trap 500 can be run full, where a pressure meter can use a flexible impermeable membrane to transmit pressure pulses to a pressure transducer such that there is no direct air-blood interface. Air-fluid detectors 201 and 202 can optionally be present to confirm that air is not present in the extracorporeal circuit 140. Air-fluid detectors 201 and 202 can be ultrasonic sensors that can detect a change in solution density or scattering due the presence of air or air bubbles. A valve 115 can be present to control access to the subject's vascular system.

During the course of conveyance of blood along the extracorporeal circuit 140, heparin or a similar anticoagulant is added to the blood to prevent clotting of blood within the dialyzer 130 or any of the conduits forming the blood conveyance pathway/extracorporeal circuit 140. Heparin or another anticoagulant is added from an anticoagulant container 185 at a metered rate using an anticoagulant pump 186. The anticoagulant pump 186 can be any pump capable of accurately metering heparin. Alternatively, a surface of the extracorporeal circuit 140 can be covalently bound to heparin or a like anticoagulant.

The hemofilter 199 has an ultrafiltrate outlet 198 that is connected by one or more conduits to a filtration pump 193. The filtration pump 193 can serve to apply a negative pressure to the ultrafiltrate outlet 198 and thereby draw an ultrafiltrate across the hemofiltration membrane 199. A valve can be present to prevent the passage of air or backflow into the hemofilter 199 during periods where the filtration pump 193 is not operating. Further, a blood leak detector 560 can be present to detect the presence of blood in the ultrafiltrate, where the blood leak detector 560 can be a photoabsorption detector.

The configuration shown in FIG. 2 can be used to remove excess fluid from a patient into a storage container 192 while the subject remains ambulatory. The fluid removal process of a healthy renal system is thereby mimicked. Some waste products can also be removed during the ultrafiltration treatment as a result of solvent drag across the hemofiltration membrane 200. However, the rate of ultrafiltration as controlled by the rate of filtration pump 193 is kept at a moderate level to allow for the replacement of the volume removed from the blood by migration of fluid from the body tissues surrounding the vasculature of the subject. As such, hemoconcentration can be avoided since portable module 301 does not necessarily contain a facility to provide a replacement solution.

Figure 3:
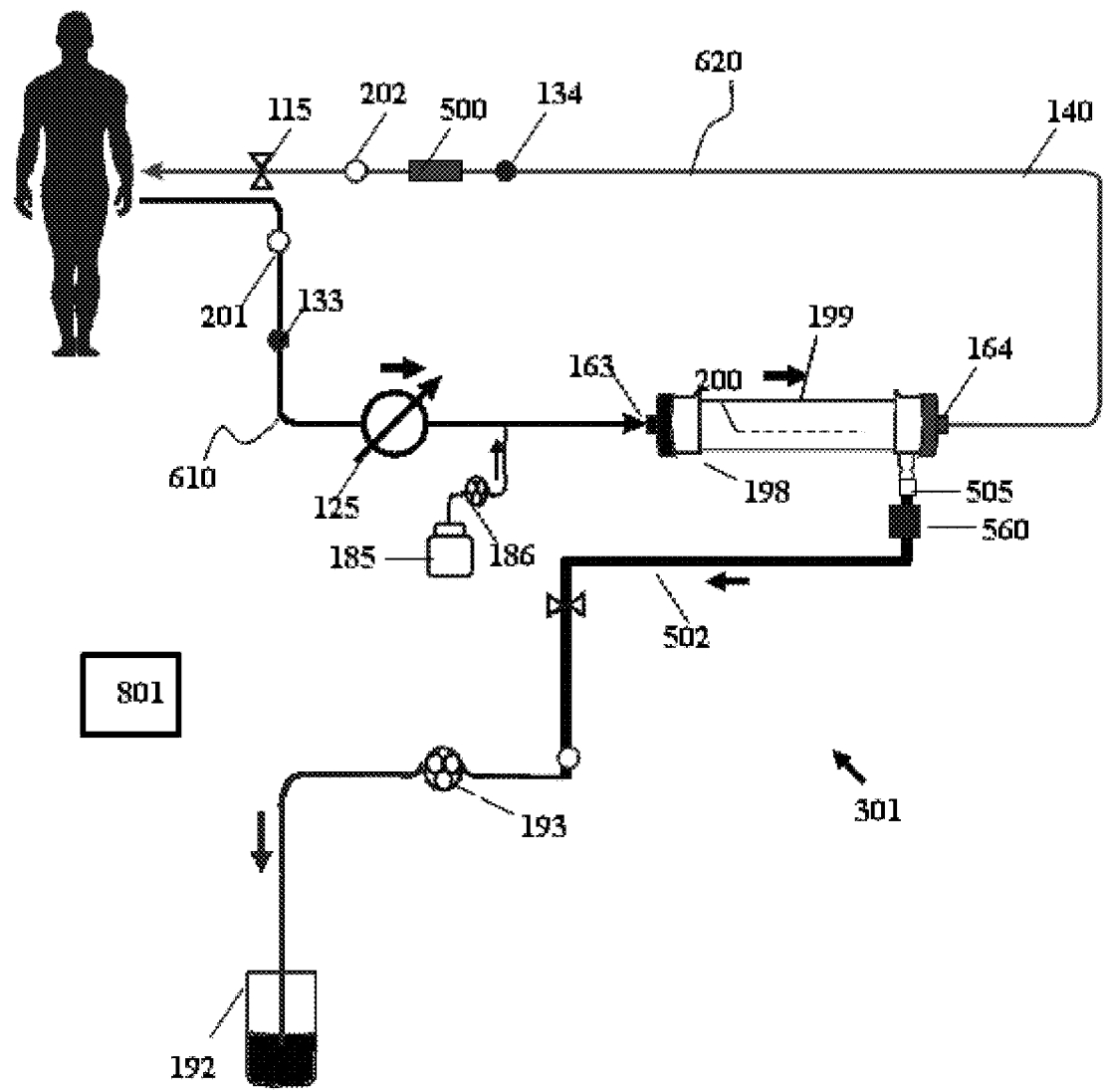
FIG. 3 shows a modular ultrafiltration system having an extracorporeal circuit, hemofilter and a control pump.

The hemofilter 199 is structurally similar to the dialyzer 130 described above in relation to portable module 100. Although not shown in FIG. 2, hemofilter 199 has a second port that is structurally equivalent to dialysate inlet 194 that is sealed during operation of the portable dialysis module 301, which allows for the connection to the urea removal module 400 described below. That is, the hemofilter 199 is adaptable to function as a dialyzer. An alternate configuration of the portable dialysis module 301 is shown in FIG. 3, where ultrafiltrate outlet 198 is positioned at the structure equivalent to dialysate inlet 194 when the hemofilter 199 is operated as a dialyzer.

As described above, the rate of ultrafiltration is limited to 30% of Qp to prevent excessive hemoconcentration. In most situations, the rate of ultrafiltration is limited to a moderate rate to allow for adequate movement of fluid for body tissues to the vasculature of the subject. In certain embodiments, the filtration pump 193 is operated at a rate from 0 to about 15 mL/min, where the rate of ultrafiltration is limited to the same rate.

Urea Removal Module

Figure 4:
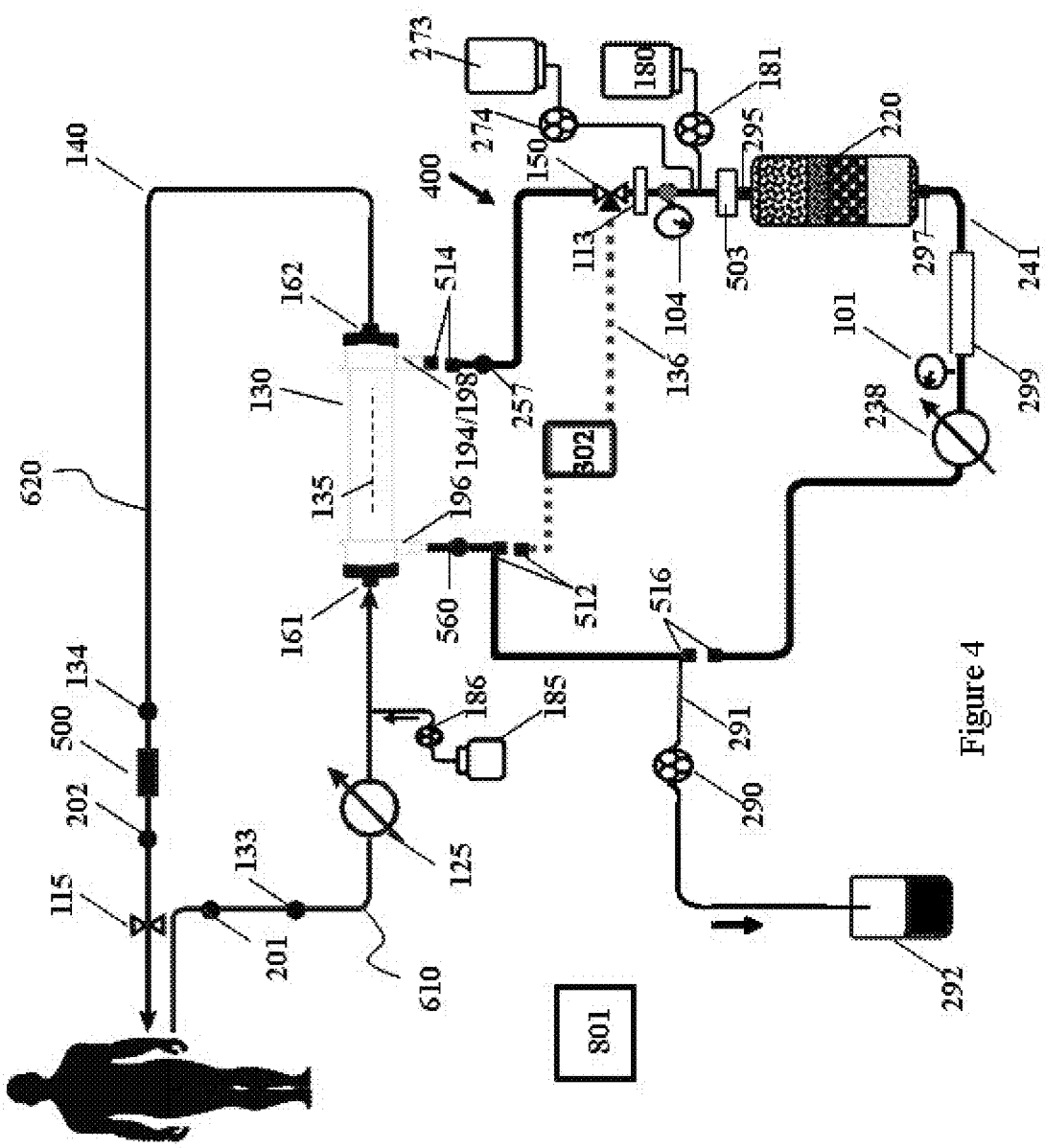
FIG. 4 shows the attachment of an extracorporeal circuit and a dialyzer to a urea removal module in accordance with certain embodiments disclosed herein.

The connectors 502 and 504 shown in FIG. 1 can be disconnected from the portable treatment module 100 to connect the extracorporeal circuit 140 to a urea removal module 400. Similarly in FIGS. 2 and 3, connector 505 can be disconnected from the portable treatment module 301. As shown in FIG. 4, three pairs of quick connectors 512, 514 and 516 are employed by a user to connect the extracorporeal circuit 140 to the urea removal module 400. Connectors 512 connect to the dialysate output end 196 of the dialyzer 130 and connectors 514 connect to the dialysate input end 194 of the dialyzer 130. Connectors 516 connect to a conduit 291 and a control pump 290; control pump 290 can be the same pump as control pump 190 or filtration pump 193 or a different pump.

Figure 5:
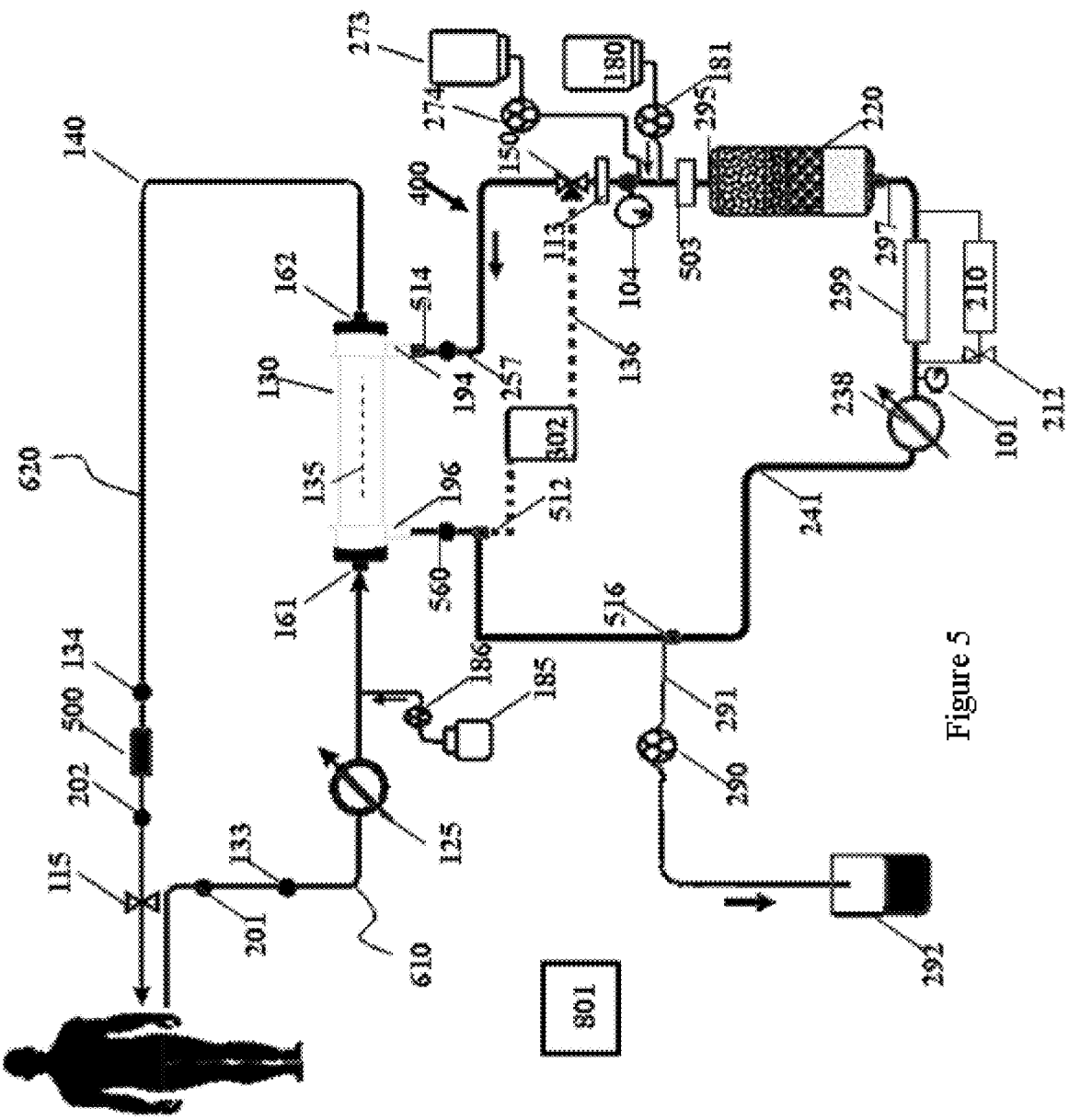
FIG. 5 shows a hemodialysis device having an extracorporeal circuit, dialyzer, and a urea removal module having a controlled compliant dialysis circuit operating in accordance with certain embodiments.

Once connected to the extracorporeal circuit 140, dialysate is conveyed through a dialysis circuit 241 of the urea removal module 400 by means of a dialysate pump 238, as shown in FIG. 5. The dialysis circuit 241 has the same substantially inflexible volume and controlled compliant properties of the dialysis circuit 141 of the portable module 100 described above. Specifically, control pump 290 can be operated in the efflux or influx direction to control the flow of bulk fluid across the dialysis membrane 135, to perform convective clearance and to add or remove fluid from first control reservoir 292 in the same manner as control pump 190 described above. Similarly, a second reservoir pump 274 and a second control reservoir 273 can optionally be present as shown in FIGS. 4 and 5. The dialysate pump 238 and control pump 290 are operable at the same rates and in the same manner as dialysate pump 138 and control pump 190, respectively. The control reservoir 292 can have the same features as control reservoir 192 and air filter 300. The urea removal module 400 can include an optional heater 299 for warming the dialysate. Reference numbers shared among FIGS. 1, 4 and 5 represent like elements and features.

As described above, the control pump 190/290 can be operated in a bidirectional fashion to assist in the performance of convective clearance. Specifically, the control pump 290 can be operated in the efflux direction to cause the movement of fluid from the extracorporeal circuit 140 into the dialysis circuit 241 and in the influx direction to cause the movement of fluid from the dialysis circuit 241 into the extracorporeal circuit 140. In certain embodiments, operation of the control pump 290 in the influx direction can be substituted with operation of the second reservoir pump 274 to drive fluid from the second control reservoir 273 into the dialysis circuit 241 and subsequently cause movement of fluid from the dialysis circuit 241 to the extracorporeal circuit across the dialysis membrane 135. The control pump 290 can be used for the movement of fluid in the opposite or efflux direction across the dialysis membrane 135. The pump second reservoir 274 and second control reservoir 273 can be used for the performance of convective clearance in embodiments of the invention where the total void volume of the dialysis circuit and working dialysate is less than about 0.5 L, or in embodiments where the void volume of the dialysis circuit and working dialysate is less than 1 L.

In certain embodiments, the volume of fluid held by second control reservoir 273 is about 1 L or less, or about 0.5 L or less. In certain embodiments, the volume of the fluid held by the second control reservoir 273 is from about 0.1 to about 1 L, from about 0.2 to about 0.8 L, from about 0.5 to about 1 L, from about 0.6 to about 1 L, from about 0.5 to about 0.8 L or from about 0.2 to about 0.8 L. The second reservoir pump 274 can be operated at the same rates in the influx direction as either control pump 190 or 290. Optionally, a second control reservoir and second reservoir pump can be added to portable treatment module 100 (not shown).

The dialysis circuit 241 has the same properties to form a controlled dialysis circuit, where the conduits, sorbent cartridge 220 and other components of the dialysis circuit have a non-expandable volume. As such, the dialysis circuit 241 can be used to perform the ultrafiltration and convective clearance techniques described above. In certain embodiments, the dialysis circuit 241 has a void volume from about 0.15 to about 0.5 L. In other embodiments, the dialysis circuit 241 has a void volume from about 0.2 to about 0.4 L or from 0.2 to about 0.35 L. In certain other embodiments, the dialysis circuit 241 has a volume of less than about 1 L. Other volumes can be envisioned by those of ordinary skill in the art depending on parameters such as patient weight, size, and health condition. The system can be designed to be a portable system, a desktop system or a large system suitable for heavy use in a clinical setting. Hence, both large volumes greater than 0.5 to about 5 L, and micro-volumes from as small as 0.1 to about 0.5 L such as 0.1 to 0.2, 0.1 to 0.3, 0.1 to 0.4, 0.2 to 0.3, 0.3 to 0.4, or 0.3 to 0.5 L are contemplated by the invention.

The dialysate pump 238 conveys the dialysate to an inlet 297 of the sorbent cartridge 220, through the sorbent cartridge 220 and out an outlet end 295. An optional heater 299 may be present along the conduit of dialysis circuit 241 to heat the dialysate. An air trap 503 is positioned after outlet end 295 to remove gasses introduced into the dialysate by the sorbent cartridge 220. The dialysate enters the dialyzer 130 at the inlet end 194, picks up waste materials and exits the outlet end 196. The dialysate is then reconveyed to the sorbent cartridge 220 where waste materials are removed.

The sorbent cartridge 220 is competent to remove urea from the dialysate as well as uremic waste species and phosphates.

Sorbent materials that can perform removal of waste materials and regenerate the dialysate for use in sorbent cartridge 220 are known. Examples of useful sorbent materials include the REDY sorbent system. The sorbent cartridge typically contains four different kinds of materials as follows: 1) a urease-containing material, where urease is an enzyme that catalyzes the conversion of urea to ammonia (ammonium ions) and carbon dioxide; 2) a zirconium phosphate (ZrP) material that has the capacity to act as a cation exchanger by absorbing a large quantity of ammonium ions in exchange for sodium and hydrogen ions, where the ZrP material also exchanges $Mg^{2+}$, $Ca^{2+}$ and $K^+$ ions for sodium and hydrogen ions; 3) a zirconium oxide material (ZrO), which acts as an anion exchanger by exchanging phosphate for acetate and bicarbonate; and 4) an activated carbon material that has a surface area for adsorption of a wide range of impurities including metal ions and waste species including uremic toxins, such as uremic toxins, B12, C reactive protein, and β2-microglobin. Examples of useful sorbent materials include those sorbents discussed in U.S. Pat. Nos. 3,669,880; 3,989,622; 4,581,141; 4,460,555; 4,650,587; 3,850,835; 6,627,164; 6,818,196; and 7,566,432 and U.S. Patent Publications 2010/007838; 2010/0084330; and 2010/0078381, and International Patent Publication WO 2009/157877 A1, which are incorporated herein by reference. Zirconium phosphate materials can be replaced by magnesium phosphate materials as described in U.S. Pat. Nos. 4,460,555 and 4,650,587, which are incorporated herein by reference.

In certain embodiments, the urease-containing material, the zirconium phosphate material, the zirconium oxide material, and the activated carbon material are arranged into discrete layers within the sorbent cartridge 220. As will be described in more detail below, the various sorbent materials can be provided in separate housings or as discrete layers within such housings in certain embodiments. In certain embodiments, the urease-containing material and the zirconium phosphate material are intermixed in the same discrete layer within the sorbent cartridge 220. The urease-containing material can be immobilized or covalently linked to a substrate material. The substrate material is not particularly limited, where suitable substrate materials include organic polymers, carbohydrate-based polymers, polyamides, polyesters, inorganic polymeric materials, chitosan and silica gel. The inclusion of the urease-containing material and the zirconium phosphate material in the same discrete layer can improve workability of the sorbent materials to prevent clogging of the sorbent cartridge 102 or improve absorption of ammonium ions by the zirconium phosphate material.

As described above, the processes and sorbent materials releases sodium ions into the dialysate thereby increasing the conductivity. Refreshed dialysate exiting an outlet end 295 of the sorbent cartridge 220 can be monitored by a conductivity meter 104. Necessary electrolytes that are removed by sorbent cartridge 220 are added to the refreshed dialysate from a reservoir 180 having an infusate solution by an infusate pump 181, such as $K^+$, $Mg^{2+}$ and $Ca^{2+}$ ions. The point at which the infusate (i.e. cation) solution is added to the dialysate can be between the sorbent cartridge 220 and the valve 150 in certain embodiments or between the sorbent cartridge 220 and the dialysate inlet 194 of the dialyzer 130 in other embodiments. The design of any conductivity meter employed in embodiments described herein is not particularly limited; however, a typical conductivity meter has two electrodes where a current between the two electrodes is monitored. The presence of sodium ions in the dialysate is the major contributor to the conductivity measured by conductivity meter 104. Conductivity is continually monitored and reported to the controller 801 to assess the quality and safety of the dialysate. When the conductivity of the dialysate falls within a predetermined range, the dialysate is directed by valve 150 to a dialysate inlet end 194 of the dialyzer 130; the valve 150 is located between an outlet end 295 of the sorbent cartridge 220 and the dialysate inlet end 194 of the dialyzer 130. In certain embodiments, the valve 150 is a three-way valve. It is understood by one skilled in the art that three-way valve 150 can be replaced with a two-way valve with the same result to control the flow through the dialyzer 130 or bypass pathway 136. It is understood by one skilled in the art that three-way valve 150 can be replaced with a two-way valve with the same result to control the flow through the dialyzer 130 or bypass pathway 136. Optionally, the dialysate can be filtered through a microbial filter 113. The pressure of the dialysate entering the dialysate inlet end of the dialyzer 130 is measured by a pressure meter 257. In certain embodiments, the predetermined range for the conductivity of the dialysate is from about 12.6 to about 15.4 mS/cm.

When the conductivity measured by meter 104 is outside of the predetermined range, the valve 150 can direct the dialysate to be conveyed through a bypass pathway 236 (shown as a dashed line). The dialysate can be circulated through the sorbent cartridge 220 while bypassing the dialyzer 130 and preventing contact with the subject's blood when required.

The conductivity of the dialysate needs to be adjusted to be within an acceptable range to perform hemodialysis. The dialysate can be passed through a mixed-bed anion and cation exchange (mixed bed de-I) resin. The mixed bed de-I resin contains an anion exchange resin that exchanges anions present in the dialysate (e.g. $Cl^-$) for hydroxyl ions and a cation exchange resin that exchanges cations present in the dialysate for hydrogen ions. Dialysate passing over the mixed bed de-I resin becomes substantially deionized with low conductivity.

Suitable filters for use as microbial filter 112 or 113 include microfilters and ultrafilters manufactured or supplied by Minntech, Medica, Pall Corporation or Millipore®, but any known by those of ordinary skill for the intended purpose can be used. In certain embodiments, the dialysate passing through the dialyzer 130 has low levels of both active bacterial and endotoxins. Desirable quality for the dialysate is less than about 1 colony forming unit (cfu)/mL and detectable endotoxins less than about 0.3 ELISA unit EU/ml. Further, the sorbent cartridge 220 can include a spacer frit, which is a membrane or material that is designed to prevent fines from leaving the cartridge. After this spacer frit, an endotoxin or retentive membrane can be placed to prevent the passage of endotoxins and bacterial. Examples of an endotoxin or retentive membrane include quaternized amine charged surface membranes such as those manufactured or supplied by Pall Corporation (Ann Arbor, Mich.). Endotoxin levels can be measured using a qualified assay with limulus amebocyte lysate assay using blood from the horseshoe crab through guidelines promulgated by the U.S. Food and Drug Administration or dialysis standards such as AAMI/ANSI/ISO 23500 Guidance for the preparation and quality management of fluids for hemodialysis and related therapies.

As shown in FIG. 5, a deionization cartridge 210 can be placed along the dialysate circuit 241 before the inlet to the sorbent cartridge 220. Dialysate flow through the deionization cartridge 210 is controlled by a valve 212. Valve 212 can be actuated in response to an increase in the measured conductivity of the dialysate as measured by conductivity meter 104 and/or 101. The dialysate passing through the deionization cartridge becomes substantially deionized and acts as a diluent when added to the dialysate circuit 241. The conductivity of the dialysate circulating through the dialysis circuit can be controlled in response to the cation exchange activity of the zirconium phosphate material. The use of deionization cartridge 210 is optional. Sodium in the dialysate can also be decreased by operation of control pump 190, where fluid entering the dialysate from the blood can act as a diluent. Further, the second reservoir pump 274 can be used to add a low conductivity fluid to the dialysate circuit 241 when required.

Several sensors and monitors can be employed to determine the state of the dialysis system, as shown in the Figures. Blood leaks across the dialysis membrane 135 or hemofiltration membrane 200 can be detected by a blood leak detector 560. The blood leak detector 560 can be an optical detector having a light source and photo detector allowing for the observation of a red color in the dialysate. Conductivity meters 101 and 104 can be present to monitor the composition of the dialysate within the dialysis circuit. Pressure meters 133, 134 and 257 can be present to determine an unsafe operating pressure and/or fluid leak from the system. The pressure meter can be a transducer device that operates through capacitive or piezoelectric principles to convert the amount of force applied to a surface to an electronic signal.

Suitable filters for use as microbial filter 112 or 113 include ultrafilters manufactured or supplied by Minntech, Pall Corporation or Millipore®, but any known by those of ordinary skill for the intended purpose can be used. In certain embodiments, the dialysate passing through the dialyzer 130 has low levels of both active bacterial and endotoxins. Typically, the output of the sorbent cartridge in prior art sorbent systems meets the Association for the Advancement of Medical Instrumentation's (AAMI) Water for Hemodialysis standard but does not meet the AAMI standard for microbiologically ultrapure dialysate. It has been shown in the medical literature that ultrapure dialysate is desirable in reducing the inflammatory response in the ESRD patient. Desirable quality for ultrapure dialysate is less than about 1 colony forming unit (cfu)/100 ml where cfu is the number of viable cells per unit volume, and detectable endotoxins less than about 0.03 ELISA unit (EU/mL). In certain embodiments, the dialysate passing through the dialyzer 130 has low levels of both active bacteria and endotoxins. In one embodiment, a microbial filter 112 or 113 placed in the dialysis circuit 141/241 can be present to prevent bacteria and endotoxin from reaching the patient. Suitable filters include ultrafilters and microfilters manufactured or supplied by Minntech, Medica, Nikkiso, Pall Corporation or Millipore®, however any known by those of ordinary skill for the intended purpose can be used. Further, the sorbent cartridge 102 or 220 can include a spacer frit, which is a membrane or material that is designed to prevent fines from leaving the cartridge. After this spacer frit, an endotoxin or retentive membrane can be placed to prevent the passage of endotoxins and bacterial. Examples of an endotoxin or retentive membrane include quaternized amine charged surface membranes such as those manufactured or supplied by Pall Corporation (Ann Arbor, Mich.). Endotoxin levels can be measured by using a qualified assay with limulus amebocyte lysate assay using blood from the horseshoe crab through guidelines issued by the U.S. Food and Drug Administration.

Control of pH

Constant pH in the blood is maintained by the presence of bicarbonate which is equilibrated with $CO_2$ through the action of carbonic anhydrase. Systems employing a sorbent cartridge 220 including urease and zirconium oxide have a tendency to induce mild acidosis, particularly toward the beginning of treatment, due to adsorption of bicarbonate by the sorbent cartridge 220, where bicarbonate freely diffuses across the dialysis membrane. After the initial loss of bicarbonate to the sorbent cartridge, the sorbent cartridge will add bicarbonate to the dialysate due to hydrogen ion added to the dialysate in exchange for ammonium ions.

In certain embodiments, a bicarbonate cartridge containing sodium bicarbonate or another bicarbonate-containing salt can be provided within the system, where dialysate solution can be diverted through the bicarbonate cartridge 302 as required. As shown in FIGS. 2 and 3, the bicarbonate cartridge 302 is present in the bypass pathway 136 attached to 3-way valve 150, wherein a portion of the dialysate flow can bypass the dialyzer 130 and be passed through the bicarbonate cartridge 302. The bicarbonate cartridge 302 can contain an amount of solid sodium bicarbonate or another bicarbonate-containing salt that is reconstituted to form a saturating solution during a priming cycle, as described below. Changing the state of the 3-way valve 150 will direct flow to the bicarbonate cartridge 302 to release bicarbonate into the system. Valve 150 could alternatively be two two-way valves (not-shown). Dialysate flow can be diverted through the bicarbonate cartridge 302 as needed to adjust the pH of the dialysate. Further, the bicarbonate cartridge 302 at the beginning of treatment can be used to preload the sorbent cartridge 220 so that the bicarbonate level will not significantly decrease at the beginning of treatment due to absorption of bicarbonate ions by the sorbent cartridge 220. In certain other embodiments, the contents of the bicarbonate cartridge 302 is completely dissolved in the priming process rather than forming a saturated solution. The dissolved bicarbonate can then preload the sorbent cartridge 102 at the beginning of treatment to prevent an excessive drop in pH at the beginning of treatment. In certain other embodiments, a bicarbonate containing solution can be added via a bicarbonate pump to a point on the dialysate circuit 241 from a container containing a solution of bicarbonate salt (not shown). The bicarbonate salt is added to the dialysate under the control of controller 801 in order to maintain the concentration of bicarbonate ion within predetermined ranges. The rate of addition can be controlled through several means including monitoring conductance of the dialysate (bicarbonate salts are conductive) or a pH meter to measure the pH of the dialysate.

The portion of the dialysate flow diverted to pass through bicarbonate cartridge 302 can be at a constant rate over the course of treatment in accordance with some embodiments. In certain other embodiments, a pH meter (not shown) can be located within the system to measure the pH of the dialysate within the dialysis circuit 141, where a controller 801 monitoring the pH meter can make appropriate adjustment to the rate of bicarbonate addition to the dialysis circuit 141. The pH meter can be co-located with one of the conductivity meters 101 and/or 104. As will be described below, certain embodiments allow for the amount of urea absorbed by the sorbent cartridge 102 to be quantified by a controller 801. In certain embodiments, the controller 801 can adjust the rate of bicarbonate addition to the dialysis circuit 141 based up the amount of urea calculated to be absorbed by the sorbent cartridge 102, where there is no requirement for the pH of the dialysate to be directly measured.

Priming of the Urea Removal Module

Figure 6:
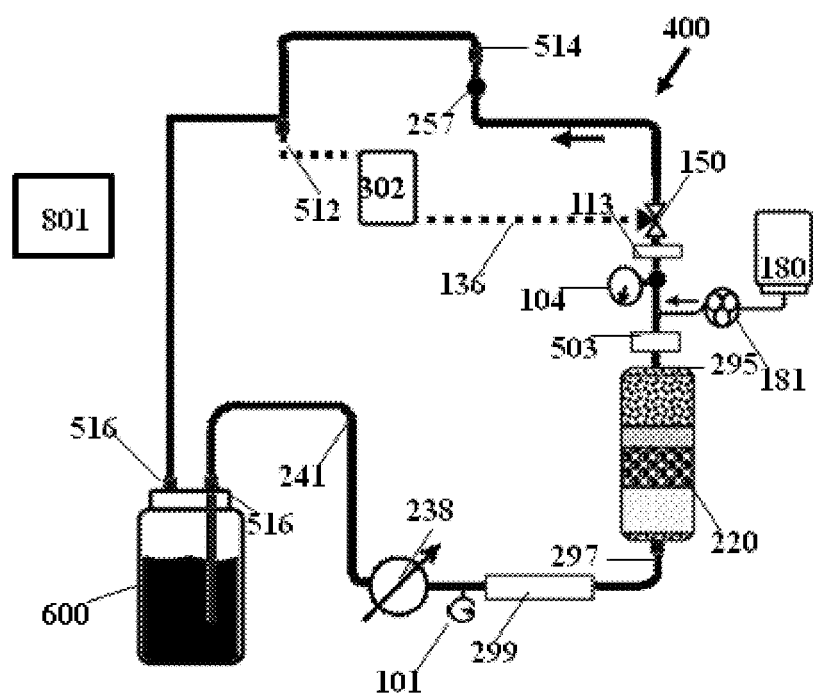
FIG. 6 shows a priming act for a urea removal module in accordance with certain embodiments.

The system including the urea removal module 400 has to be purged of air (i.e. primed) prior to use such that the various pumps function properly and to protect the patient from an air embolism. In certain embodiments, the systems described herein can be primed and prepared for operation through the provision of only one fluid provided in a single container. As shown in FIG. 6, connectors 512 and connectors 514 are connected to each other and connectors 516 are connected to a vessel 600 to form a closed loop for conveying a fluid along the second dialysate circuit 241. The fluid in vessel 600 can be a saline solution, tap water or a physiologically compatible dialysate. If tap water is used, an additional activated carbon material may be placed at the inlet 297 of the sorbent cartridge 220 to remove impurity species such as heavy metals that can be harmful to the urease-containing material. The connectors can be luer connectors.

The dialysate pump 238 is run to push air out of the second dialysis circuit 241 and replace the air with the fluid from vessel 600. The infusate pump 180 can be run to modify the chemical composition of the fluid to make the fluid physiologically compatible. Intermittently, the controller 801 modifies the actuation of valve 150 to divert fluid through the bypass pathway 136 and the bicarbonate cartridge 302. Bicarbonate ions eluted from the bicarbonate cartridge 302 can saturate the zirconium oxide material present within the sorbent cartridge 220. As such, an excessive amount of absorption of bicarbonate ions from the subject's blood at the beginning of treatment can be avoided. When air is removed from the second dialysate circuit 241, the connectors 512 and 514 are attached to the dialyzer 130 to allow dialysate flow through the dialyzer 130. Connectors 516 are reconnected to allow for circulation of dialysate through the dialysis circuit 241 and to attach the control pump 290. In certain embodiments, the dialysis circuit 241 can include a bypass around the sorbent cartridge in order to preserve the zirconium phosphate therein during priming.

The portable treatment module 100 and the extracorporeal circuit 140 can be primed in a similar manner (not shown). For the extracorporeal circuit 140, the ends of the extracorporeal circuit 140 that attach to the subject can be attached to a source of saline and the air flushed from the system by running the blood pump 125 to fill the extracorporeal circuit 140 with saline. When air is removed, the extracorporeal circuit 140 can be attached to the subject. For the portable treatment module 100, the dialysis circuit 141 can be flushed with a physiologically compatible dialysate to remove air, since the dialysis circuit 141 does not have control features to modify the composition of the dialysate. Alternatively, the dialysis circuit 141 can be flushed with a saline solution. Due to the small volume of dialysate used, any fluid placed in the dialysis circuit 141 will come into equilibration with the subject's blood quickly.

Quantization of Urea Removal

The blood of patients undergoing a regime of renal replacement therapy typically undergoes blood chemistry determination by laboratory testing on a periodic basis to determine the effectiveness of treatment. Such testing is undertaken by a trained healthcare professional on a separate basis from the renal replacement therapy. Based upon lab results, various treatment metrics can be adjusted. For a patient utilizing the wearable sorbent system described herein without the aid of a healthcare professional, it is desirable to have a facility to determine the extent of treatment during therapy. A subject only requires use of the urea removal module 400 for the reduction of blood urea levels, after which the subject can return to use of the portable treatment module 100. A facility to quantify the level of urea removal during treatment will facilitate limiting the amount of time that a subject uses the urea removal module 400.

During treatment, the sorbent cartridge acts as a cation exchanger and releases hydrogen and sodium ions. The release of sodium by the sorbent cartridge has two principal sources:

1) Urea is converted to ammonium ions by the urease layer of the sorbent cartridge. The ammonium ions are exchanged to sodium and hydrogen in the zirconium phosphate layer(s) of the sorbent cartridge. The stoichiometry of the amount of sodium given off in this exchange is dependent on the processing of the zirconium phosphate layer; however, each process provides uniform results. Once the stoichiometry of ammonium/hydrogen/sodium exchange is known, the amount of sodium released from the sorbent cartridge can be used to quantify the amount of ammonium ions absorbed. By means of example, a representative example of the zirconium phosphate material can operate to exchange 1 mEq ammonium ion for 0.15 mEq sodium ion and 0.85 mEq hydrogen ion. In this example, if the cartridge removes 20 grams of urea during a treatment, then the zirconium phosphate material removes 1400 mEq ammonium ions, which would produce about 210 mEq of sodium ions. Those skilled in the art will readily recognize that other zirconium phosphate materials having a different stoichiometry of ammonium/hydrogen/sodium exchange can also be used to calculate the amount of urea converted to ammonium ion and absorbed by the sorbent cartridge; and 2) The dialysis solution contains electrolytes such as calcium ($Ca^{2+}$), magnesium ($Mg^{2+}$) and potassium ($K^+$). These electrolytes remain in a stable range and close to constant in the dialysate during treatment. These electrolytes are totally removed from the spent dialysate by the sorbent cartridge 220. To ensure that there is a stable and correct concentration of electrolytes in the refreshed dialysate prior to reaching the dialyzer, zirconium phosphate exchanges these electrolytes with sodium ions. Then, the electrolytes are re-infused via an infusate pump 181 to the correct concentrations. The amount of sodium produced from the zirconium phosphate layer due to this exchange is dependent on the dialysis solution flow rate, the time of treatment and the concentration values of these cations in the dialysis solution. For example, if the $Ca^{2+}$ were 3 mEq, the $Mg^{2+}$ 1 mEq, and the $K^+$ 1 mEq, the sorbent cartridge would produce approximately 240 mEq of sodium at a 20 ml/min flow rate and a total volume of 48 liters through the sorbent cartridge.

Due to the near constant amounts of ($Ca^{2+}$), magnesium ($Mg^{2+}$) and potassium ($K^+$) ions being exchanged by the sorbent cartridge, the conductivity difference between dialysate containing urea entering the sorbent cartridge compared with the refreshed dialysate exiting the sorbent cartridge can be used to quantify the amount of urea converted to ammonium ions and absorbed by the sorbent cartridge. If the temperature and composition of an electrolyte solution are constant, the resulting conductivity of the solution will remain stable. At the ranges of typical dialysis solutions, any change in sodium concentration will result in a linear increase or decrease in dialysate conductivity. Table 1 shows the concentration and conductivity of a typical dialysis solution at 25° C. Even though sodium is not the only contributor to conductivity in dialysis solution, NaCl and NaHCO$_3$ make up approximately 94% of the conductivity of a typical dialysate solution. There is also typically a small amount of acetic or citric acid and dextrose in the solution.

TABLE 1

Composition of a typical dialysate solution and conductivity contributed by individual species.

| Substance | mmol/L | mS/cm |
|---|---|---|
| NaCl | 103 | 10.68 |
| NaHCO$_3$ | 34.0 | 2.47 |
| KCl | 2.00 | 0.26 |
| CaCl | 1.75 | 0.35 |
| MgCl | 0.50 | 0.09 |
| NaCH$_3$COO | 3.00 | 0.21 |
| Total Conductivity 25° C. | | 14.05 |

Sodium concentration increases in the dialysate due to the exchange of ammonium to sodium, which can be used to verify if the urea was removed during the course of treatment. As shown in FIG. 3, conductivity meters 101 and 104 can be incorporated into the system to measure the conductivity of dialysate traveling to the inlet 297 and exiting the outlet 295 of the sorbent cartridge 220. In certain embodiments, a conductivity meter can be present within the sorbent cartridge at the outlet of the zirconium phosphate material. A microprocessor or controller 801 can monitor the conductivity measured by the conductivity meters to analyze the changes in conductivity brought about by the following:
1) Conversion of urease to ammonium carbonate and subsequent exchange of ammonium carbonate to sodium, and
2) Any net change in conductivity due to the exchange of Ca$^{2+}$, Mg$^{2+}$, and K$^+$ into sodium, which can be treated as a constant value. The change due to removal of Ca$^{2+}$, Mg$^{2+}$, and K$^+$ is known and the increase due to sodium is known. In the example dialysis solution of Table 1, the Ca$^{2+}$, Mg$^{2+}$, and K$^+$ contribute 0.7 mS/cm of conductivity.

The change in conductivity due to the loss of Ca$^{2+}$, Mg$^{2+}$, and K$^+$ and the increase of sodium ions due to this exchange will be relatively constant during the treatment. Further, the fraction of the dialysate flow traveling through the deionization cartridge 210 is known and monitored by the controller 801. As described below, the conductivity at the inlet of the sorbent cartridge 220 can be adjusted based upon the amount of diluent eluted from the deionization cartridge 210. That is, the inlet conductivity can be measured at conductivity meter 101 before the addition of a diluent, where the amount conductivity decrease caused by the addition of the diluent is readily calculated. As such, the controller 801 can readily calculate the change in conductivity that is the result or urea absorption by the sorbent cartridge 220. It should be noted that deionization cartridge 210 is an optional component; no adjustment is needed where deionization cartridge 210 is not present. The inlet conductivity is measured at a point on the dialysate circuit 241 between the dialysate outlet 196 and the sorbent cartridge 220. The outlet conductivity is measured at a point between the sorbent cartridge 220 and the dialysate inlet 196. From this information, controller 801 can then calculate the amount of conductivity increase due to the urea removal via the following sources:

Measured Inlet Conductivity−Conductivity Contribution of Ca$^{2+}$, Mg$^{2+}$, and K$^+$−decrease in conductivity caused by diluent=Starting Conductivity Outlet Conductivity−Increase in Conductivity due to exchange of Ca$^{2+}$, Mg$^{2+}$, and K$^+$ to Na$^+$=Corrected Outlet Conductivity Corrected Outlet Conductivity−Starting Conductivity=Conductivity Increase due to Conversion of NH$_4^+$ to Na$^+$ The following example quantization is based upon 48 liters of regenerated dialysis solution used during the course of treatment having typical concentrations of Ca$^{2+}$, Mg$^{2+}$, and K$^+$, where 100% of the dialysate flow bypasses the deionization cartridge 210:
Inlet Conductivity=14.04 mS/cm Outlet Conductivity=14.32 mS/cm
1. 14.05 mS/cm−0.7 mS/cm=13.35 mS/cm Starting Conductivity
2. 14.32 mS/cm−0.5 mS/cm=13.8 mS/cm Corrected Outlet Conductivity
3. 13.8 mS/cm−13.35 mS/cm=0.45 mS/cm Conductivity Increase due to Conversion of NH$_4^+$ to Na$^+$
4. 0.45 mS/cm/0.1037 mS·L/mEq·cm=4.34 mEq/L Na$^+$ due to Urea Removal
5. 0.4 g urea per liter In hemodialysis, urea removal depends on the diffusive gradient across the dialyzer membrane. This gradient will be much higher at the beginning of treatment than at the end of treatment when typically 50 to 60 percent of the patient's urea has been removed. In certain embodiments, the conductivity values can be averaged so the curve of urea removal is understood and a continuous calculation need not be made. For example, conductivity can be sampled four or five times per treatment session for the purposes of quantifying urea removal. Early during a treatment session, a quantization of urea removal can be performed to verify that urea is being removed and that the Na$^+$ increase is relatively high. Later, quantization measurements can be performed to calculate a curve for urea removal and to predict total expected urea removal based on this curve. As such, the amount of urea removed during treatment can be either accurately measured or estimated with a high degree of certainty.

Further, the curve for urea removal can be used to estimate the urea content remaining in the subject's blood to indicate an appropriate time to discontinue treatment with the urea removal module 400. The correspondence to the rate of urea removal and urea content of the subject's blood depends on several factors including the conveyance rate of the dialysate and the blood, performance properties of the dialysis membrane 135 and physiological characteristics of the subject. The curve for urea removal can be used to estimate the urea content of the subject's blood or the controller 801 can be calibrated for a specific individual subject. The controller 801 can signal the subject or another individual when a sufficient amount of urea has been removed to allow return to use of the portable treatment module 100.

Detection of Significant Clearance Problems

The urea removal monitoring facility described above can be used to indicate the proper operation of the system and to alert the patient to significant problems that would interrupt the waste removal process. Problems can be communicated automatically via WiFi, the internet, or other communication means to the doctor or healthcare professional. For instance a patient with impaired blood access flow would have little urea removed. In instances where low urea removed is monitored toward the beginning of treatment, an alarm can be communicated indicating a potential malfunction.

Access to the patient's vasculature can fail due to a buildup of plaque in the access stent. This plaque creates a stenosis at the distal end of the anastomosis where the stent or graft is sutured to the vascular system of the patient. When this occurs, the blood tends to recirculate within the access area and there is a lack of adequate flow of fresh blood into the extracorporeal circuit, which can result in the same blood being repeatedly dialyzed. Since little blood entering the dialyzer is from the systemic circulation, there is less urea in the blood and hence less sodium is produced from the cartridge due to urea/ammonium to sodium exchange. The lack of an adequate increase in conductivity can be detected by the system and an alert can be sent indicating a potential malfunction or problem accessing the patient's vascular system. This alert can indicate a lowered waste clearance, but the alert does not necessarily specify if the cause of the lowered waste clearance is due to a vascular access problem or due to a problem in dialysis flow, etc. A skilled medical professional can analyze the event to determine the cause of the alert in some embodiments.

Detection of Zirconium Exhaustion

After an extended period of use, the ability of the zirconium phosphate to adsorb urea can be exhausted. Exhaustion of zirconium phosphate leads to ammonium release into the dialysate, which can lead to ammonium intoxication in the patient. As discussed above, the exchange of urea/ammonium to sodium affects the output conductivity of the sorbent cartridge. Monitoring the inlet and outlet conductivities of the cartridge thus provides a method to detect ammonium breakthrough in the sorbent cartridge. An equilibration of the sorbent cartridge inlet conductivity with the output conductivity over a short time period indicates that the zirconium phosphate layer within the sorbent cartridge is exhausted. In certain embodiments, the conductivities pre- and post-sorbent cartridges are monitored. If an increase in sodium concentration is not detected by the controller, then the system will send an alert and prevent the dialysate from reaching the dialyzer, thus protecting the patient from ammonia intoxication.

Detection of Patient Hydration Status

The portable dialysis described herein can be used to perform ultrafiltration on a patient. During ultrafiltration, fluid is drawn out from the serum of the blood in the extracorporeal circuit through the dialysis membrane 135 or hemofiltration membrane 200 by means of the control/filtration pump 190/193/290. Fluid removed by the control/filtration pump 190/193/290 is removed to the first control or storage reservoir 192/292, depending upon the use of the portable treatment modules 100 or 301 or the urea removal module 400. Ultrafiltration can be performed alone or in conjunction with convective clearance, as described above. The patient hydration status can be monitored during use of any of the portable treatment module 100 and 301 and the urea removal module 400.

Patients having kidney failure may have an undesirable accumulation of fluid in body tissues that is called edema. As fluid (e.g. water) is removed from the patient's plasma, the volume of the patient's plasma is replaced by infusion of fluid from the patient's tissues. The portable dialysis system does not directly access fluids stored in the patient generally but only directly accesses the patient's vascular system. Humans typically only have 5 to 6 L of plasma volume at any one time, where a significant time lapse can be required for plasma volume to be replaced by transfer to fluid from surrounding tissues.

During ultrafiltration, fluid can be removed too rapidly resulting in the patient becoming hypovolemic, which can cause several serious effects including hypotension, cramping, nausea and vomiting. To avoid instances of hemoconcentration due to excessive fluid removal, the rate of ultrafiltration is limited to a percentage of the blood flow through the extracorporeal circuit 140. In certain embodiments, the rate of ultrafiltration is limited to be no greater than about 30% of the plasma flow through the extracorporeal circuit 140. Plasma flow (Qp) is defined as $Qp=$Blood flow rate$\times$(1-hematocrit), where blood flow rate is in units of volume divided by time (e.g. mL/min) and hematocrit is the unitless fraction of blood volume occupied by red blood cells. For example, if the blood flow rate is 60 mL/min and the hematocrit is 40%, then the maximum rate of ultrafiltration is set to be equal to about 10.8 mL/min or less.

The portable dialysis system can have a hematocrit detector to determine the hematocrit of blood containing within the extracorporeal circuit 140 of FIG. 1. In certain embodiments, the hematocrit detector is a light source and a photodetector, wherein light emanating from the light source is passed through the blood in the extracorporeal circuit 140 and detected by the photodetector. The absorption of one or more wavelengths of light can indicate the level of hematocrit in blood entering the dialyzer 130 in the arterial line 620. In certain embodiments, the hematocrit detector gives an indication if the hematocrit trend is unsafe rather than giving a precise numerical quantification. In certain additional embodiments, the hematocrit detector can also determine if blood is present in the extracorporeal circuit 140, which can be useful during the processes of priming the system or returning blood to the patient as described above. A simple optical detector with a light source and a photodetector can also be used to detect whether there is blood in the system.

In most renal diseases, the kidneys fail to produce erythropoietin, a hormone that stimulates red blood cell production. Most ESRD patients take an erythropoietin stimulation drug to help produce red blood cells. These drugs are dosed to maintain a pre-treatment serum hematocrit of 32%. During the course of the dialysis treatment, the hematocrit can change due to the removal of fluid from the blood. Hematocrit level changes over the course of the treatment are an indication of relative blood volume changes over treatment. Fluid removal by ultrafiltration removes fluid from the blood plasma; however, red blood cells are left in the circulatory system. Depending on the rate of vascular fluid refilling from the tissues, the hematocrit will increase or decrease. A flat hematocrit indicates that the patient is most likely fluid overloaded even at the end of therapy. A steep increase in the slope of the hematocrit during fluid removal may portend a hypovolemic event prior to initiating a hypotensive episode. A gradual increase in hematocrit during the course of treatment is most likely indicative of a well-dialyzed patient.

Figure 7:
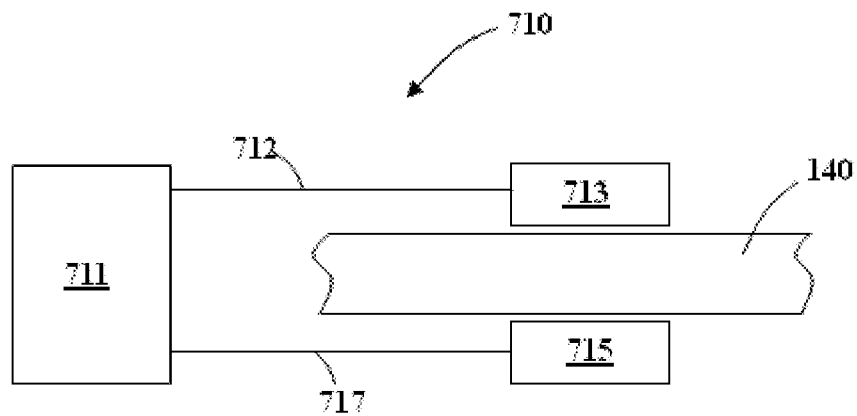
FIG. 7 shows a schematic for a hematocrit or relative blood volume detector.

Hematocrit level is proportional to hemoglobin concentration. Therefore, any suitable sensor can be used to measure hemoglobin concentration, such as sensors used in pulse oximeters which measure adsorption of red and infrared light to determine concentration of oxygenated hemoglobin and deoxyhemoglobin, respectfully. The hematocrit/hemoglobin sensors, which may include the associated light source(s), can be placed in any suitable location. Placement of the hematocrit/hemoglobin sensor along the arterial line 610 of the extracorporeal circuit 140 will indicate the status of blood volume within the circulation of the patient. Placement of the hematocrit/hemoglobin sensor along the venous line 620 of the extracorporeal circuit 140 will indicate the extent of hemoconcentration occurring within the dialyzer 130. Measurement of hematocrit within the arterial line 610 can be used to calculate Qp as described above. Other optical based technologies that can determine the relative blood volume changes during the course of treatment can also be used to determine hydration status of the patient and whether the appropriate amount of fluid has been removed FIG. 7 shows a schematic for a hematocrit/hemoglobin/relative blood volume sensor 710. A light source 713 of appropriate wavelength (red or infrared) is positioned on one side of the tubing of extracorporeal circuit 140 such that the light passing through tubing hits detector 715. More light is absorbed (and less hits the detector 715) if a higher concentration of hemoglobin is present in the extracorporeal circuit 140. A lead 712 carries power and other electrical signals, if appropriate, to the light source 713 from the sensor device body 711, which may contain the power source and other control or detecting electronics. Lead 717 carries electrical signals from detector 715 to the components housed in sensor device body 711. Suitable hematocrit sensors are known, such as a CRIT-LINE monitor from HEMAMETRICS (see, HEMAMETRICS, CRIT-LINE hematocrit accuracy, Vol. 1, Techn Note No. 11 (Rev. D) Feb. 24, 2003). The detector shown in FIG. 7 can be co-located with air-fluid detector 133 or 134 or at another suitable location along the arterial line 610 on the extracorporeal circuit 140 of any embodiment described herein.

In other embodiments, hemoconcentration and blood hydration status can be detected and monitored by a relative blood volume monitor. The relative blood volume monitor can detect a change in the concentration of measured solutes, solid materials or a group of solutes and solid materials in the blood that are too large to cross the dialysis membrane 135 or hemofiltration 200 membranes, which indicates a change in blood volume. The volume of blood typically is not measured by the relative blood volume monitor directly. The relative blood volume monitor measures the change in water content of the blood over the course of treatment, as implicated by a relative change in solute content, and does not require an absolute quantization of any particular solute in the blood. The relative blood volume monitor determines the relative blood volume hydration status (RBVHS) of the subject by measuring the level of one or more blood solutes at a time close to the beginning of treatment, which can be assigned a value $C_0$. The level of the one or more blood solutes does not require an absolute quantification; rather the level of the one or more blood solutes can be reported as the magnitude of a signal generated by the relative blood volume monitor. The level of the one or more solutes is measured periodically at a second later time, which can be assigned a value $C_t$. The relative blood volume hydration status can then be determined by the formula RBVHS=$C_0$/$C_t$.

In certain embodiments, the relative blood volume monitor is a hematocrit sensor and the one or more solutes measured by the relative blood volume monitor are oxygenated or deoxygenated hemoglobin. In certain other embodiments, the relative blood volume monitor is a device that measures the velocity of ultrasonic sound waves in the blood. Ultrasonic sound waves are defined as sound waves having a frequency above 20,000 Hz. The velocity of ultrasonic sound waves in blood is an indication of the total protein concentration in the blood.

The relative blood volume hydration status can be used in the same manner as hematocrit, described above, to determine the effectiveness of ultrafiltration. It is important to note that when using relative blood volume the trend slope is inverse to the trend slope when using a hematocrit sensor, i.e. as hematocrit increases, relative blood volume decreases. A flat relative blood volume hydration status indicates that the patient is most likely fluid overloaded even at the end of therapy. A steep decrease in the slope of the relative blood volume hydration status during fluid removal can portend a hypovolemic event prior to initiating a hypotensive episode. A gradual decrease in relative blood volume hydration status during the course of treatment is most likely a well-dialyzed patient. In certain further embodiments, the relative blood volume hydration status determined by the relative blood volume monitor can be correlated to a fluid volume of the blood.

In the event that an unsafe level of hydration status is indicated by hematocrit level or by relative hydration status, a controller 801 associated with the system can stop the fluid removal and alert the patient. Controller 801 can also be programmed to remove fluid via a gradual slope in relative blood volume or hematocrit. Additionally, the controlled compliant nature of the dialysis circuit can be used to administer a bolus transfer of fluid to the patient. As described above, operation of the control pump 190 or 290 in the influx direction will cause a transfer of fluid volume from the first control reservoir 192 or 292 to the extracorporeal circuit 140. The system can be preprogrammed to transfer a certain bolus volume to the patient upon detection of an unsafe trend in hematocrit or relative blood volume hydration status.

In certain embodiments, the first control reservoir 192 or 292 is empty at the beginning of a treatment session wherein volume enters the control reservoir during treatment including ultrafiltration. As such, a bolus infusion in response to trend in hematocrit or relative blood volume hydration status is a return of fluid volume removed from the patient during treatment back to the patient. Any volume returned to the patient from the first control reservoir 192 or 292 is cleaned by the sorbent cartridge 102 or 220 prior to introduction to the extracorporeal circuit 140. However, in other embodiments the first control reservoir 192 or 292 can contain a volume of fluid at the beginning of treatment that can be used for a net infusion of fluid into the patient during the course of treatment.

Figure 8:
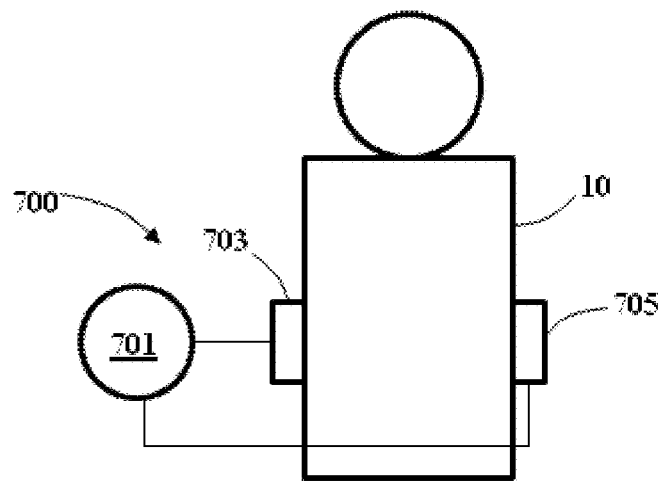
FIG. 8 shows a schematic for an impedance detector.

Hypovolemia can further be guarded against by simultaneously monitoring body fluid level of the patient undergoing hemodialysis treatment. The amount of fluid stored in body tissues outside the blood is proportional to the impedance that can be measured from the patient's body. As depicted in FIG. 8, impedance can be monitored between two electrodes 703 and 705 that are attached to the torso 10 of a human patient. The electrodes 703 and 705 are operably coupled to control and processing electronics 701 via leads. The electronics 701 are configured to generate a voltage differential between the electrodes 703 and 705, and current can be measured and impedance calculated. The measurement can be done in either DC or AC mode. Impedance or phase angle can be correlated to tissue fluid volume. Suitable external impedance monitors 700 and components that can be used in accordance with the teachings described herein are known. In certain other embodiments, electrodes 703 and 705 can be implanted within the patient.

One example of a well studied system that can be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., Siegenthalar, et al. Journal of Clinical Monitoring and Computing (2010): 24:449-451, and Wang, Am. J. Cardiology, 99(Suppl):3G-1-G, May 21, 2007. Alternatively or in addition, tissue impedance can be monitored for a suitable period of time to establish as suitable baseline, and patient markers can be used to instruct whether the patient is fluid overloaded or under-loaded. The data acquired by impedance sensor and input data regarding fluid status of the patient at the time the sensor data is acquired may be used to establish suitable ranges for impedance values.

One or more controllers 801 associated with the hemodialysis system can monitor the hematocrit/relative blood volume hydration status and impedance/body fluid level of the patient undergoing hemodialysis treatment. A typical hematocrit level for a dialysis patient is about 32%. Prior to a treatment session, the fluid volume of blood of a kidney disease patient can be elevated, thus hematocrit levels can be lower than desired The one or more controllers 801 monitoring hematocrit levels can adjust the rate of fluid removal or end ultrafiltration treatment when hematocrit level reaches the desired, predetermined range.

Fluid within a person's body is capable of moving from the body tissue to the blood and vice versa. As such, proper fluid levels in a patient can be described in terms of a ratio of tissue fluid to blood volume, as measured by hematocrit level. Hematocrit level of body fluid level can be monitored independently as described above. In general, blood is about 7% of body weight and total tissue fluid is about 60% of the body weight (including blood, extracellular and intracellular fluid). As such, a typical tissue fluid to blood fluid volume ratio of a healthy individual is in the range from about 6:1 to about 9:1. A measured ratio above this range indicates that blood is being withdrawn too quickly to allow for adequate equilibration of fluid between the blood and tissues of the patient. Fluid removal can be modified, stopped, or a fluid bolus administered as appropriate and preprogrammed into the one or more controllers 801 of the hemodialysis system.

Detection of Needle or Catheter Disconnection

It is well established in the art that pressure is not always a reliable means to detect separations of the venous blood return from the access of the patient. If this event occurs there is the risk of a life threatening blood loss and possible exsanguination. A conductive mat or holder can be used to detect blood leaks to the controller. The controller can then take the appropriate means to protect the patient by stopping the blood pump and alerting the patient. Other means to detect needle or catheter disconnections can be incorporated into the system such as monitoring of the impedance through the two needles or using pressure pulses.

System Control

As described above, the systems described herein have several dynamic components including pumps and valves as well as detectors that determine the state of the system. As applied throughout this disclosure, operation of the system under the control of controller can refer to a single controller or multiple controllers having separate or overlapping function. A controller refers to a device having a programmable microprocessor and associated memory.

Figure 9:
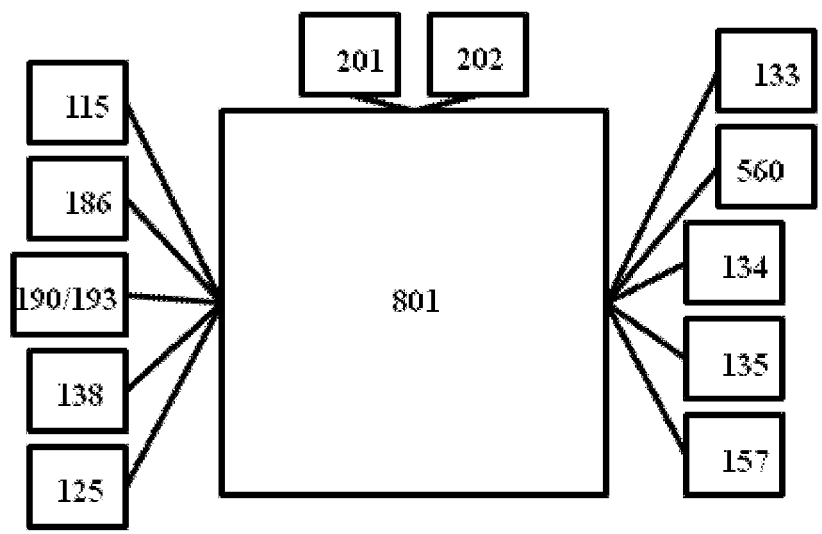
FIG. 9 shows a schematic for a controller in communication with various system components including a portable treatment module.

FIG. 9 shows one or more controllers 801 capable of sending and receiving data or instructions from several system components of a system including the portable treatment module 100. The one or more controllers 801 can be more than one microprocessor unit. As discussed, the control of the system including the portable treatment module 100 is minimized due to the lack of need to control conductivity and/or pH. Specifically, the one or more controllers 801 are capable of controlling the pump rate and pumping direction of the blood pump 125, the dialysate pump 138 and the control/filtration pump 190 or 193. The operation of anticoagulant pump 186 is further under control of the one or more controllers 801. In two controller systems one controller may be used to control the process and the other controller may be used to monitor the system and protect if the control is not correct.

The one or more controllers 801 also receives data from the various meters and detectors incorporated in the system including pressure meters 134, 135, and 157, optical and/or air-fluid detectors 201 and 202 and blood leak detector 560. The one or more controllers 801 are capable of stopping or modifying operation of the system to protect the patient from an unsafe pressure reading indicating a malfunction or the presences of air in the extracorporeal circuit 140 or detection of a blood leak in the dialyzer 130, as detected by blood leak detector 560. Further, the one or more controllers 801 can modify or stop the operation of the system based upon an abnormal pressure reading or a detected leak.

Figure 10:
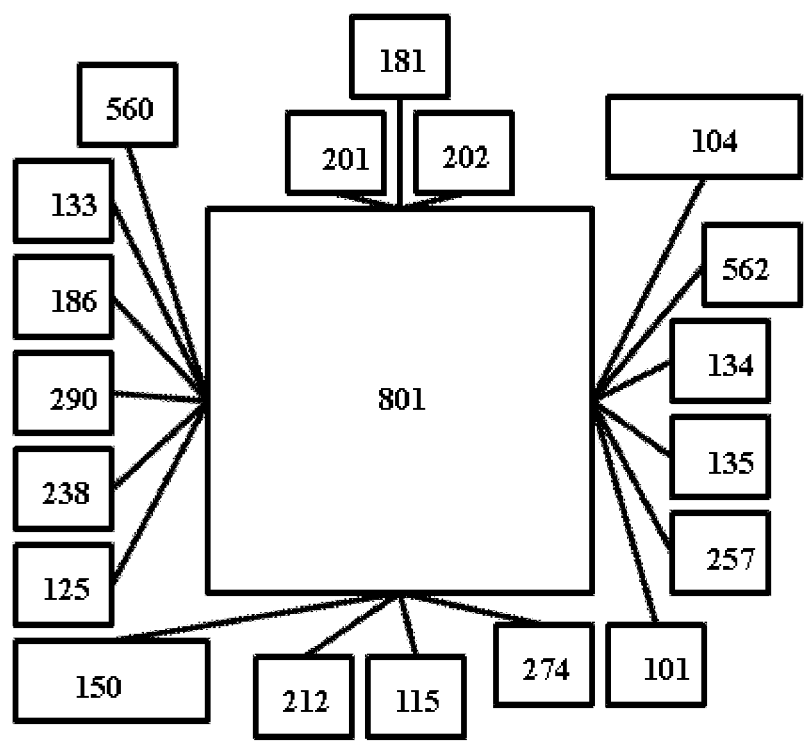
FIG. 10 shows a schematic for a controller in communication with various system components including a urea removal module.

FIG. 10 shows the same controller 801 as in FIGS. 1-4 configured to operate in conjunction with a system having the urea removal module 400. The one or more controllers 801 are capable of controlling the pump rate and pumping direction of the blood pump 125, the dialysate pump 238, optional pump 274 and the control pump 290 along with the operating of valve 150. The operation of heparin pump 186 and infusate pump 181 is further under control of the one or more controllers 801.

The one or more controllers 801 also receives data from the various meters and detectors incorporated in the system including pressure meters 134, 135, and 257, optical and/or air-fluid detectors 201 and 202, conductivity meters 101 and 104 and blood leak detector 562. The one or more controllers 801 are capable of stopping or modifying operation of the system to protect the patient from an unsafe pressure reading indicating a malfunction or the presences of air in the extracorporeal circuit 140, an unsafe conductivity level or detection of a blood leak in the dialyzer 130. The one or more controllers are capable of stopping any of the pumps of the systems or operating valve 150 to bypass the dialyzer 130. Further, the one or more controllers 801 can modify or stop the operation of the system based upon the conductivity readings from the conductivity meters 101 and 104 as well as calculating an amount of urea absorption by the sorbent cartridge 220.

By locating one or more of the controllers 801 remote from the portable dialysis system, the majority of processing power does not have be carried by the patient thereby lowering the weight of the device. Devices and methods for controlling a device through wireless technology are known in the art. The wireless signals can employ signal confirmation, digital encoding algorithms, checksums and other verifications to minimize the effects of interference and to allow similar systems to operate in the same area. The system can have a safety feature to stop the device if the wireless control signal is interrupted or compromised.

It will be apparent to one skilled in the art that various combinations and/or modifications and variations can be made to the portable dialysis system depending upon the specific needs for operation. Moreover, features illustrated or described as being part of one embodiment may be used on another embodiment to yield a still further embodiment.

Further Applications and Uses

One having skill in the art will readily recognize that the innovations disclosed herein are not limited to any specific application including not being limited to medical treatment. For example, the innovations disclosed herein relate to the control of fluid movement between two circuits under conditions where pressure and flow rates are necessarily well controlled. Systems having a controlled compliance dialysis circuit 141 and an additional circuit without a requirement for specifically controlled compliance (e.g. extracorporeal circuit 140) can be applied to any application where membrane-based diffusion or purification is applied. Further, the systems disclosed herein describe the use of a modular system for the selective application of a sorbent or a specific sorbent during operation of the system such that the manner of purification can be adjusted over time without disruption or disconnection from the fluid undergoing purification.

Those skilled in the art will understand that extracorporeal circuit 140 can be substituted with another external circuit 140 for circulating any suitable external fluid for purification, wherein the volume of fluid transferred between the external fluid and the fluid in the dialysis circuit 141 can be controlled. For example, the described systems can be applied to buffer exchange for pharmaceutical compositions, such as aqueous suspensions of biomolecules including oligonucleotides, proteins, and/or peptides, etc. Specifically, the circuit 140 can be adapted to be an external circuit 140 that is configured to circulate a pharmaceutical composition containing a solution or suspension of biomolecules. Concentrating a solution or suspension containing biomolecules is often problematic; however, it is often a requirement for pharmaceutical compositions to be provided at very specific concentrations. A common procedure for concentrating such solutions and suspensions is ultrafiltration, where a solution or suspension of biomolecules is contacted with an ultrafiltration membrane with centrifugal force used to drive water through the ultrafiltration membrane to generate a more concentrated solution or suspension. However, ultrafiltration is expensive and often solubility problems develop during the process where expensive biomolecules are lost during the process. As such, once a solution or suspension of biomolecules is prepared at a desired concentration, it is advantageous to avoid further changes in concentration.

An external fluid being a solution or suspension of biomolecules in a first buffer can be provided and conveyed through the external circuit 140. A second buffer can be provided and conveyed in the dialysis circuit 141. The movement of fluid across the dialyzer 130 can be prevented to maintain the concentration of the solution or suspension of biomolecules during buffer exchange or the volume otherwise controlled. Dependent upon the nature or stage of the buffer exchange, the module containing the dialysis circuit 141 can be exchanged without disturbing the external circuit 140. For example, during some stages of buffer exchange or purification, the use of a sorbent cartridge that removes all ionic components (e.g. a mixed anion/cation exchange resin) may be advantageous. During other stages of buffer exchange or purification, a sorbent targeted to specific organic or biomolecule impurities may be advantageous through use of a different module and sorbent cartridge serving as the dialysis circuit 141.

The invention claimed is:

1. A system comprising:
  an extracorporeal module, an attachable portable treatment module, an attachable urea removal module, and one or more controllers;
  the extracorporeal module comprising
    an extracorporeal circuit comprising
      a dialyzer having a dialysis membrane, a blood inlet, a blood outlet, a dialysate inlet, and a dialysate outlet;
      a blood pump that pumps blood from a subject through the extracorporeal circuit; and
      one or more attachments for fluidly connecting to the blood inlet and the blood outlet;
  the portable treatment module comprising
    a first dialysis circuit comprising
      a first sorbent cartridge, with the proviso that the first sorbent cartridge does not contain urease;
      one or more first control pumps;
      a first control reservoir;
      a first dialysate pump for conveying a dialysate from the first sorbent cartridge to the dialyzer and back to the first sorbent cartridge; and
      one or more first connectors for attaching the first dialysis circuit to the dialysate inlet and the dialysate outlet of the dialyzer;
  the urea removal module comprising
    a second dialysis circuit comprising
      a second sorbent cartridge comprising urease;
      one or more second control pumps;
      one or more second control reservoirs;
      a second dialysate pump for conveying a dialysate from the second sorbent cartridge to the dialyzer and back to the second sorbent cartridge; and
      one or more second connectors for attaching the second dialysis circuit to the dialysate inlet and the dialysate outlet of the dialyzer;
  wherein, at any given time, only one of the portable treatment module and the urea removal module is attached to the dialyzer;
  wherein both the portable treatment module and the urea removal module are controlled compliant;
  wherein the one or more first control pumps are configured to provide selective adjustment of the volume of the first dialysis circuit by
    (A) operating in an influx direction so that fluid moves from the first control reservoir to the first dialysis circuit; and
    (B) operating in an efflux direction so that fluid moves from the first dialysis circuit into the first control reservoir;
  wherein the one or more second control pumps are configured to provide selective adjustment of the volume of the second dialysis circuit by
    (C) operating in an influx direction so that fluid moves from the one or more second control reservoirs to the second dialysis circuit; and
    (D) operating in an efflux direction so that fluid moves from the second dialysis circuit into the one or more second control reservoirs;
  wherein controlled compliance of the portable treatment module is achieved by actively controlling, via the one or more controllers, the influx and efflux of fluid to and from both the first dialysis circuit and the extracorporeal circuit;
  wherein controlled compliance of the urea removal module is achieved by actively controlling, via the one or more controllers, the influx and efflux of fluid to and from both the second dialysis circuit and the extracorporeal circuit;
  wherein when the portable treatment module is attached to the dialyzer, the volume of fluid in the first dialysis circuit, once the system is in operation, is substantially constant;

wherein when the urea removal module is attached to the dialyzer, the volume of fluid in the second dialysis circuit, once the system is in operation, is substantially constant;

wherein when either the portable treatment module or the urea removal module is attached to the dialyzer, the system provides fluid balancing without the use of scales or gravimetric methods.

2. The system of claim 1, wherein the first sorbent cartridge consists essentially of activated carbon and zirconium oxide.

3. The system of claim 2, wherein the volume of fluid removed from the first dialysis circuit by the one or more first control pumps is substantially the same volume of fluid transferred from the body of the subject to the portable module.

4. The system of claim 2, with the proviso the first dialysate pump is not a pulsatile pump.

5. The system of claim 2, wherein a void volume space for accommodating the dialysate in the first sorbent cartridge, the dialyzer, and conduits comprising the first dialysis circuit has a substantially inflexible volume.

6. The system of claim 2, wherein the one or more controllers control operation of the one or more first control pumps to intermittently switch between an efflux direction to move fluid across the dialysis membrane from the extracorporeal circuit to the first dialysis circuit and an influx direction to move fluid across the dialysis membrane from the first dialysis circuit to the extracorporeal circuit.

7. The system of claim 2, wherein the one or more controllers control a ratio of a rate of blood flow through the dialyzer and a rate of dialysate through the dialyzer to be from about 1:1.5 to about 3:1.

8. A modular system for ultrafiltration, comprising:
an extracorporeal circuit, an attachable portable module, an attachable urea removal module, and one or more controllers;
the extracorporeal circuit comprising
a hemofilter having a hemofiltration membrane, a blood inlet, a blood outlet, an ultrafiltrate outlet, and a second port, the second port remaining sealed during operation of the portable module;
a blood pump for pumping blood from a subject through the extracorporeal circuit; and
one or more attachments for fluidly connecting to the blood inlet and the blood outlet;
the portable module comprising
a filtrate pump for applying a negative pressure to the hemofilter to cause ultrafiltrate to pass through the ultrafiltrate outlet;
a first control reservoir; and
a first connector for attaching the portable module to the ultrafiltrate outlet of the hemofilter;
the urea removal module comprising
a dialysis circuit comprising
a sorbent cartridge comprising urease;
one or more control pumps;
one or more second control reservoirs;
a dialysate pump for conveying a dialysate from the sorbent cartridge to the hemofilter and back to the sorbent cartridge; and
one or more second connectors for attaching the dialysis circuit to the ultrafiltrate outlet and to the second port;
wherein, at any given time, only one of the portable module and the urea removal module is attached to the hemofilter;

wherein the urea removal module is controlled compliant;
wherein the one or more control pumps are configured to provide selective adjustment of the volume of the dialysis circuit by
(A) operating in an influx direction so that fluid moves from the one or more second control reservoirs to the dialysis circuit; and
(B) operating in an efflux direction so that fluid moves from the dialysis circuit into the one or more second control reservoirs;
wherein controlled compliance of the urea removal module is achieved by actively controlling, via the one or more controllers, the influx and efflux of fluid to and from both the dialysis circuit and the extracorporeal circuit;
wherein when the urea removal module is attached to the hemofilter, the volume of fluid in the dialysis circuit, once the system is in operation, is substantially constant;
wherein when the urea removal module is attached to the hemofilter, the system provides fluid balancing without the use of scales or gravimetric methods.

9. The system of claim 8, further comprising a relative blood volume monitor to determine the relative blood volume hydration status (RBVHS) of the blood in the extracorporeal circuit, the relative blood volume monitor configured to send information to the one or more controllers to control the rate of the filtrate pump, wherein the relative blood volume monitor determines the level ($C_0$) of one or more solutes in the blood at a first time and determines the level ($C_t$) of the one or more solutes in the blood at a second time later than the first time, and the relative blood volume hydration status is calculated by the formula RBVHS=$C_0/C_t$.

10. The system of claim 8, with the proviso that the attachable portable module does not have a sorbent for absorbing a waste species.

11. A method comprising:
attaching the vasculature of a patient to an extracorporeal circuit having a first end that draws blood from the patient, a second end that returns blood to the patient, and a dialyzer having a single blood inlet, a single blood outlet, a single dialysate inlet, a single dialysate outlet, and a dialysis membrane;
attaching the dialysate inlet and dialysate outlet of the dialyzer to a controlled compliant portable module, the portable module comprising a first sorbent cartridge having activated carbon therein, the portable module further comprising a first dialysis circuit and one or more first connectors for attaching the first dialysis circuit to the dialysate inlet and dialysate outlet of the dialyzer; wherein the first dialysis circuit comprises one or more first control pumps and a first control reservoir, the one or more first control pumps configured to be controlled by one or more controllers;
conveying blood from the patient through the extracorporeal circuit and the dialyzer and returning blood to the patient;
conveying dialysate through the first dialysis circuit such that the dialysate moves from the first sorbent cartridge to the dialyzer and back to the first sorbent cartridge wherein the blood and the dialysate are in fluid communication through the dialysis membrane and one or more waste species move from the blood to the dialysate;

removing the one or more waste species from the blood of the patient for a first period of time wherein the one or more waste species are absorbed by the first sorbent cartridge;

wherein the one or more first control pumps are configured to provide selective adjustment of the volume of the first dialysis circuit by (A) operating in an influx direction so that fluid moves from the first control reservoir to the first dialysis circuit; and (B) operating in an efflux direction so that fluid moves from the first dialysis circuit into the first control reservoir;

wherein controlled compliance of the portable module is achieved by actively controlling, via one or more controllers, the influx and efflux of fluid to and from both the first dialysis circuit and the extracorporeal circuit, without the use of scales or gravimetric methods;

disconnecting the dialysate inlet and dialysate outlet from the portable module;

attaching the dialysate inlet and dialysate outlet to a controlled compliant urea removal module, the urea removal module comprising a second sorbent cartridge having at least urease and zirconium phosphate or magnesium phosphate therein, the urea removal module further comprising a second dialysis circuit and one or more second connectors for attaching the second dialysis circuit to the dialysate inlet and the dialysate outlet;

wherein the second dialysis circuit comprises one or more second control reservoirs and one or more second control pumps, the one or more second control pumps configured to be controlled by the one or more controllers;

conveying dialysate through the second dialysis circuit such that the dialysate moves from the second sorbent cartridge to the dialyzer and back to the second sorbent cartridge, wherein the blood and the dialysate are in fluid communication through the dialysis membrane and urea diffuses from the blood to the dialysate;

removing urea from the dialysate during the second period of time wherein the urea is removed by the second sorbent cartridge;

wherein the one or more second control pumps are configured to provide selective adjustment of the volume of the second dialysis circuit by (C) operating in an influx direction so that fluid moves from the one or more second control reservoirs to the second dialysis circuit; and (D) operating in an efflux direction so that fluid moves from the second dialysis circuit into the one or more second control reservoirs;

wherein controlled compliance of the urea removal module is achieved by actively controlling, via the one or more controllers, the influx and efflux of fluid to and from both the second dialysis circuit and the extracorporeal circuit, without the use of scales or gravimetric methods.

12. The method of claim 11, further comprising monitoring the conductivity of the dialysate at a location between the dialyzer and an inlet end of the second sorbent cartridge with a first conductivity meter;

monitoring the conductivity of the dialysate at a position between an outlet end of the second sorbent cartridge and the dialyzer with a second conductivity meter; and calculating an amount of urea absorbed by the second sorbent cartridge based at least in part upon the conductivity measured at the inlet end of the second sorbent cartridge and at the outlet end of the second sorbent cartridge.

13. The method of claim 11, further comprising operating either the first control pump or the second control pump that adds fluid from a control reservoir to the first or second dialysis circuit in an influx direction via a conduit or removes fluid from the first or second dialysis circuit to the control reservoir in an efflux direction via the conduit, and intermittently switching the first control pump or second control pump between the efflux direction to move fluid across the dialysis membrane from the extracorporeal circuit to the first or second dialysis circuit and the influx direction to move fluid across the dialysis membrane from the first or second dialysis circuit to the extracorporeal circuit, wherein the intermittent switching of the pump accomplishes the convective clearance of at least one waste species having a molecular weight less than about 66000 g/mol and greater than about 1000 g/mol.

14. The method of claim 13, wherein the first control pump or second control pump operates to pump a larger volume in the efflux direction compared with the influx direction over a period of time.

15. The method of claim 13, wherein the first control pump or second control pump operates to pump a volume in the efflux direction that is at least about 10% greater compared to a volume pumped in the influx direction over a period of time.

16. A method comprising:

attaching the vasculature of a patient to an extracorporeal circuit having a first end that draws blood from the patient, a second end that returns blood to the patient, and a hemofilter, said hemofilter having a hemofiltration membrane, a blood inlet, a blood outlet, an ultrafiltrate outlet, and a second port;

attaching the ultrafiltrate outlet of the hemofilter to a portable module, the portable module comprising a filtrate pump for applying a negative pressure to the hemofilter to cause ultrafiltrate to pass through the ultrafiltrate outlet;

a first control reservoir; and a first connector for attaching the portable module to the ultrafiltrate outlet of the hemofilter;

wherein the second port of the hemofilter remains sealed during operation of the portable module;

wherein one or more controllers controls the filtrate control pump so that ultrafiltrate is separated and removed from the blood in the extracorporeal circuit and also so that blood is conveyed from the patient, through the extracorporeal circuit and the hemofilter, and returned to the patient;

operating the filtrate pump to separate and remove an ultrafiltrate from the blood in the extracorporeal circuit for a first period of time;

disconnecting the portable module from the hemofilter;

attaching the ultrafiltrate outlet and the dialysate inlet to a controlled compliant urea removal module, the urea removal module comprising a sorbent cartridge having at least urease and zirconium phosphate or magnesium phosphate therein, the urea removal module further comprising a dialysis circuit and one or more second connectors for attaching the dialysis circuit to the ultrafiltrate outlet and to the second port;

wherein the dialysis circuit of the urea removal module comprises one or more second control reservoirs and one or more control pumps, the one or more second control pumps configured to be controlled by the one or more controllers;

conveying dialysate through the dialysis circuit such that the dialysate moves from the sorbent cartridge to the hemofilter and back to the sorbent cartridge, wherein the blood and the dialysate are in fluid communication through the hemofiltration membrane and one or more waste products diffuses from the blood to the dialysate;

removing the one or more waste products from the dialysate during a second period of time wherein the urea is removed by the sorbent cartridge;

wherein the one or more second control pumps are configured to provide selective adjustment of the volume of the second dialysis circuit by (A) operating in an influx direction so that fluid moves from the one or more second control reservoirs to the second dialysis circuit; and (B) operating in an efflux direction so that fluid moves from the second dialysis circuit into the one or more second control reservoirs;

wherein controlled compliance of the urea removal module is achieved by actively controlling, via the one or more controllers, the influx and efflux of fluid to and from both the second dialysis circuit and the extracorporeal circuit, without the use of scales or gravimetric methods.

17. The method of claim 16, further comprising operating either the first control pump or second control pump to add fluid from a control reservoir to the dialysis circuit in an influx direction via a conduit, and operating either the first control pump or second control pump to remove fluid from the dialysis circuit to the control reservoir in an efflux direction via a conduit, and intermittently switching between pumping fluid in the efflux direction to move fluid across the dialysis membrane from the extracorporeal circuit to the dialysis circuit and the influx direction to move fluid across the dialysis membrane from the dialysis circuit to the extracorporeal circuit, wherein the intermittent switching between pumping in the efflux and influx directions accomplishes the convective clearance of at least one waste species having a molecular weight less than about 66000 g/mol and greater than about 1000 g/mol.

18. The method of claim 16, wherein pumping in the efflux and influx directions is intermittently switched between the efflux direction and the influx direction at least once every minute.

19. The method of claim 16, wherein at least one of the one or more control pumps operates to pump a larger volume in the efflux direction compared with the influx direction over a period of time.

* * * * *